(12) United States Patent
Utsumi et al.

(10) Patent No.: US 8,247,160 B2
(45) Date of Patent: Aug. 21, 2012

(54) RESIST COMPOSITION, METHOD OF FORMING RESIST PATTERN, AND NOVEL COMPOUND AND ACID GENERATOR

(75) Inventors: Yoshiyuki Utsumi, Kawasaki (JP); Keita Ishiduka, Kawasaki (JP); Kensuke Matsuzawa, Kawasaki (JP); Akiya Kawaue, Kawasaki (JP); Hiroaki Shimizu, Kawasaki (JP); Tsuyoshi Nakamura, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 351 days.

(21) Appl. No.: 12/501,981

(22) Filed: Jul. 13, 2009

(65) Prior Publication Data
US 2010/0015555 A1    Jan. 21, 2010

(30) Foreign Application Priority Data

Jul. 18, 2008   (JP) .................... 2008-187717
Nov. 21, 2008   (JP) .................... 2008-298679

(51) Int. Cl.
G03F 7/039     (2006.01)
G03F 7/20      (2006.01)
G03F 7/30      (2006.01)
C07C 309/65    (2006.01)

(52) U.S. Cl. .............. 430/270.1; 430/326; 430/921; 430/922; 430/925; 430/910; 430/311; 562/100; 562/108; 562/109; 562/110; 562/111; 562/113

(58) Field of Classification Search .......... None
See application file for complete search history.

(56) References Cited

U.S. PATENT DOCUMENTS

| 5,945,517 A | 8/1999 | Nitta et al. |
| 6,153,733 A | 11/2000 | Yukawa et al. |
| 7,074,543 B2 | 7/2006 | Iwai et al. |
| 7,960,087 B2 * | 6/2011 | Kodama ............. 430/270.1 |
| 2006/0228648 A1 * | 10/2006 | Ohsawa et al. ........ 430/270.1 |
| 2009/0226842 A1 * | 9/2009 | Shimizu et al. ........ 430/281.1 |
| 2009/0234155 A1 * | 9/2009 | Oh et al. ............... 562/100 |
| 2009/0317745 A1 * | 12/2009 | Mimura et al. ........ 430/281.1 |

FOREIGN PATENT DOCUMENTS

| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| JP | 2005-037888 | 2/2005 |
| JP | 2005-336452 | 12/2005 |
| JP | 2006-259582 | 9/2006 |
| WO | WO 2004-074242 | 9/2004 |

* cited by examiner

*Primary Examiner* — Sin J. Lee
(74) *Attorney, Agent, or Firm* — Knobbe Martens Olson & Bear LLP

(57) ABSTRACT

A resist composition including a base component that exhibits changed solubility in an alkali developing solution under the action of acid, and an acid generator consisting of a compound represented by general formula (b1). In formula (b1), $Y^1$ represents a fluorinated alkylene group of 1 to 4 carbon atoms, X represents an aliphatic cyclic group of 3 to 30 carbon atoms, $R^{11'}$ to $R^{13'}$ each represents an aryl group or alkyl group, provided that at least one of $R^{11'}$ to $R^{13'}$ is an aryl group having a substituent represented by general formula (b1-0), and two alkyl groups among $R^{11'}$ to $R^{13'}$ may be bonded to each other to form a ring with the sulfur atom in the formula. In formula (b1-0), $R^{52}$ represents a chain-like or cyclic hydrocarbon group, and f and g each represents 0 or 1.

[Chemical Formula 1]

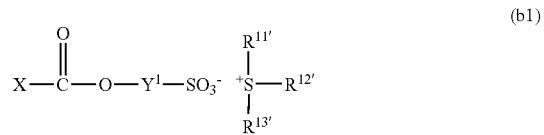

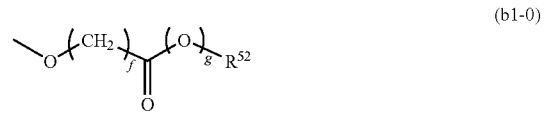

14 Claims, No Drawings

RESIST COMPOSITION, METHOD OF FORMING RESIST PATTERN, AND NOVEL COMPOUND AND ACID GENERATOR

BACKGROUND OF THE INVENTION

1. Field of the Invention

The present invention relates to a resist composition, a method of forming a resist pattern that uses the resist composition, a novel compound that is useful as an acid generator within the resist composition, and an acid generator.

Priority is claimed on Japanese Patent Application No. 2008-187717, filed Jul. 18, 2008, and Japanese Patent Application No. 2008-298679, filed Nov. 21, 2008, the contents of which are incorporated herein by reference.

2. Description of Related Art

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive composition, and a resist material in which the exposed portions become insoluble in a developing solution is called a negative composition.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, EUV (extreme ultraviolet radiation), and X rays.

Resist materials for use with these types of exposure light sources require lithography properties such as a high resolution capable of reproducing patterns of minute dimensions, and a high level of sensitivity to these types of exposure light sources.

As a resist material which satisfies these conditions, a chemically amplified resist composition is used, which includes a base component that exhibits changed solubility in an alkali developing solution under the action of acid and an acid generator that generates acid upon exposure.

For example, a chemically amplified positive resist composition typically contains a resin component (a base resin) that exhibits increased solubility in an alkali developing solution under the action of acid, and an acid generator component. When a resist film formed from such a resist composition is subjected to selective exposure during formation of a resist pattern, acid is generated from the acid generator by the exposure within the exposed portions, and the action of that acid causes an increase in the solubility of the resin component within an alkali developing solution, causing the exposed portions to become soluble in the alkali developing solution.

Resins that contain structural units derived from (meth)acrylate esters within the main chain (acrylic resins) are now widely used as base resins for resists that use ArF excimer laser lithography, as they exhibit excellent transparency in the vicinity of 193 nm (for example, see Patent Document 1).

In this description, the term "(meth)acrylic acid" is a generic term that includes either or both of acrylic acid having a hydrogen atom bonded to the α-position and methacrylic acid having a methyl group bonded to the α-position. The term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

In terms of the acid generator used in a chemically amplified resist, a multitude of different acid generators have been proposed including, for example, onium salt-based acid generators such as iodonium salts and sulfonium salts, oxime sulfonate-based acid generators, diazomethane-based acid generators, nitrobenzylsulfonate-based acid generators, iminosulfonate-based acid generators, and disulfone-based acid generators.

Currently, onium salt-based acid generators containing an onium ion such as a triphenylsulfonium ion as the cation moiety are widely used as the acid generator. The anion moiety of these onium salt-based acid generators is typically an alkylsulfonate ion or a fluorinated alkylsulfonate ion in which some or all of the hydrogen atoms of the alkyl group have been substituted with fluorine atoms (for example, see Patent Document 2).

[Patent Document 1] Japanese Unexamined Patent Application, First Publication No. 2003-241385

[Patent Document 2] Japanese Unexamined Patent Application, First Publication No. 2005-37888

SUMMARY OF THE INVENTION

With the expectation of further progress in lithography techniques and ongoing reductions in the size of resist patterns, there are growing demands for resist materials capable of achieving higher resolution.

However, with conventional resist compositions, if a very fine pattern is formed at a narrow pitch, such as a hole pattern having a hole diameter of approximately 100 nm or smaller, then collapse of the pattern shape becomes a problem. Accordingly, there are strong demands for a resist composition which, during formation of a hole pattern, is capable of forming a resist pattern that exhibits a high degree of hole circularity and a favorable pattern shape.

The present invention has been developed in light of the above circumstances, and has an object of providing a resist composition and method of forming a resist pattern that are capable of forming a resist pattern of favorable shape, as well as an acid generator for the resist composition and a novel compound that is useful as the acid generator.

In order to achieve the above object, the inventors of the present invention propose the following aspects.

Specifically, a first aspect of the present invention is a resist composition including a base component (A) that exhibits changed solubility in an alkali developing solution under action of acid, and an acid generator component (B) that generates acid upon exposure, wherein the acid generator component (B) includes an acid generator (B1) consisting of a compound represented by general formula (b1) shown below.

[Chemical Formula 1]

$$X-\overset{O}{\underset{\|}{C}}-O-Y^1-SO_3^- \quad {}^+\underset{\underset{R^{13\prime}}{|}}{\overset{\underset{|}{R^{11\prime}}}{S}}-R^{12\prime} \quad (b1)$$

wherein $Y^1$ represents a fluorinated alkylene group of 1 to 4 carbon atoms that may have a substituent, X represents an aliphatic cyclic group of 3 to 30 carbon atoms that may have a substituent, $R^{11\prime}$ to $R^{13\prime}$ each independently represents an aryl group or alkyl group that may have a substituent, provided that at least one of $R^{11\prime}$ to $R^{13\prime}$ is an aryl group having a substituent represented by general formula (b1-0) shown below, and two alkyl groups among $R^{11\prime}$ to $R^{13\prime}$ may be bonded to each other to form a ring with the sulfur atom in the formula.

[Chemical Formula 2]

$$\diagdown_O{+CH_2+}_f\underset{\underset{O}{\|}}{C}{+O+}_g R^{52} \quad (b1\text{-}0)$$

wherein $R^{52}$ represents a chain-like or cyclic hydrocarbon group, f represents 0 or 1, and g represents 0 or 1.

A second aspect of the present invention is a method of forming a resist pattern, including: using a resist composition of the first aspect to form a resist film on a substrate, conducting exposure of the resist film, and alkali-developing the resist film to form a resist pattern.

A third aspect of the present invention is a compound represented by general formula (b1) shown below.

[Chemical Formula 3]

$$X-\overset{O}{\underset{\|}{C}}-O-Y^1-SO_3^- \quad {}^+\underset{\underset{R^{13\prime}}{|}}{\overset{\underset{|}{R^{11\prime}}}{S}}-R^{12\prime} \quad (b1)$$

wherein $Y^1$ represents a fluorinated alkylene group of 1 to 4 carbon atoms that may have a substituent, X represents an aliphatic cyclic group of 3 to 30 carbon atoms that may have a substituent, $R^{11\prime}$ to $R^{13\prime}$ each independently represents an aryl group or alkyl group that may have a substituent, provided that at least one of $R^{11\prime}$ to $R^{13\prime}$ is an aryl group having a substituent represented by general formula (b1-0) shown below, and two alkyl groups among $R^{11\prime}$ to $R^{13\prime}$ may be bonded to each other to form a ring with the sulfur atom in the formula.

[Chemical Formula 4]

$$\diagdown_O{+CH_2+}_f\underset{\underset{O}{\|}}{C}{+O+}_g R^{52} \quad (b1\text{-}0)$$

wherein $R^{52}$ represents a chain-like or cyclic hydrocarbon group, f represents 0 or 1, and g represents 0 or 1.

A fourth aspect of the present invention is an acid generator consisting of a compound of the third aspect.

In the present description and claims, the term "alkyl group" includes linear, branched and cyclic monovalent saturated hydrocarbon groups, unless otherwise specified.

The term "alkylene group" includes linear, branched and cyclic divalent saturated hydrocarbon groups, unless otherwise specified.

A "lower alkyl group" is an alkyl group of 1 to 5 carbon atoms.

A "halogenated alkyl group" describes a group in which some or all of the hydrogen atoms of an alkyl group have been substituted with halogen atoms, wherein examples of the halogen atom include a fluorine atom, chlorine atom, bromine atom or iodine atom.

The term "structural unit" refers to a monomer unit that contributes to the formation of a polymer compound (a polymer or copolymer).

The term "exposure" is used as a general concept that includes irradiation with any form of radiation.

The present invention is able to provide a resist composition and method of forming a resist pattern that enable the formation of a resist pattern of favorable shape, as well as an acid generator for the resist composition and a novel compound that is useful as the acid generator.

DETAILED DESCRIPTION OF THE INVENTION

<<Resist Composition>>

The resist composition of the first aspect of the present invention includes a base component (A) (hereafter, referred to as "component (A)") that exhibits changed solubility in an alkali developing solution under the action of acid and an acid generator component (B) (hereafter, referred to as "component (B)") that generates acid upon exposure.

With a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas the unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

Organic compounds having a molecular weight of 500 or more are broadly classified into low molecular weight organic compounds having a molecular weight of 500 to less than 2,000 (hereafter, frequently referred to as "low molecular weight compounds") and high molecular weight resins (polymeric materials) having a molecular weight of 2,000 or more. Generally, as the aforementioned low molecular weight compound, a non-polymer is used. With respect to the aforementioned resin (polymer or copolymer), the molecular weight refers to the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under the action of acid may be used. Alternatively, a low molecular weight material which exhibits changed solubility in an alkali developing solution under the action of acid may be used as the component (A).

When the resist composition of the present invention is a negative resist composition, a base component that is soluble in an alkali developing solution is used as the component (A), and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition to a support, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, or a resin having a fluorinated alcohol group disclosed in Japanese Unexamined Patent Application, First Publication No. 2005-336452 or Japanese Unexamined Patent Application, First Publication No. 2006-259582, as such resins enable the formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables the formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, a base component (hereafter referred to as "component (A)") that exhibits increased solubility in an alkali developing solution under the action of acid is used as the component (A).

The component (A) is insoluble in an alkali developing solution prior to exposure, and when acid is generated from the component (B) upon exposure, the solubility of the component (A') in an alkali developing solution increases. Therefore, in the formation of a resist pattern, by conducting selective exposure of a resist film formed by applying the positive resist composition to a support, the exposed portions change from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component that exhibits increased solubility in an alkali developing solution under the action of acid (namely, the component (A')). That is, the resist composition of the present invention is preferably a positive resist composition.

The component (A') may be a resin component (A1) that exhibits increased solubility in an alkali developing solution under the action of acid (hereafter, referred to as "component (A1)"), a low molecular weight compound (A2) that exhibits increased solubility in an alkali developing solution under action of acid (hereafter, referred to as "component (A2)"), or a mixture of the component (A1) and the component (A2).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit that is formed by the cleavage of the ethylenic double bond of an acrylate ester.

The term "acrylate ester" is a generic term that includes the acrylate ester having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the α-position (the carbon atom on the α-position) refers to the carbon atom having the carbonyl group bonded thereto, unless specified otherwise.

In the acrylate ester, specific examples of the lower alkyl group for the substituent at the α-position include linear or branched lower alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of the halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, and a hydrogen atom, a lower alkyl group or a fluorinated lower alkyl group is more preferred. In terms of industrial availability, a hydrogen atom or a methyl group is particularly desirable.

In the resist composition of the present invention, it is particularly desirable that the component (A1) have a structural unit (a1) derived from an acrylate ester containing an acid-dissociable, dissolution-inhibiting group.

Further, it is preferable that the component (A1) have a structural unit (a2) derived from an acrylate ester containing a lactone-containing cyclic group, in addition to the structural unit (a1).

Furthermore, it is preferable that the component (A1) have a structural unit (a3) derived from an acrylate ester containing a polar group-containing aliphatic hydrocarbon group, in addition to either the structural unit (a1), or the structural unit (a1) and the structural unit (a2).

Structural Unit (a1)

The structural unit (a1) is a structural unit derived from an acrylate ester containing an acid-dissociable, dissolution-inhibiting group.

As the acid-dissociable, dissolution-inhibiting group in the structural unit (a1), any of the groups that have been proposed as acid-dissociable, dissolution-inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid, and acetal-type acid-dissociable, dissolution-inhibiting groups such as alkoxyalkyl groups are widely known.

Here, a "tertiary alkyl ester" describes a structure in which an ester is formed by substituting the hydrogen atom of a carboxyl group with a chain-like or cyclic tertiary alkyl group, and a tertiary carbon atom within the chain-like or cyclic alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of these tertiary alkyl ester-type acid-dissociable, dissolution-inhibiting groups include aliphatic branched, acid-dissociable, dissolution-inhibiting groups and aliphatic cyclic group-containing acid-dissociable, dissolution-inhibiting groups.

In the present description, the term "aliphatic" is a relative concept used in relation to the term "aromatic", and defines a group or compound that has no aromaticity.

The description "aliphatic branched" refers to a branched structure having no aromaticity.

The structure of an "aliphatic branched, acid-dissociable, dissolution-inhibiting group" is not limited to structures composed only of carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid-dissociable, dissolution-inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, a fluorine atom, fluorinated lower alkyl groups of 1 to 5 carbon atoms, and an oxygen atom (=O).

The basic ring structure of the "aliphatic cyclic group" exclusive of substituents is not limited to structures composed only of carbon and hydrogen (not limited to hydrocarbon groups), but is preferably a hydrocarbon group.

Further, the "hydrocarbon group" may be either saturated or unsaturated, but is preferably saturated. Moreover, the "aliphatic cyclic group" is preferably a polycyclic group.

Examples of such aliphatic cyclic groups include groups in which one or more hydrogen atoms have been removed from a monocycloalkane or a polycycloalkane such as a bicycloalkane, tricycloalkane or tetracycloalkane, which may or may not be substituted with a lower alkyl group, a fluorine atom or a fluorinated lower alkyl group. Specific examples include groups in which one or more hydrogen atoms have been removed from a monocycloalkane such as cyclopentane or cyclohexane or a polycycloalkane such as adamantane, norbornane, isobornane, tricyclodecane or tetracyclododecane.

Examples of the aliphatic cyclic group-containing acid-dissociable, dissolution-inhibiting groups include groups having a tertiary carbon atom on the ring structure of a cycloalkyl group. Specific examples include a 2-methyl-2-adamantyl group and a 2-ethyl-2-adamantyl group. Further examples include groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, such as the groups bonded to the oxygen atom of the carbonyloxy group (—C(O)—O—) within the structural units represented by general formulas (a1"-1) to (a1"-6) shown below.

[Chemical Formula 5]

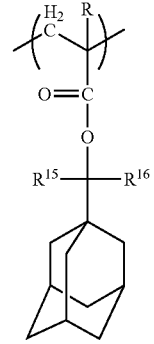

(a1"-1)

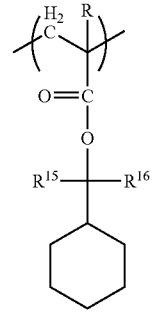

(a1"-2)

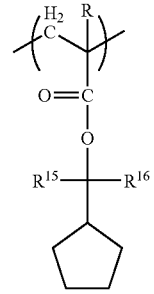

(a1"-3)

-continued (a1″-4)
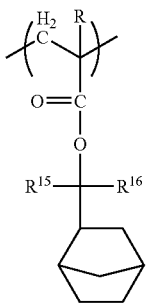

(a1″-5)
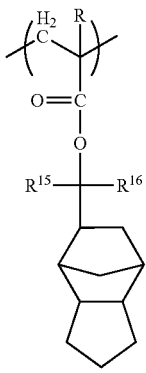

(a1″-6)
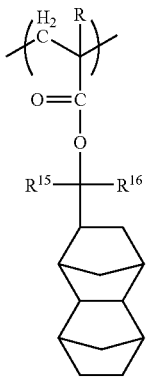

wherein R represents a hydrogen atom, a lower alkyl group or a halogenated lower alkyl group, and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group that may be bonded to the α-position of the aforementioned acrylate ester.

An "acetal-type acid-dissociable, dissolution-inhibiting group" generally substitutes a hydrogen atom at the terminal of an alkali-soluble group such as a carboxyl group or hydroxyl group, so as to be bonded to an oxygen atom. When acid is generated upon exposure, the action of the generated acid causes cleavage of the bond between the acetal-type acid-dissociable, dissolution-inhibiting group and the oxygen atom to which the acetal-type acid-dissociable, dissolution-inhibiting group is bonded.

Examples of acetal-type acid-dissociable, dissolution-inhibiting groups include groups represented by general formula (p1) shown below.

[Chemical Formula 6]

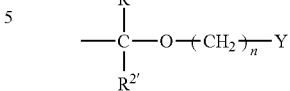

(p1)

wherein $R^{1\prime}$ and $R^{2\prime}$ each independently represents a hydrogen atom or a lower alkyl group, n represents an integer of 0 to 3, and Y represents a lower alkyl group or an aliphatic cyclic group.

In general formula (p1) above, n is preferably an integer of 0 to 2, more preferably 0 or 1, and is most preferably 0.

Examples of the lower alkyl group for $R^{1\prime}$ and $R^{2\prime}$ include the same lower alkyl groups as those exemplified above for R, and of these, a methyl group or ethyl group is preferred, and a methyl group is particularly desirable.

In the present invention, it is preferable that at least one of $R^{1\prime}$ and $R^{2\prime}$ is a hydrogen atom. That is, it is preferable that the acid-dissociable, dissolution-inhibiting group (p1) is a group represented by general formula (p1-1) shown below.

[Chemical Formula 7]

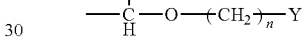

(p1-1)

wherein $R^{1\prime}$, n and Y are as defined above.

Examples of the lower alkyl group for Y include the same lower alkyl groups as those exemplified above for R above.

As the aliphatic cyclic group for Y, any of the multitude of monocyclic or polycyclic aliphatic cyclic groups that have been proposed for conventional ArF resists and the like may be appropriately selected for use. Specific examples include the same groups described above in connection with the "aliphatic cyclic group".

Further examples of the acetal-type, acid-dissociable, dissolution-inhibiting group include groups represented by general formula (p2) shown below.

[Chemical Formula 8]

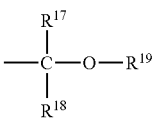

(p2)

wherein $R^{17}$ and $R^{18}$ each independently represents a linear or branched alkyl group or a hydrogen atom, and $R^{19}$ represents a linear, branched or cyclic alkyl group, or alternatively, $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, may be either linear or branched, is preferably an ethyl group or a methyl group, and is most preferably a methyl group. Groups in which one of $R^{17}$ and $R^{18}$ is a hydrogen atom and the other is a methyl group are particularly desirable.

$R^{19}$ represents a linear, branched or cyclic alkyl group that preferably contains 1 to 15 carbon atoms, and may be a linear, branched or cyclic group.

When $R^{19}$ represents a linear or branched alkyl group, it is preferably an alkyl group of 1 to 5 carbon atoms, is more preferably an ethyl group or methyl group, and is most preferably an ethyl group.

When $R^{19}$ represents a cyclic group, it is preferably a group of 4 to 15 carbon atoms, more preferably 4 to 12 carbon atoms, and most preferably 5 to 10 carbon atoms. Examples of the cyclic group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (and preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and is more preferably a 4- to 6-membered ring. Specific examples of the cyclic group include a tetrahydropyranyl group and a tetrahydrofuranyl group.

As the structural unit (a1), it is preferable to use at least one unit selected from the group consisting of structural units represented by general formula (a1-0-1) shown below and structural units represented by general formula (a1-0-2) shown below.

[Chemical Formula 9]

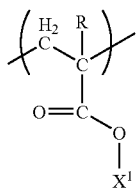

(a1-0-1)

wherein R represents a hydrogen atom, a lower alkyl group or a halogenated lower alkyl group, and $X^1$ represents an acid-dissociable, dissolution-inhibiting group.

[Chemical Formula 10]

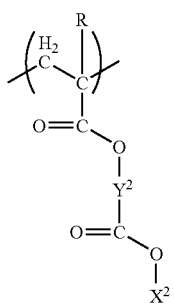

(a1-0-2)

wherein R represents a hydrogen atom, a lower alkyl group or a halogenated lower alkyl group, $X^2$ represents an acid-dissociable, dissolution-inhibiting group, and $Y^2$ represents a divalent linking group.

In general formula (a1-0-1) shown above, the lower alkyl group and halogenated lower alkyl group for R are the same as the lower alkyl group and halogenated lower alkyl group that may be bonded to the α-position of the aforementioned acrylate ester, and examples of these groups are as listed above.

$X^1$ is not particularly limited as long as it is an acid-dissociable, dissolution-inhibiting group. Examples thereof include the aforementioned tertiary alkyl ester-type acid-dissociable, dissolution-inhibiting groups and acetal-type acid-dissociable, dissolution-inhibiting groups, and tertiary alkyl ester-type acid-dissociable, dissolution-inhibiting groups are preferable.

In general formula (a1-0-2), R is as defined above, and examples thereof are as exemplified above.

$X^2$ is the same as $X^1$ in general formula (a1-0-1), and examples thereof are as exemplified above.

Examples of the divalent linking group for $Y^2$ include alkylene groups, divalent aliphatic cyclic groups, divalent linking groups that include a hetero atom, and combinations thereof.

Examples of the divalent aliphatic cyclic group include the same groups as those exemplified above within the description of the "aliphatic cyclic group" with the exception that two or more hydrogen atoms have been removed therefrom.

When $Y^2$ represents an alkylene group, the group preferably contains 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, it is particularly desirable that the divalent aliphatic cyclic group is a group in which two or more hydrogen atoms have been removed from cyclopentane, cyclohexane, norbornane, isobornane, adamantane, tricyclodecane or tetracyclododecane.

When $Y^2$ represents a divalent linking group that includes a hetero atom, examples thereof include —O—, —C(=O)—O—, —C(=O)—, —O—C(=O)—O—, —C(=O)—NH—, —$NR^{04}$— (wherein, $R^{04}$ is an alkyl group or an acyl group or the like), —NH—C(=O)—, =N—, —S—, —S(=O)$_2$—, —S(=O)$_2$—O—, and -A-O (oxygen atom)-B- (wherein A and B each independently represents a divalent hydrocarbon group that may have a substituent).

Within the group —$NR^{04}$— for $Y^2$, the number of carbon atoms within the group $R^{04}$ is preferably 1 to 10 carbon atoms, more preferably 1 to 8 carbon atoms, and most preferably 1 to 5 carbon atoms.

When $Y^2$ represents -A-O—B—, A and B each independently represents a divalent hydrocarbon group that may have a substituent. The description that the hydrocarbon group "may have a substituent" means that some or all of the hydrogen atoms within the hydrocarbon group may be substituted with an atom other than a hydrogen atom or with a group.

The hydrocarbon group for A may be an aliphatic hydrocarbon group or an aromatic hydrocarbon group. An "aliphatic hydrocarbon group" describes a hydrocarbon group that contains no aromaticity.

The aliphatic hydrocarbon group for A may be saturated or unsaturated, but is preferably saturated.

More specific examples of the aliphatic hydrocarbon group for A include linear or branched aliphatic hydrocarbon groups, and aliphatic hydrocarbon groups that include a ring within the structure.

The linear or branched aliphatic hydrocarbon group preferably contains 1 to 10 carbon atoms, more preferably 1 to 8 carbon atoms, still more preferably 2 to 5 carbon atoms, and most preferably 2 carbon atoms.

As the linear aliphatic hydrocarbon group, linear alkylene groups are preferred, and specific examples include a methylene group, ethylene group [—$(CH_2)_2$—], trimethylene group [—$(CH_2)_3$—], tetramethylene group [—$(CH_2)_4$—], or pentamethylene group [—$(CH_2)_5$—].

As the branched aliphatic hydrocarbon group, branched alkylene groups are preferred, and specific examples include alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; alkylethylene groups such as —$CH(CH_3)CH_2$—, —$CH(CH_3)CH(CH_3)$—, —$C(CH_3)_2CH_2$— and —$CH(CH_2CH_3)CH_2$—; alkyltrimethylene groups such as —$CH(CH_3)CH_2CH_2$— and —$CH_2CH(CH_3)CH_2$—; and alkyltetramethylene groups such as —$CH(CH_3)CH_2CH_2CH_2$— and —$CH_2CH(CH_3)CH_2CH_2$—. The alkyl group within the alkylalkylene group is preferably an alkyl group of 1 to 5 carbon atoms.

These chain-like aliphatic hydrocarbon groups may or may not have a substituent. Examples of possible substituents include a fluorine atom, a fluorinated alkyl group of 1 to 5 carbon atoms, and an oxygen atom (=O).

Examples of the aliphatic hydrocarbon group that includes a ring within the structure include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an above-mentioned chain-like aliphatic hydrocarbon group, or disposed partway along a chain-like aliphatic hydrocarbon group.

The cyclic aliphatic hydrocarbon group preferably contains from 3 to 20 carbon atoms, and more preferably 3 to 12 carbon atoms.

The cyclic aliphatic hydrocarbon group may be either a polycyclic group or a monocyclic group. The monocyclic group is preferably a group in which two hydrogen atoms have been removed from a monocycloalkane of 3 to 6 carbon atoms, and specific examples of the monocycloalkane include cyclopentane and cyclohexane.

The polycyclic group is preferably a group in which two hydrogen atoms have been removed from a polycycloalkane of 7 to 12 carbon atoms, and specific examples of the polycycloalkane include adamantane, norbornane, isobornane, tricyclodecane, and tetracyclododecane.

The cyclic aliphatic hydrocarbon group may or may not have a substituent, and examples of the substituent include a lower alkyl group of 1 to 5 carbon atoms, a fluorine atom, a fluorinated lower alkyl group of 1 to 5 carbon atoms, and an oxygen atom (=O).

As the group A, a linear aliphatic hydrocarbon group is preferred, a linear alkylene group is more preferred, a linear alkylene group of 2 to 5 carbon atoms is still more preferred, and a methylene group or ethylene group is the most desirable.

Examples of the hydrocarbon group for B include the same divalent hydrocarbon groups as those exemplified above for A.

B is preferably a linear or branched aliphatic hydrocarbon group, and is most preferably a methylene group or alkylmethylene group.

The alkyl group within the alkylmethylene group is preferably a linear alkyl group of 1 to 5 carbon atoms, more preferably a linear alkyl group of 1 to 3 carbon atoms, and is most preferably a methyl group.

The divalent linking group for $Y^2$ is preferably an alkylene group, a divalent aliphatic cyclic group, or a divalent linking group containing an alkylene group and a hetero atom, and is most preferably a divalent linking group containing an alkylene group and a hetero atom.

More specific examples of the structural unit (a1) include structural units represented by general formulas (a1-1) to (a1-4) shown below.

[Chemical Formula 11]

(a1-1)

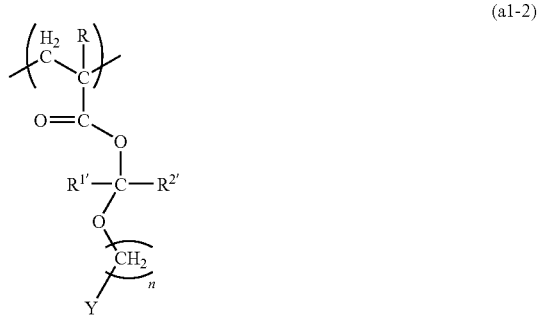

(a1-2)

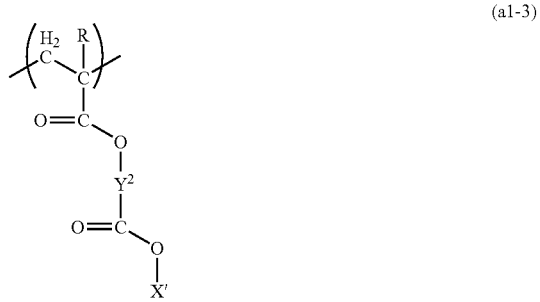

(a1-3)

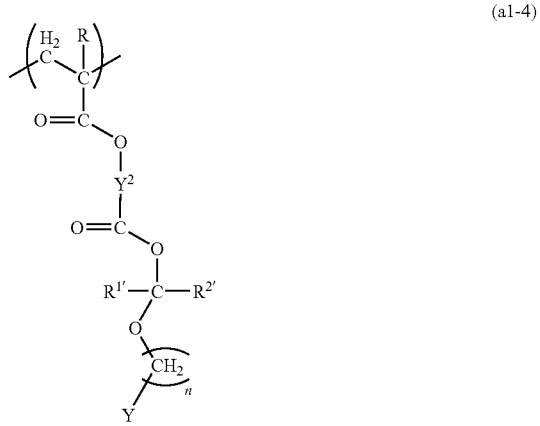

(a1-4)

wherein X' represents a tertiary alkyl ester-type acid-dissociable, dissolution-inhibiting group, Y represents a lower alkyl group of 1 to 5 carbon atoms or an aliphatic cyclic group, n represents an integer of 0 to 3, $Y^2$ represents a divalent linking group, R is as defined above, and $R^{1'}$ and $R^{2'}$ each independently represents a hydrogen atom or a lower alkyl group of 1 to 5 carbon atoms.

In the above formulas, examples of X' include the same tertiary alkyl ester-type acid-dissociable, dissolution-inhibiting groups as those exemplified above for $X^1$.

$R^{1'}$, $R^{2'}$, n and Y are as defined for $R^{1'}$, $R^{2'}$, n and Y in general formula (p1) described above in connection with the "acetal-type acid-dissociable, dissolution-inhibiting group".

Examples of $Y^2$ include the same groups as those exemplified above for $Y^2$ in general formula (a1-0-2).
Specific examples of structural units represented by general formula (a1-1) to (a1-4) are shown below.
[Chemical Formula 12]
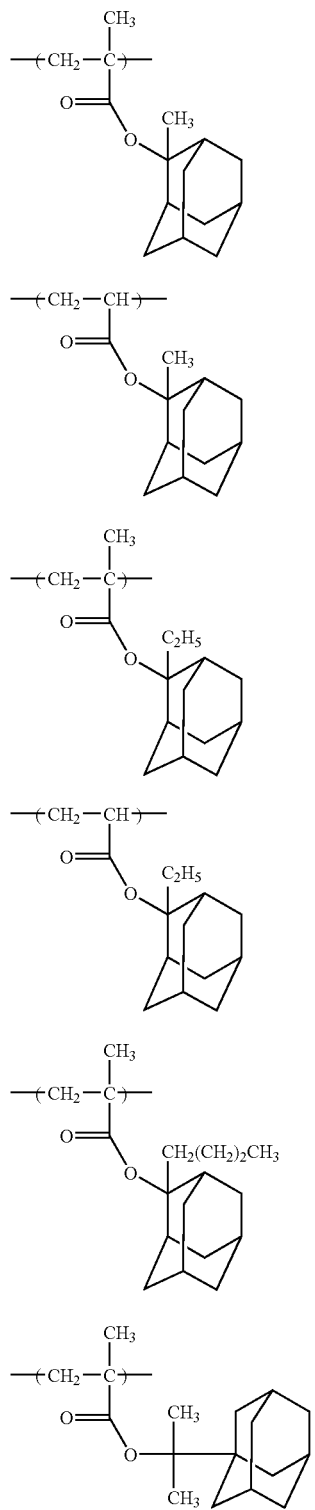
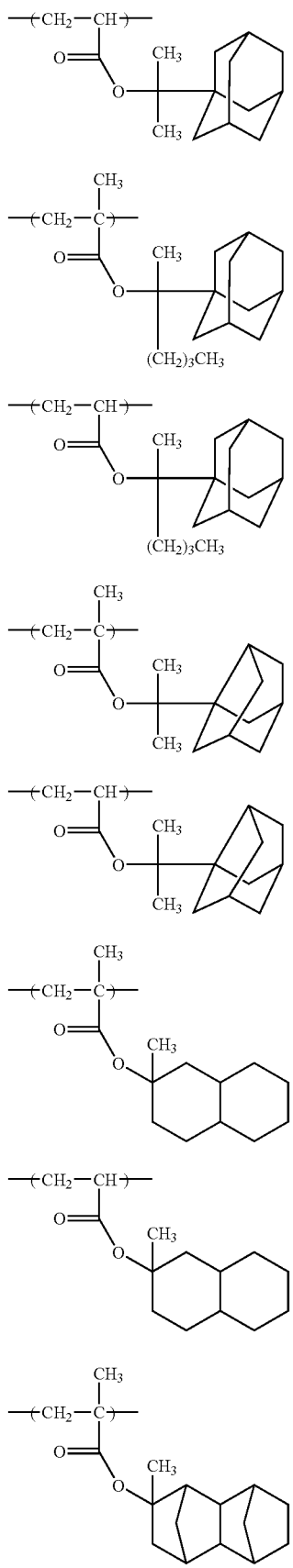

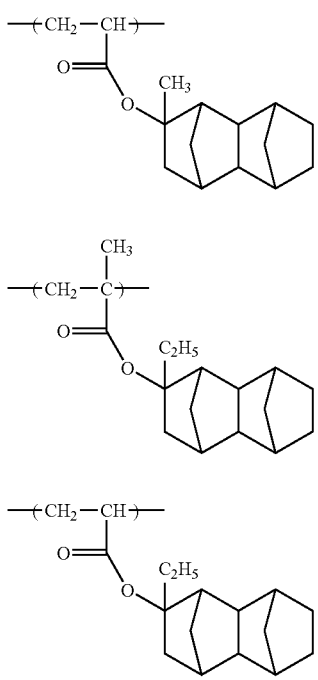
(a1-1-15)
(a1-1-16)
(a1-1-17)
[Chemical Formula 13]
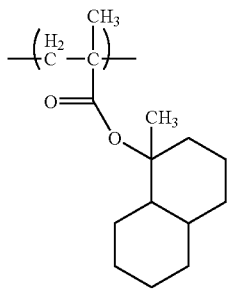
(a1-1-18)
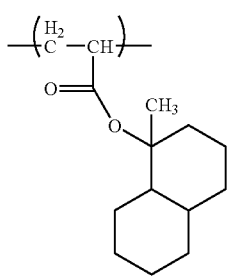
(a1-1-19)
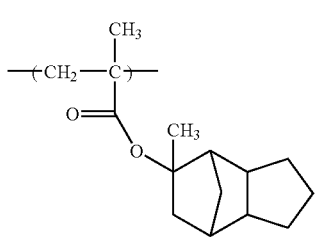
(a1-1-20)
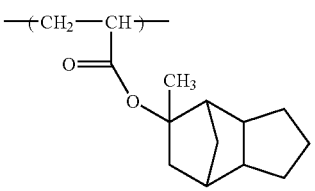
(a1-1-21)
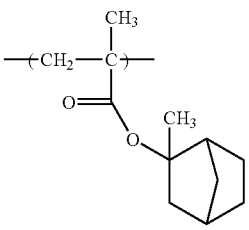
(a1-1-22)
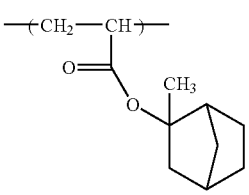
(a1-1-23)
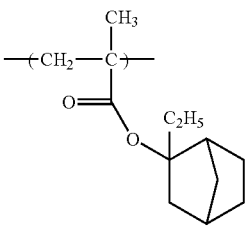
(a1-1-24)
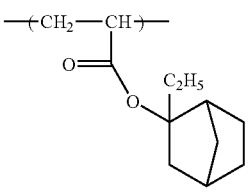
(a1-1-25)
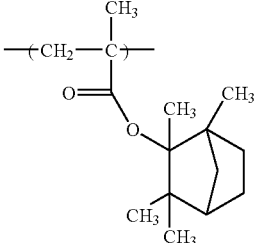
(a1-1-26)
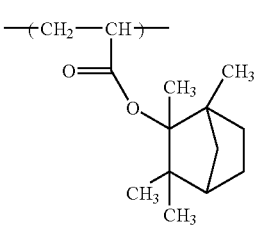
(a1-1-27)

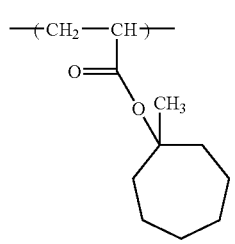 (a1-1-28)
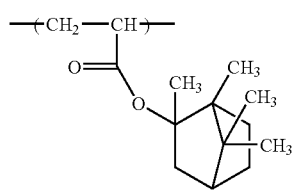 (a1-1-29)
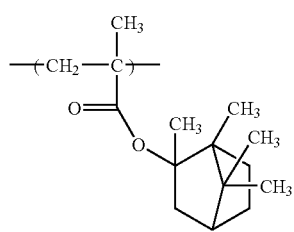 (a1-1-30)
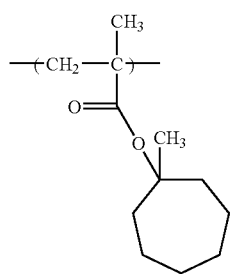 (a1-1-31)
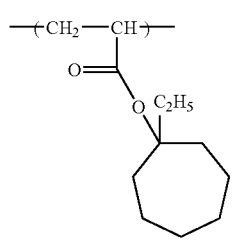 (a1-1-32)
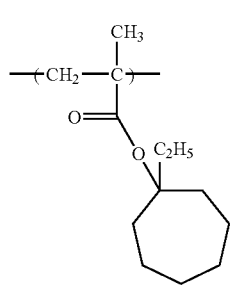 (a1-1-33)
[Chemical Formula 14]
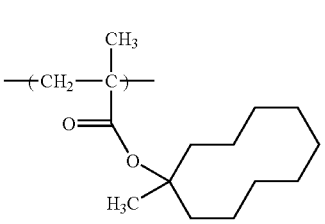 (a1-1-34)
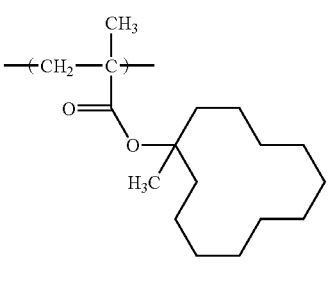 (a1-1-35)
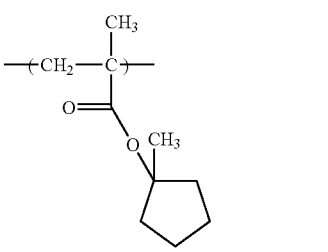 (a1-1-36)
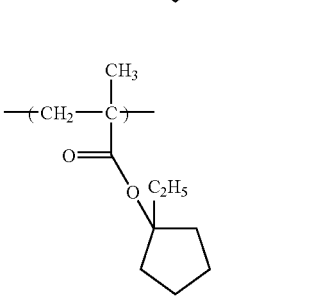 (a1-1-37)
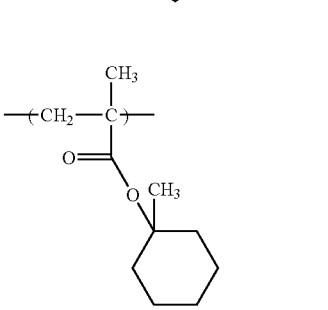 (a1-1-38)
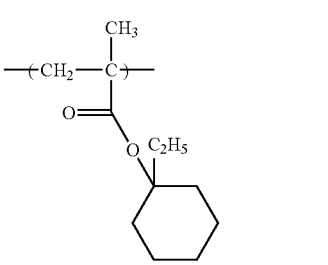 (a1-1-39)

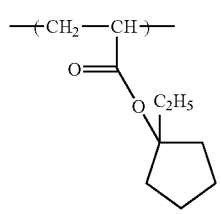 (a1-1-40)
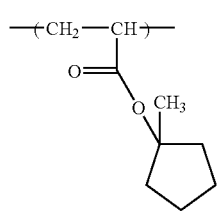 (a1-1-41)
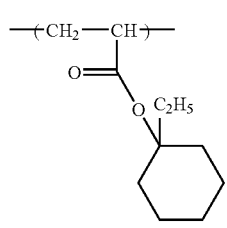 (a1-1-42)
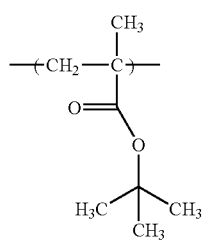 (a1-1-43)
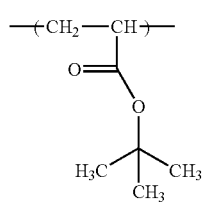 (a1-1-44)
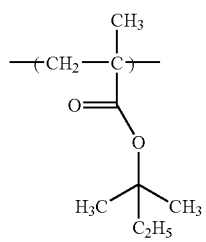 (a1-1-45)
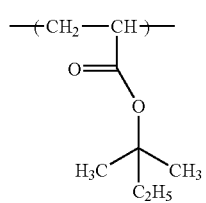 (a1-1-46)
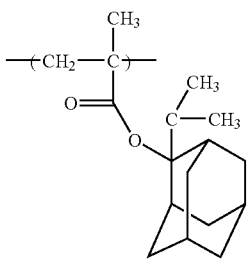 (a1-1-47)
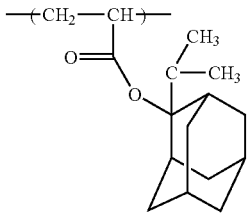 (a1-1-48)
[Chemical Formula 15]
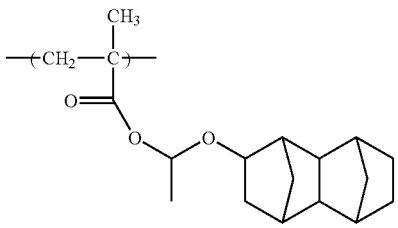 (a1-2-1)
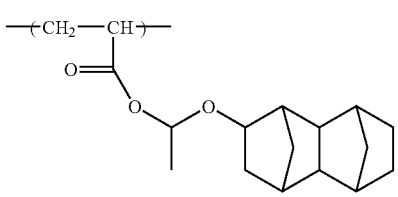 (a1-2-2)
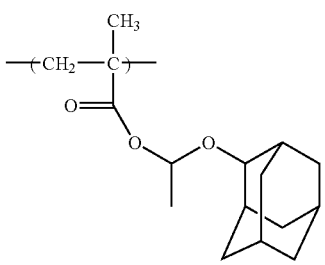 (a1-2-3)
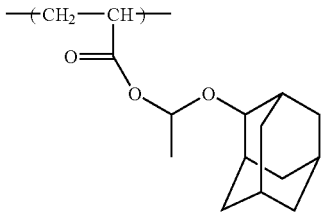 (a1-2-4)

(a1-2-5) 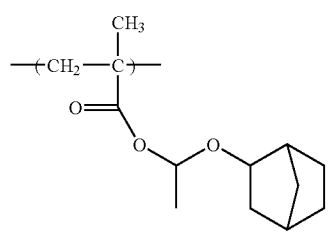
(a1-2-6) 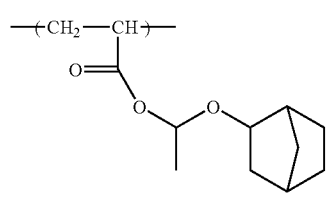
[Chemical Formula 16]
(a1-2-7) 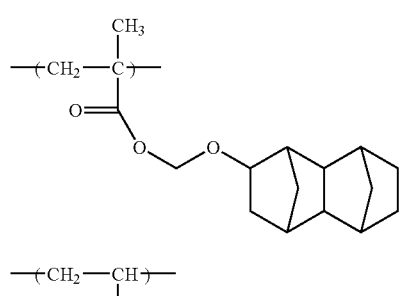
(a1-2-8) 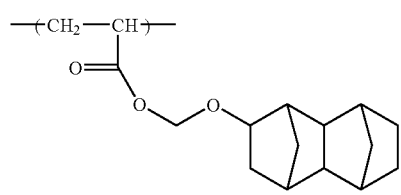
(a1-2-9) 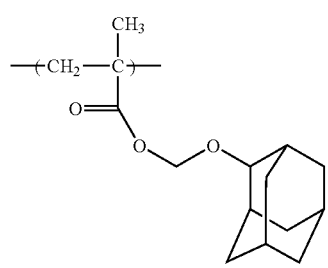
(a1-2-10) 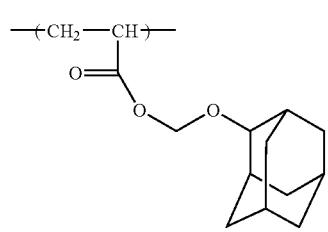
(a1-2-11) 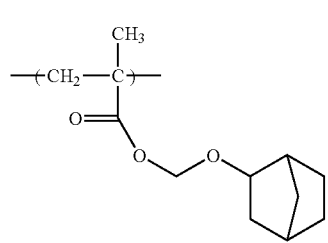
(a1-2-12) 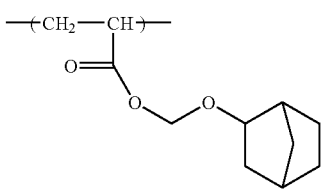
(a1-2-13) 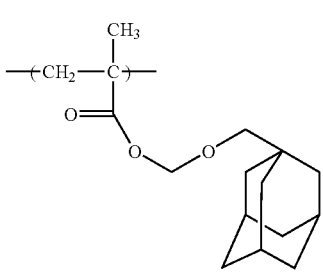
(a1-2-14) 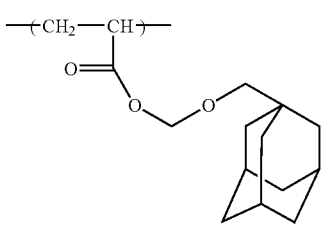
(a1-2-15) 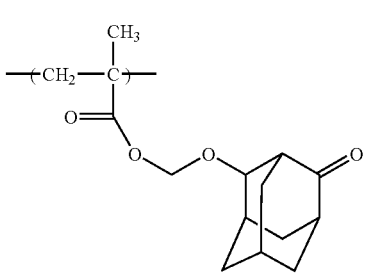
(a1-2-16) 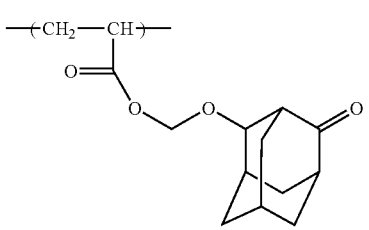
(a1-2-17) 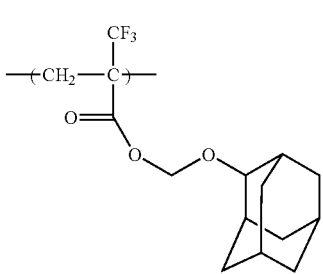

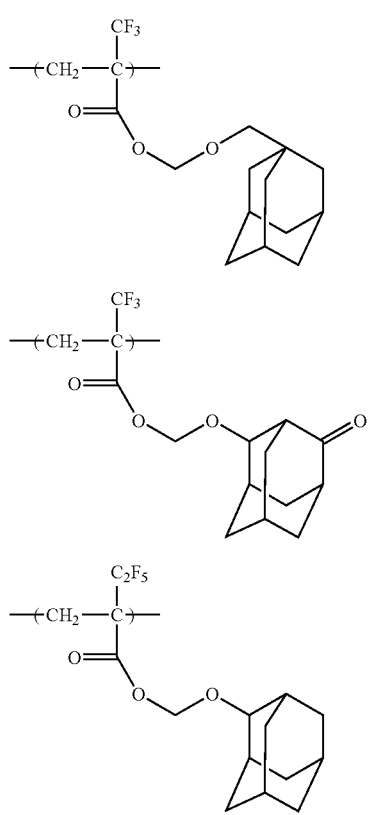
(a1-2-18)
(a1-2-19)
(a1-2-20)
[Chemical Formula 17]
(a1-2-21)
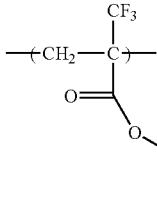
(a1-2-22)
(a1-2-23)
(a1-2-24)
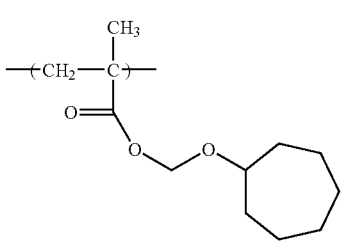
(a1-2-25)
(a1-2-26)
(a1-2-27)
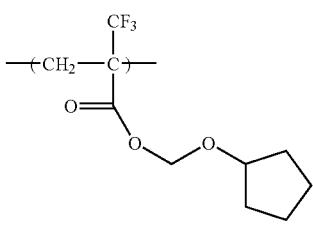
(a1-2-28)
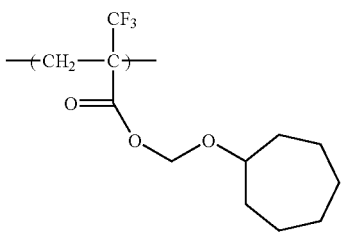
(a1-2-29)
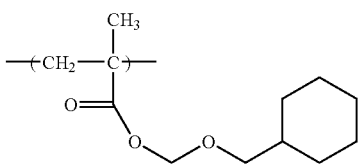
(a1-2-30)
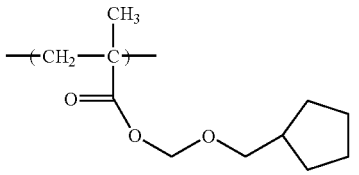
(a1-2-31)

[Chemical Formula 18]

(a1-2-32) (a1-2-33) (a1-2-34) (a1-2-35) (a1-2-36) (a1-2-37) (a1-2-38) (a1-2-39)

[Chemical Formula 19]

(a1-3-1) (a1-3-2)

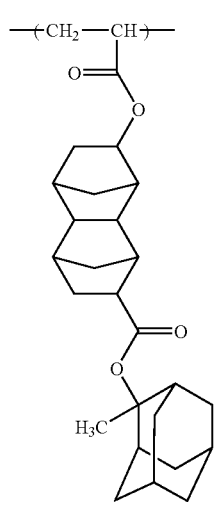 (a1-3-3)
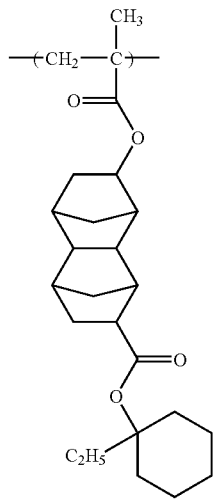 (a1-3-6)
(a1-3-4)
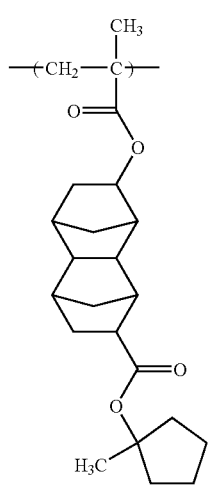 (a1-3-7)
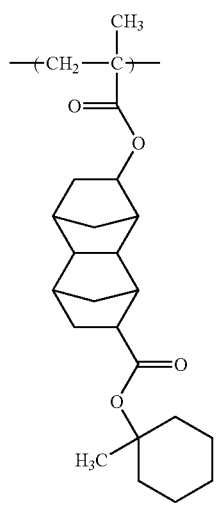 (a1-3-5)
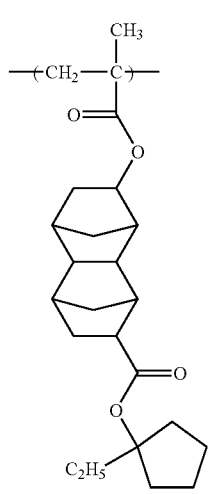 (a1-3-8)

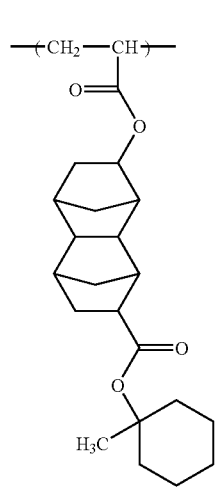
(a1-3-9)
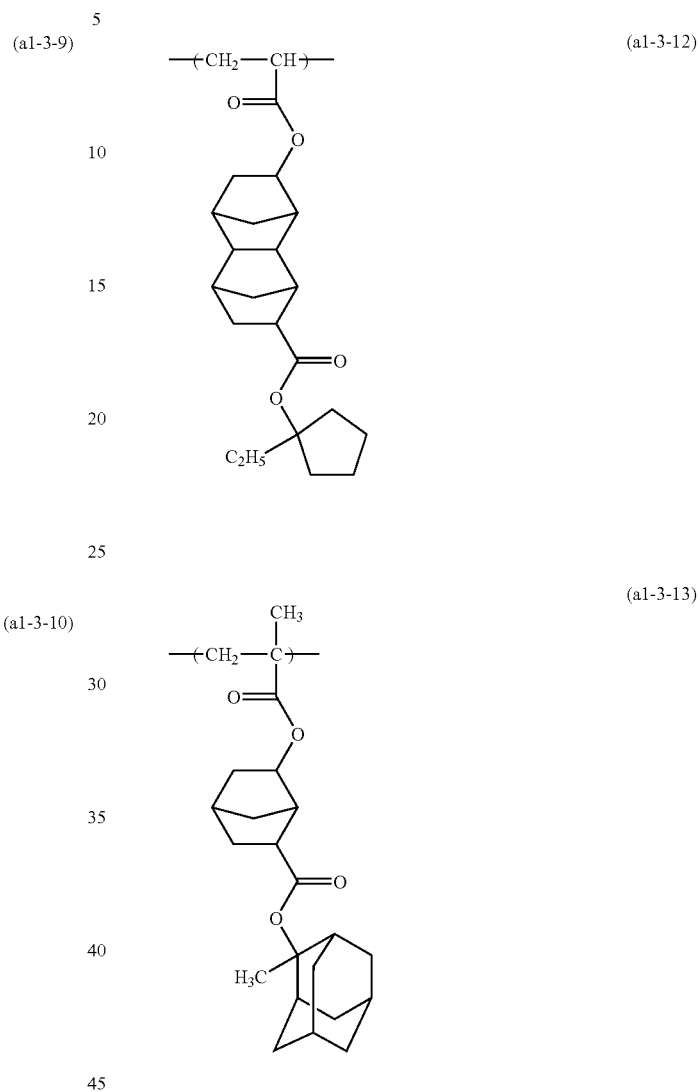
(a1-3-12)
(a1-3-10)
(a1-3-13)
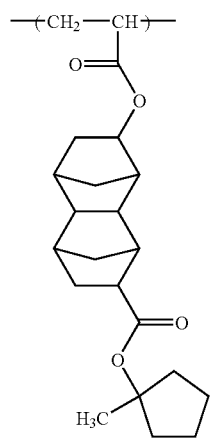
(a1-3-11)
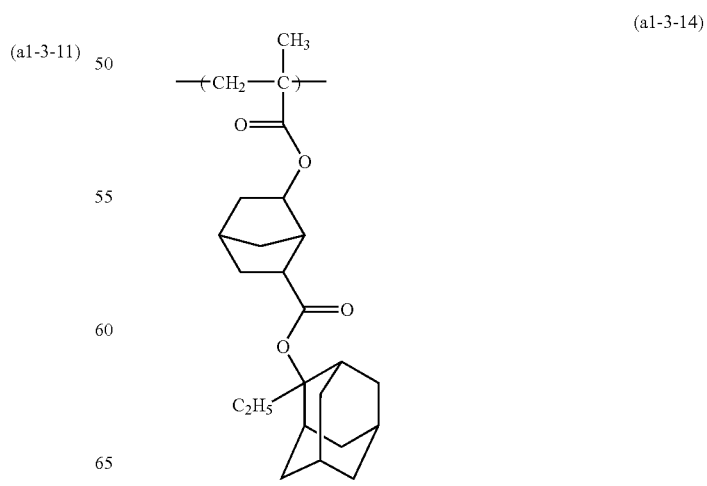
(a1-3-14)

(a1-3-15)
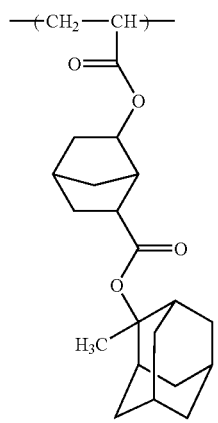
(a1-3-16)
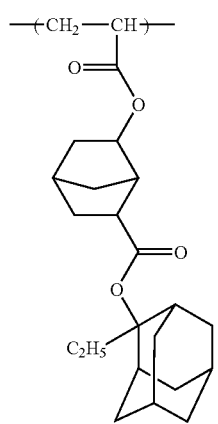
(a1-3-17)
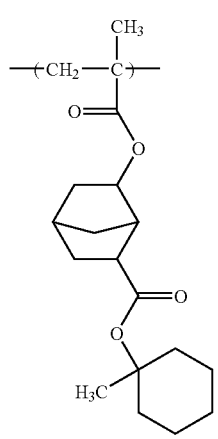
(a1-3-18)
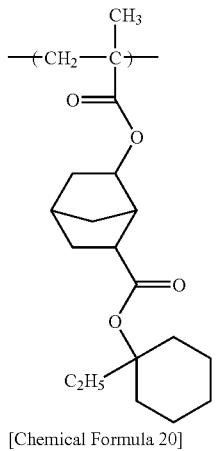
[Chemical Formula 20]
(a1-3-19)
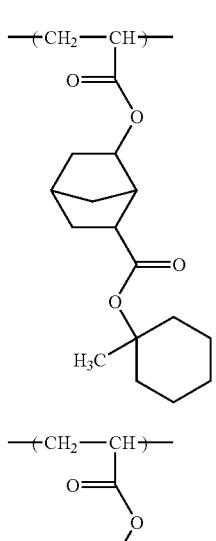
(a1-3-20)
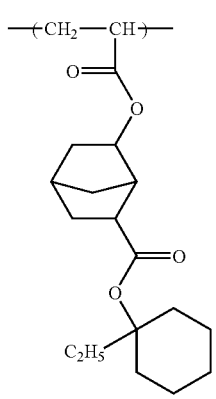
(a1-3-21)
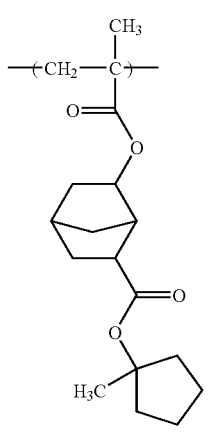

(a1-3-22) 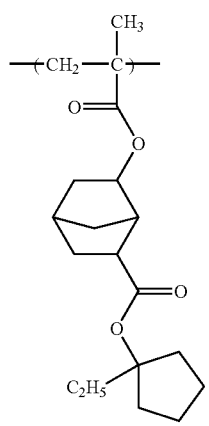
(a1-3-23) 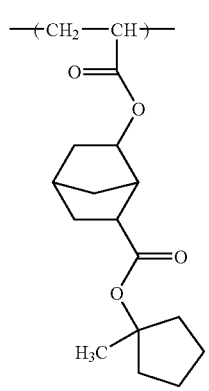
(a1-3-24) 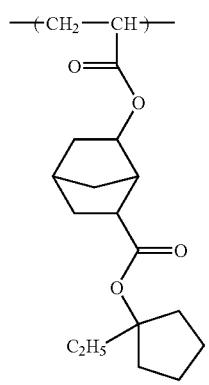
[Chemical Formula 21]
(a1-3-25) 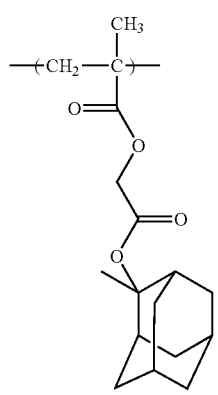
(a1-3-26) 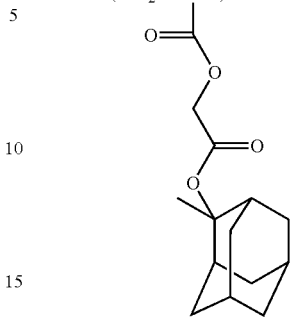
(a1-3-27) 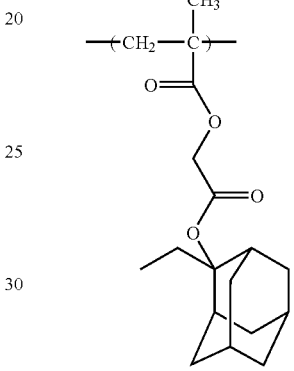
(a1-3-28) 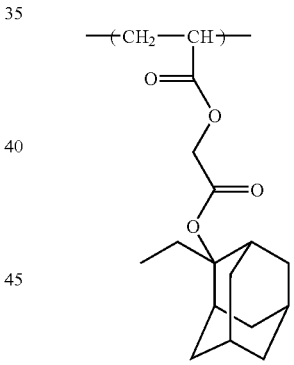
(a1-3-29) 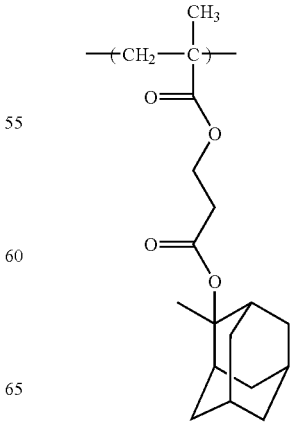

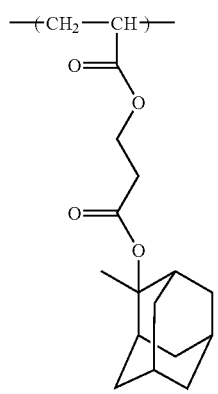 (a1-3-30)
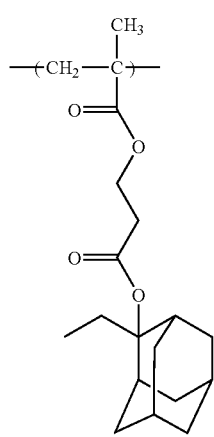 (a1-3-31)
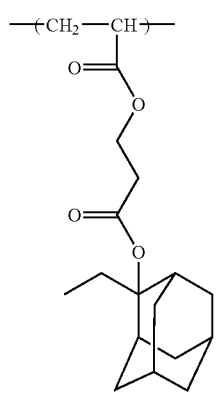 (a1-3-32)
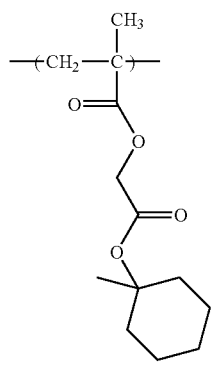 (a1-3-33)
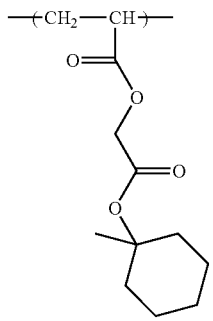 (a1-3-34)
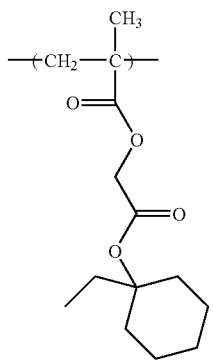 (a1-3-35)
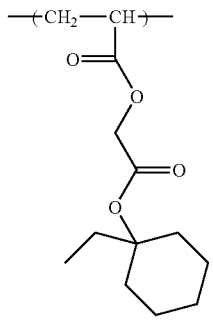 (a1-3-36)
[Chemical Formula 22]
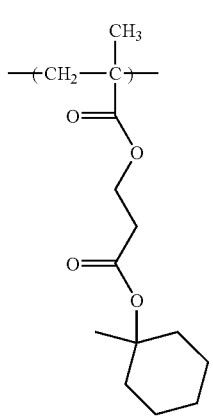 (a1-3-37)

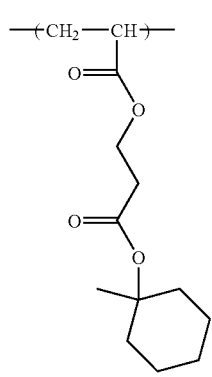 (a1-3-38)
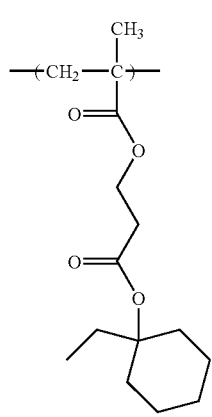 (a1-3-39)
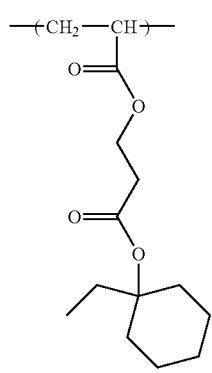 (a1-3-40)
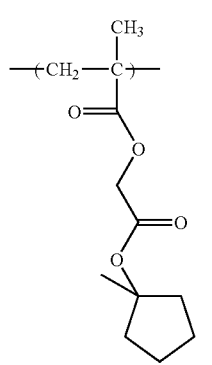 (a1-3-41)
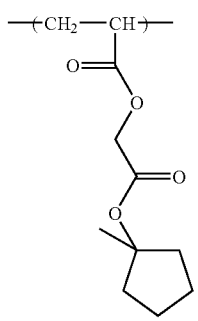 (a1-3-42)
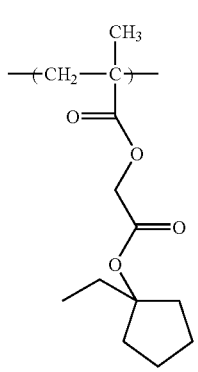 (a1-3-43)
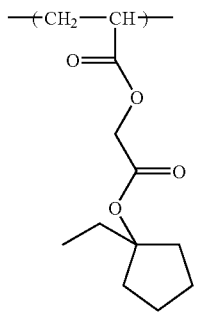 (a1-3-44)
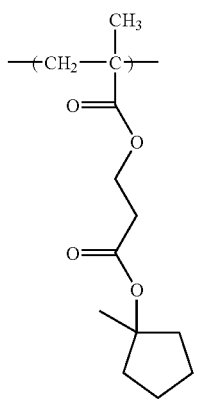 (a1-3-45)

(a1-3-46)
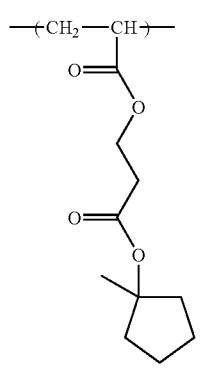
(a1-3-47)
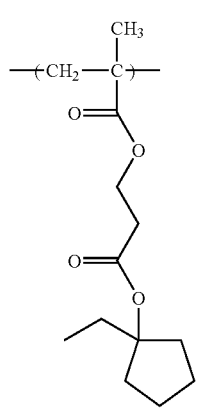
(a1-3-48)
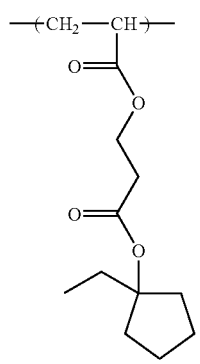
[Chemical Formula 23]
(a1-3-49)
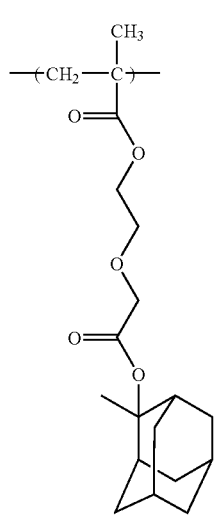
(a1-3-50)
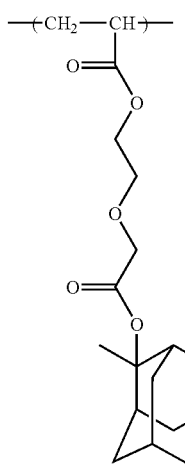
(a1-3-51)
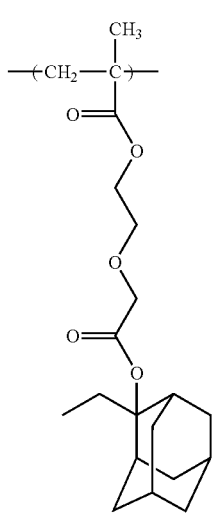
(a1-3-52)
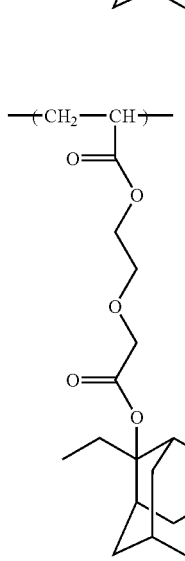

(a1-3-53)
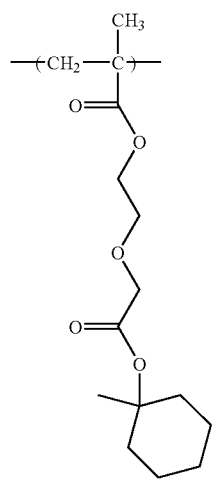
(a1-3-56)
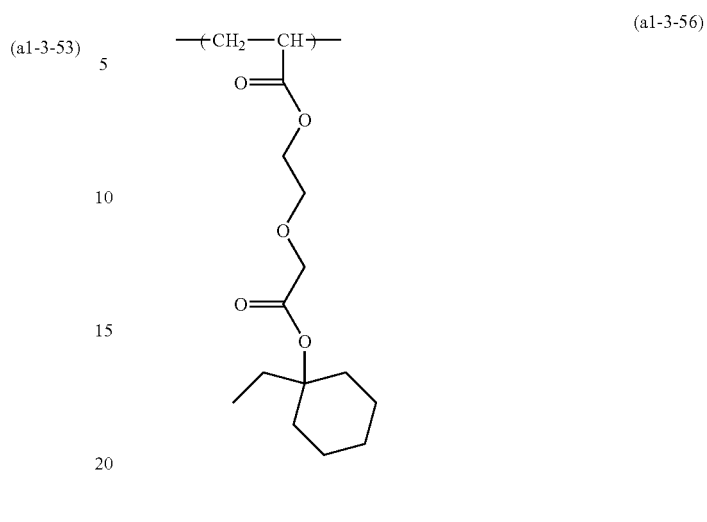
[Chemical Formula 24]
(a1-3-54)
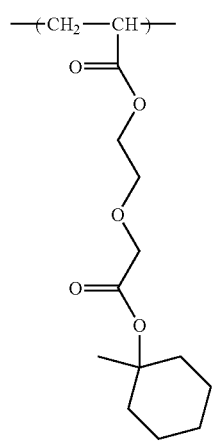
(a1-3-57)
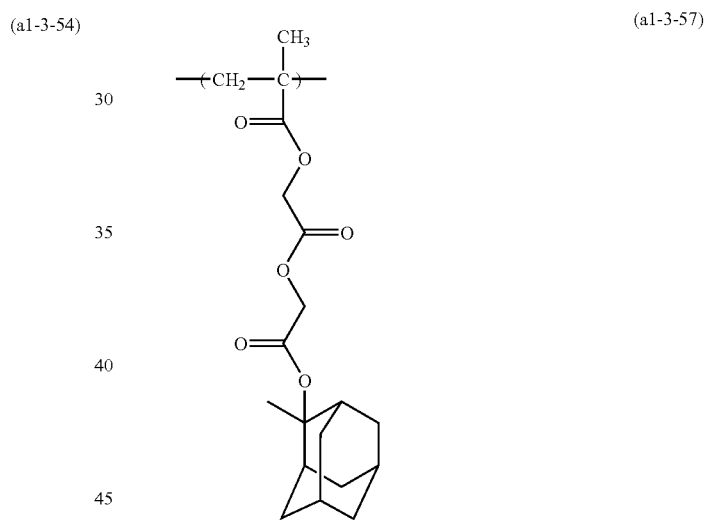
(a1-3-55)
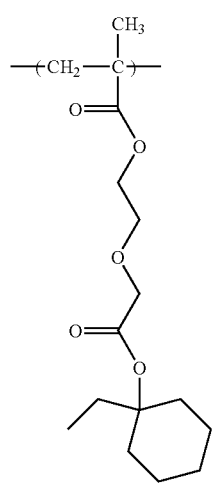
(a1-3-58)
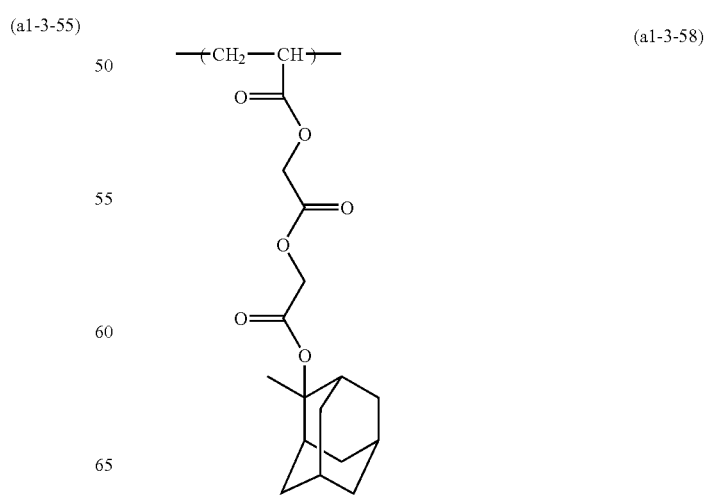

[Chemical Formula 25]
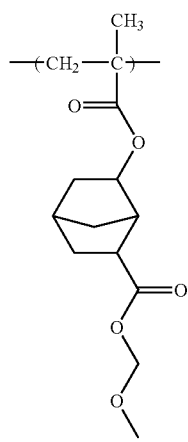 (a1-4-1)
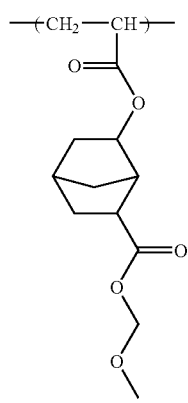 (a1-4-2)
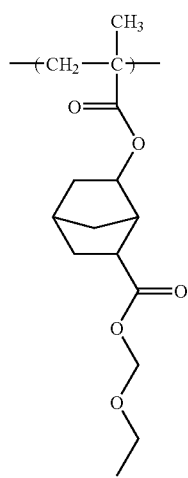 (a1-4-3)
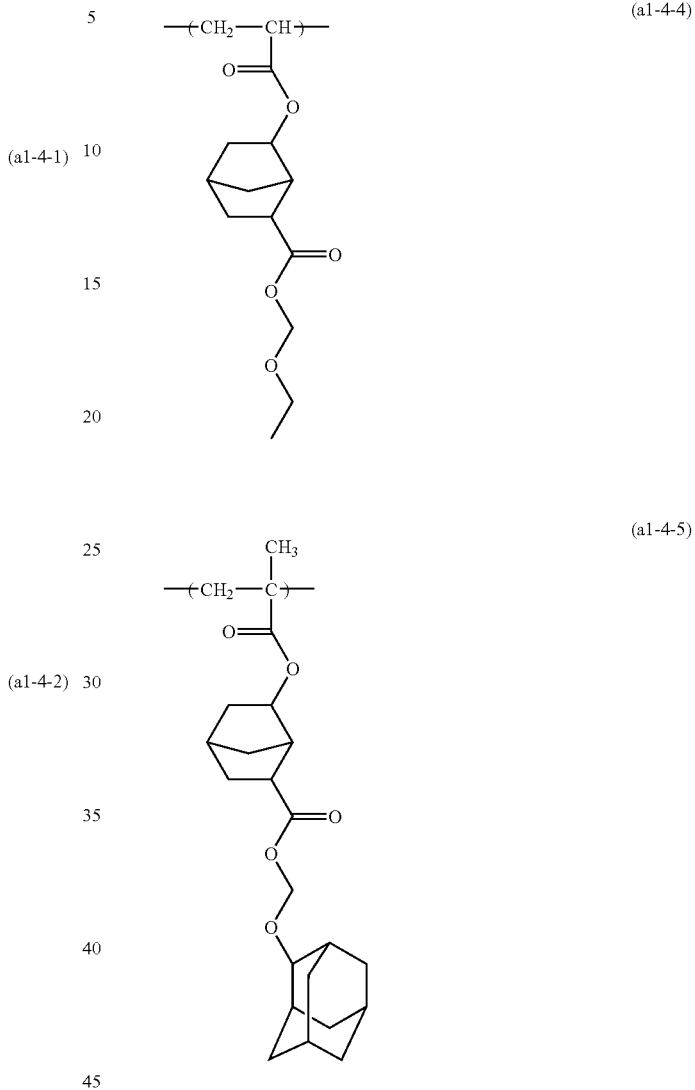
(a1-4-4)
(a1-4-5)
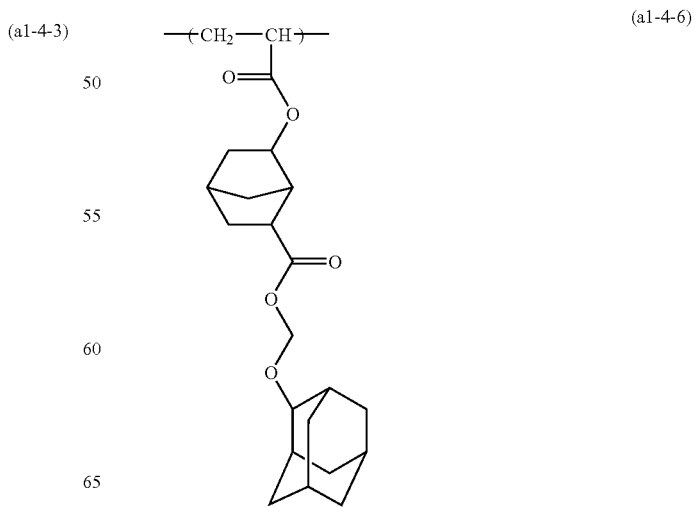 (a1-4-6)

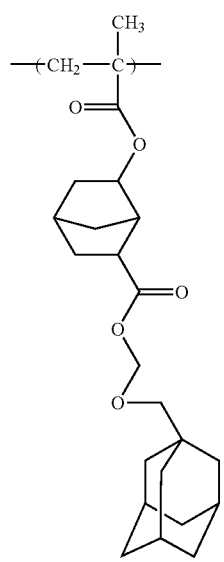 (a1-4-7)
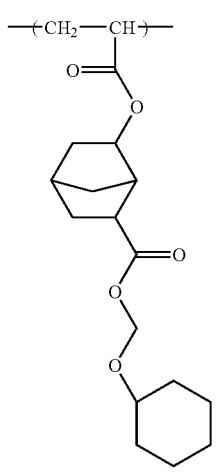 (a1-4-10)
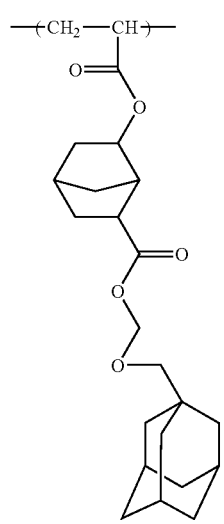 (a1-4-8)
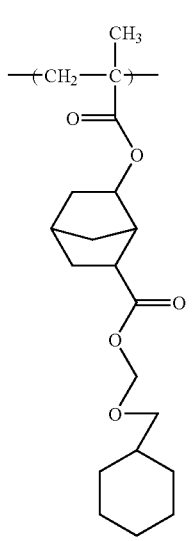 (a1-4-11)
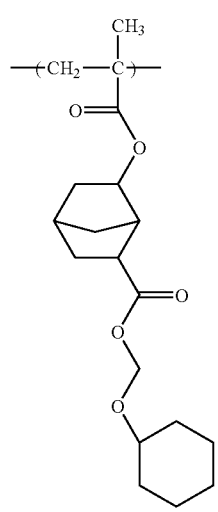 (a1-4-9)
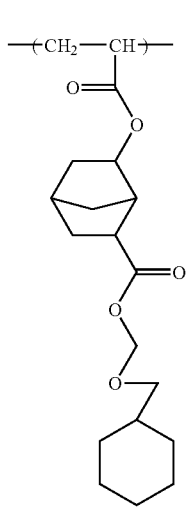 (a1-4-12)

(a1-4-13)
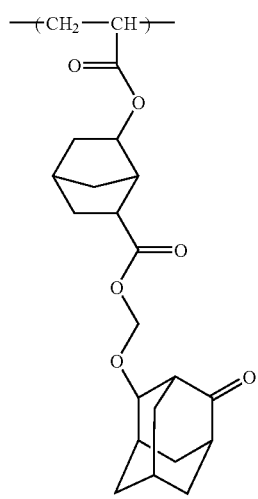
(a1-4-14)
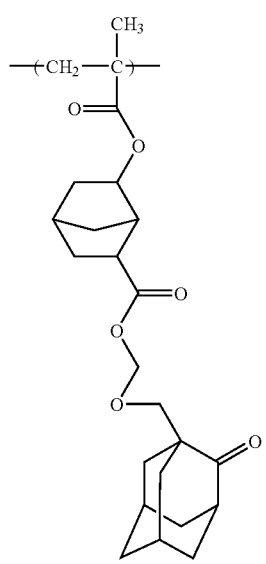
(a1-4-15)
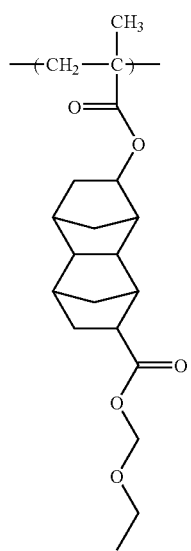
(a1-4-16)
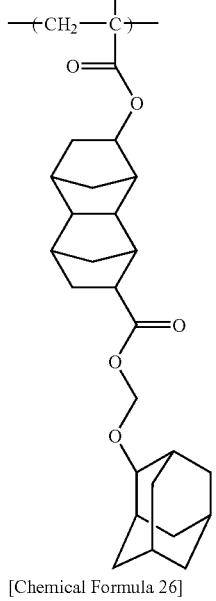
(a1-4-17)
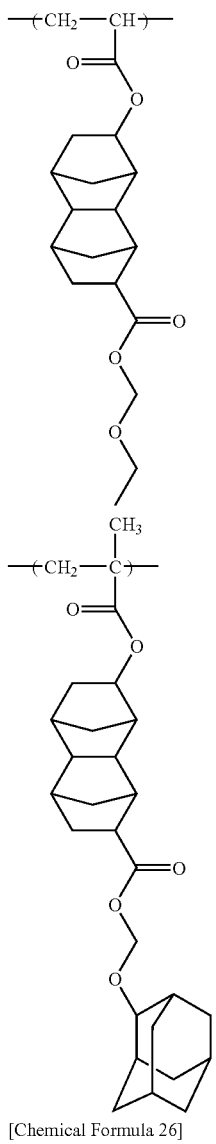
[Chemical Formula 26]
(a1-4-18)
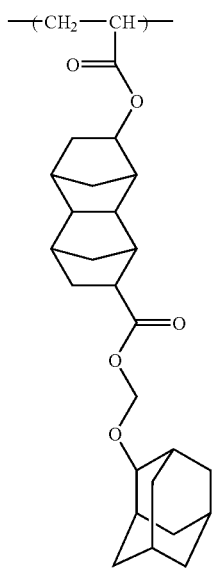

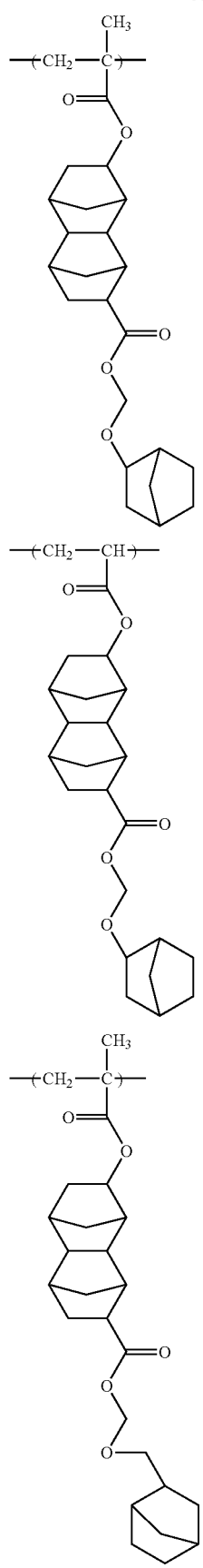
(a1-4-19)
(a1-4-20)
(a1-4-21)
(a1-4-22)
(a1-4-23)

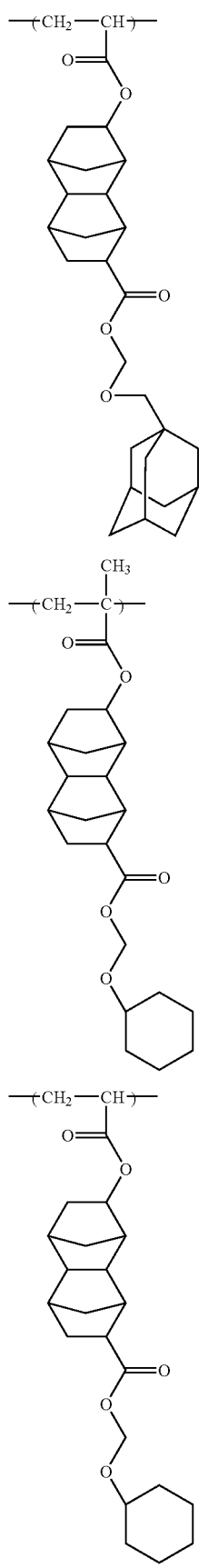
(a1-4-24)
(a1-4-25)
(a1-4-26)
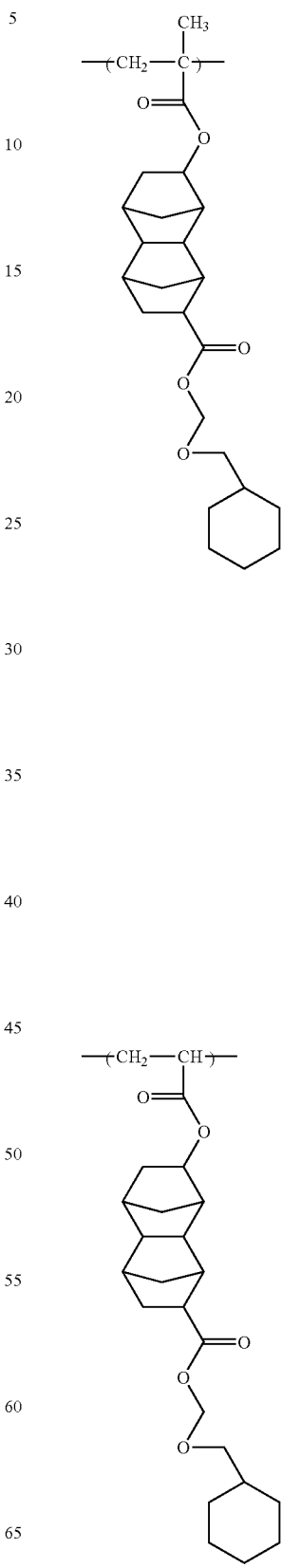
(a1-4-27)
(a1-4-28)

-continued

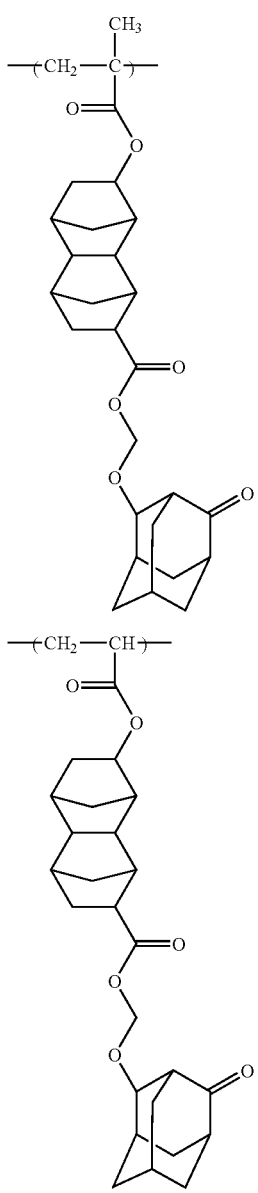

(a1-4-29)

(a1-4-30)

As the structural unit (a1), one type of structural unit may be used alone, or two or more types may be used in combination.

Among these, structural units represented by general formula (a1-1) or (a1-3) are preferable. More specifically, the use of at least one structural unit selected from the group consisting of structural units represented by formulas (a1-1-1) to (a-1-1-7), (a1-1-36) to (a1-1-42), (a1-1-47) to (a1-1-48), (a1-3-49) to (a1-3-56), and (a1-3-57) to (a1-3-58) is more preferable.

Further, as the structural unit (a1), structural units represented by general formula (a1-1-01) shown below, which includes the structural units represented by formulas (a1-1-1) to (a1-1-5), structural units represented by general formula (a1-1-02) shown below, which includes the structural units represented by formulas (a1-1-36) to (a1-1-42), structural units represented by general formula (a1-1-03) and general formula (a1-1-04) shown below, which includes the structural units represented by formulas (a1-1-47) to (a1-1-48), structural units represented by general formula (a1-3-01) and general formula (a1-3-02) shown below, which includes the structural units represented by formulas (a1-3-57) to (a1-3-58), structural units represented by general formula (a1-3-03) shown below, which includes the structural units represented by formulas (a1-3-49) to (a1-3-52), and structural units represented by general formula (a1-3-04) shown below, which includes the structural units represented by formulas (a1-3-53) to (a1-3-56) are also desirable.

[Chemical Formula 27]

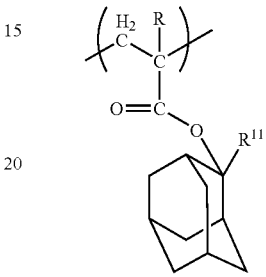

(a1-1-01)

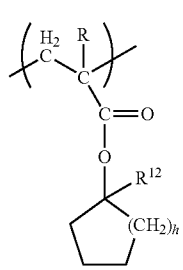

(a1-1-02)

In formula (a1-1-01), R represents a hydrogen atom, a lower alkyl group or a halogenated lower alkyl group, and $R^{11}$ represents a lower alkyl group. In formula (a1-1-02), R is as defined above, $R^{12}$ represents a lower alkyl group, and h represents an integer of 1 to 3.

In general formula (a1-1-01), R is as defined above, and examples thereof are as exemplified above.

The lower alkyl group for $R^{11}$ is the same as the lower alkyl group for R above, and examples thereof are as exemplified above, although a methyl group or an ethyl group is preferred.

In general formula (a1-1-02), R is as defined above, and examples thereof are as exemplified above.

The lower alkyl group for $R^{12}$ is the same as the lower alkyl group for R above, and examples thereof are as exemplified above, although a methyl group or an ethyl group is preferred, and an ethyl group is the most preferable. h is preferably 1 or 2, and is most preferably 2.

[Chemical Formula 28]

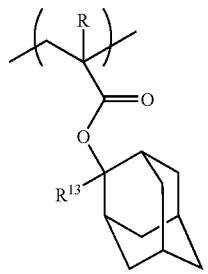

(a1-1-03)

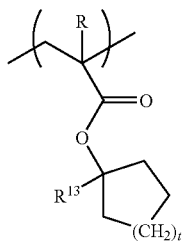
(a1-1-04)

In formula (a1-1-03), R is as defined above, and $R^{13}$ represents a branched alkyl group of 3 or more carbon atoms. In formula (a1-1-04), R and $R^{13}$ are as defined for R and $R^{13}$ in formula (a1-1-03), and t represents an integer of 0 to 3.

In general formula (a1-1-03), R is as defined above, and examples thereof are as exemplified above.

$R^{13}$ represents a branched alkyl group of 3 or more carbon atoms, and preferably 3 to 10 carbon atoms, and most preferably 3 to 5 carbon atoms. Specific examples of $R^{13}$ include an isopropyl group, isobutyl group, tert-butyl group, isopentyl group and neopentyl group, and of these, an isopropyl group is the most desirable.

In general formula (a1-1-04), R and $R^{13}$ are as defined for R and $R^{13}$ in formula (a1-1-03).

t represents an integer of 0 to 3, and is preferably either 1 or 2.

[Chemical Formula 29]

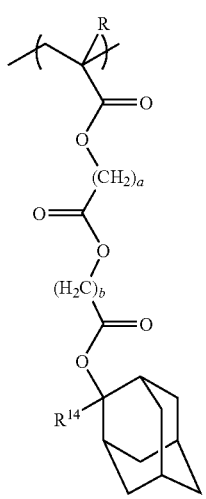
(a1-3-01)

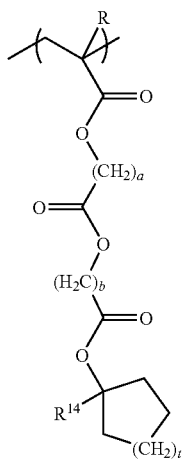
(a1-3-02)

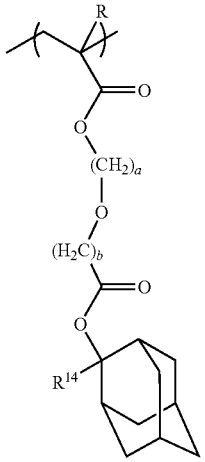
(a1-3-03)

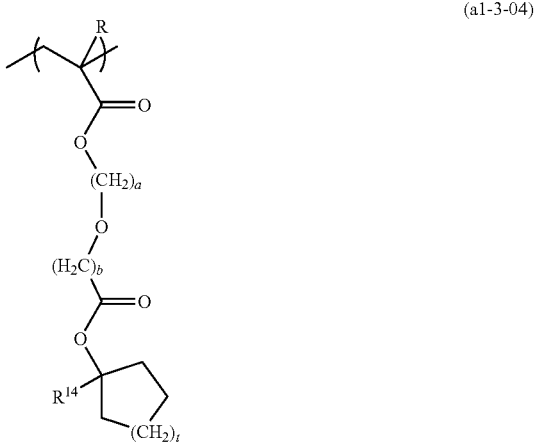
(a1-3-04)

In formula (a1-3-01), R is as defined above, $R^{14}$ represents a lower alkyl group, a represents an integer of 1 to 10, and b represents an integer of 1 to 10. In formula (a1-3-02), R, $R^{14}$, a and b are as defined for R, $R^{14}$, a and b in formula (a1-3-01), and t represents an integer of 0 to 3. In formula (a1-3-03), R, $R^{14}$, a and b are as defined for R, $R^{14}$, a and b in formula (a1-3-01). In formula (a1-3-04), R, $R^{14}$, a, b and t are as defined for R, $R^{14}$, a, b and t in formula (a1-3-02).

In general formula (a1-3-01) and general formula (a1-3-03), R is as defined above, and examples thereof are as exemplified above.

The lower alkyl group for $R^{14}$ is the same as the lower alkyl group for R above, and examples thereof are as exemplified above, although a methyl group or an ethyl group is preferred, and a methyl group is the most desirable.

a represents an integer of 1 to 10, preferably an integer of 1 to 5, and most preferably either 1 or 2.

b represents an integer of 1 to 10, preferably an integer of 1 to 5, and most preferably either 1 or 2.

In general formula (a1-3-02) and general formula (a1-3-04), R, $R^{14}$, a and b are as defined for R, $R^{14}$, a and b in general formula (a1-3-01).

t represents an integer of 0 to 3, and is preferably either 1 or 2.

The total amount of the structural unit (a1) within the component (A1), based on the combined total of all the structural units that constitute the component (A1), is preferably within a range from 10 to 80 mol %, more preferably from 20 to 70 mol %, and still more preferably from 25 to 60 mol %. By making the amount of the structural unit (a1) at least as large as the lower limit of the above-mentioned range, a pattern can be formed easily using a resist composition prepared from the component (A1). On the other hand, by ensuring that the amount of the structural unit (a1) is not more than the upper limit of the above-mentioned range, a good balance can be achieved with the other structural units.

In the component (A1), the proportion of structural units represented by general formula (a1-1-01) or general formula (a1-1-02), based on the combined total of all the structural units that constitute the component (A1), is preferably within a range from 10 to 80 mol %, more preferably from 15 to 70 mol %, and still more preferably from 15 to 50 mol %. By making this proportion at least as large as the lower limit of the above-mentioned range, a pattern can be formed easily using a resist composition prepared from the component (A1), whereas by ensuring that the proportion is not more than the upper limit of the above-mentioned range, a good balance can be achieved with the other structural units.

In the component (A1), the proportion of structural units represented by general formula (a1-1-03) or general formula (a1-1-04), based on the combined total of all the structural units that constitute the component (A1), is preferably within a range from 20 to 70 mol %, more preferably from 25 to 65 mol %, and still more preferably from 30 to 50 mol %. By making this proportion at least as large as the lower limit of the above-mentioned range, a pattern can be formed easily using a resist composition prepared from the component (A1), whereas by ensuring that the proportion is not more than the upper limit of the above-mentioned range, a good balance can be achieved with the other structural units.

In the component (A1), the proportion of structural units represented by general formulas (a1-3-01), (a1-3-02), (a1-3-03) or (a1-3-04), based on the combined total of all the structural units that constitute the component (A1), is preferably within a range from 5 to 50 mol %, more preferably from 5 to 30 mol %, and still more preferably from 5 to 25 mol %. By making this proportion at least as large as the lower limit of the above-mentioned range, a pattern can be formed easily using a resist composition prepared from the component (A1), whereas by ensuring that the proportion is not more than the upper limit of the above-mentioned range, a good balance can be achieved with the other structural units.

Monomers that yield the structural units represented by general formulas (a1-3-01) to (a1-3-04) (hereafter referred to jointly as "monomer W") can be produced, for example, using the production method described below.

Method of Producing Monomer W:

A compound represented by general formula (X-2) shown below (hereafter referred to as "compound (X-2)") is added, in the presence of a base, to a solution prepared by dissolving a compound represented by general formula (X-1) shown below (hereafter referred to as "compound (X-1)") in a reaction solvent, and the two compounds are then reacted to obtain a compound represented by general formula (X-3) shown below (hereafter referred to as "compound (X-3)"). Subsequently, a compound represented by general formula (X-4) shown below is added to a solution of the compound (X-3) in the presence of a base, and the compounds are then reacted to form the monomer W.

The compound (X-2) can be prepared, for example, by reacting $X^{11}$—B—C(=O)—OH and $X^2$—H. Further, the compounds $X^{11}$—B—C(=O)—OH and $X^2$—H may be used separately instead of using the compound (X-2).

Examples of bases that may be used include inorganic bases such as sodium hydride, $K_2CO_3$ and $Cs_2CO_3$, and organic bases such as triethylamine, 4-dimethylaminopyridine (DMAP) and pyridine.

The reaction solvent may be any solvent capable of dissolving the raw material compounds (X-1) and (X-2). Specific examples of the reaction solvent include tetrahydrofuran (THF), acetone, dimethylformamide (DMF), dimethylacetamide, dimethylsulfoxide (DMSO) and acetonitrile.

[Chemical Formula 30]

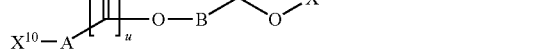

wherein R represents a hydrogen atom, a lower alkyl group or a halogenated lower alkyl group, A and B each independently represents a divalent hydrocarbon group that may have a substituent, $X^2$ represents an acid-dissociable, dissolution-inhibiting group, $X^{10}$ and $X^{12}$ each independently represents a hydroxyl group or a halogen atom, provided that one of $X^{10}$ and $X^{12}$ represents a hydroxyl group and the other represents a halogen atom, $X^{11}$ represents a halogen atom, and u represents either 0 or 1.

In the above formulas, R, $X^2$, A and B are each as defined above.

Examples of the halogen atom for $X^{10}$, $X^{11}$ and $X^{12}$ include a bromine atom, chlorine atom, iodine atom or fluorine atom.

As the halogen atom for $X^{10}$ or $X^{12}$, a chlorine atom or bromine atom is preferred, as it exhibits superior reactivity.

As the halogen atom for $X^{11}$, a bromine atom or chlorine atom is preferred, as it exhibits superior reactivity.

The above method of producing the monomer W represents a production method for monomers that yield the structural units represented by general formula (a1-3-01) or (a1-3-02) in those cases where u=1, and represents a production method for monomers that yield the structural units represented by general formula (a1-3-03) or (a1-3-04) in those cases where u=0.

Structural unit (a2)

The structural unit (a2) is a structural unit derived from an acrylate ester containing a lactone-containing cyclic group.

The term "lactone-containing cyclic group" refers to a cyclic group including one ring that includes a —O—C(O)— structure (the lactone ring). This lactone ring is counted as the first ring, so that a group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

There are no particular limitations on the structural unit (a2), and an arbitrary structural unit may be used.

Specific examples of lactone-containing monocyclic groups include groups in which one hydrogen atom has been removed from a monocyclic lactone such as γ-butyrolactone or mevalonic lactone. Further, examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 31]

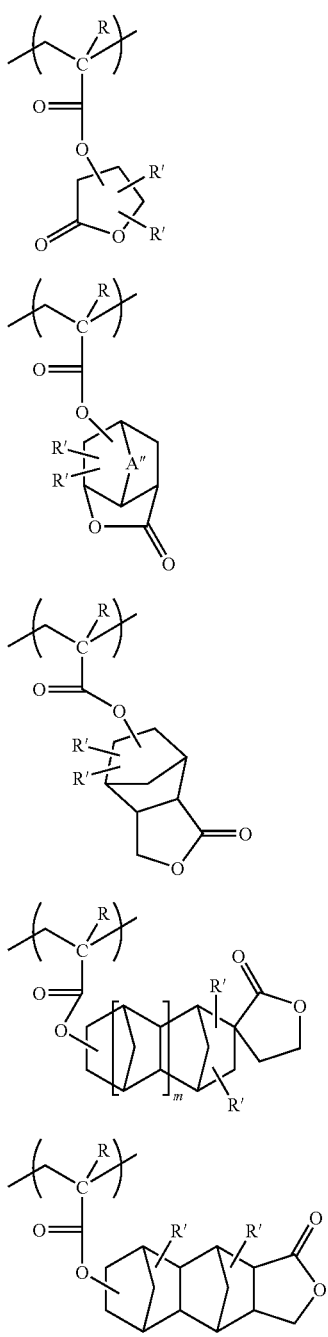

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents either 0 or 1; and A" represents an oxygen atom, a sulfur atom, or an alkylene group of 1 to 5 carbon atoms that may contain an oxygen atom or a sulfur atom.

In general formulas (a2-1) to (a2-5), R is as defined above for R in the structural unit (a1), and examples thereof are as exemplified above.

The lower alkyl group for R' is as defined for the lower alkyl group for R in the structural unit (a1).

When R" is a linear or branched alkyl group, it preferably has 1 to 10 carbon atoms, and more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from either a monocycloalkane such as cyclopentane or cyclohexane, or a polycycloalkane such as adamantane, norbornane, isobornane, tricyclodecane or tetracyclododecane.

In general formulas (a2-1) to (a2-5), if due consideration is given to factors such as industrial availability, then R' is most preferably a hydrogen atom.

Specific examples of the alkylene group of 1 to 5 carbon atoms that may contain an oxygen atom or a sulfur atom represented by A" include a methylene group, ethylene group, n-propylene group, isopropylene group, —O—CH$_2$—, —CH$_2$—O—CH$_2$—, —S—CH$_2$—, and —CH$_2$—S—CH$_2$—.

Specific examples of structural units represented by general formulas (a2-1) to (a2-5) above are shown below.

[Chemical Formula 32]

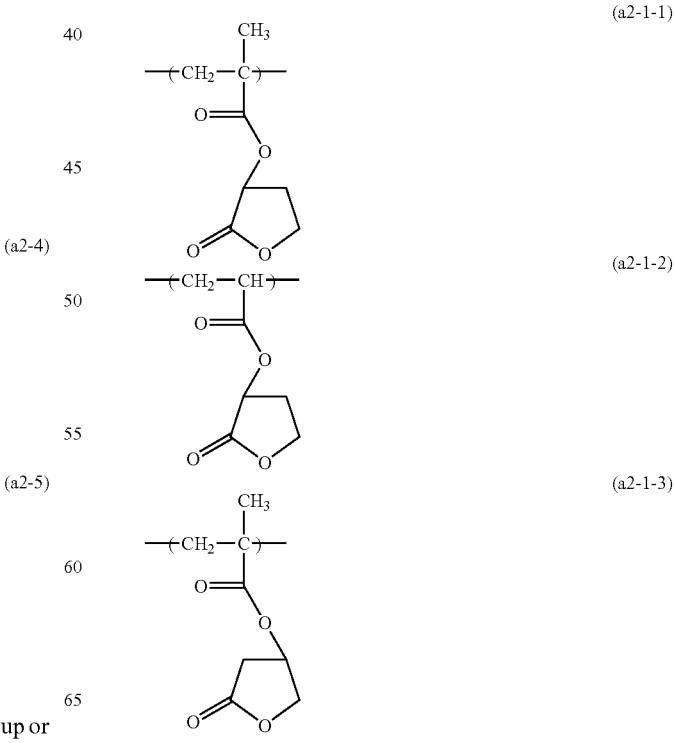

-continued
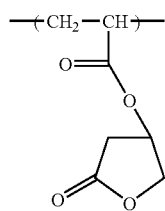 (a2-1-4)
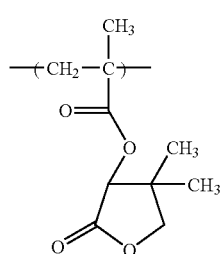 (a2-1-5)
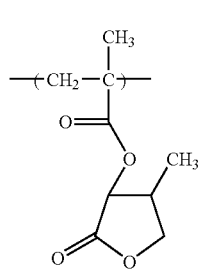 (A2-1-6)
[Chemical Formula 33]
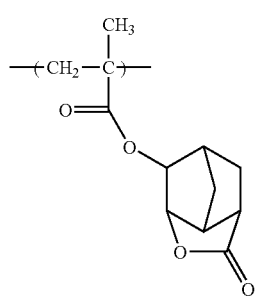 (a2-2-1)
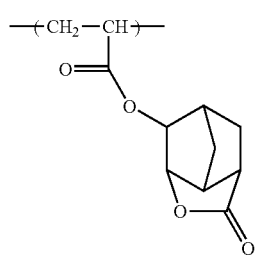 (a2-2-2)
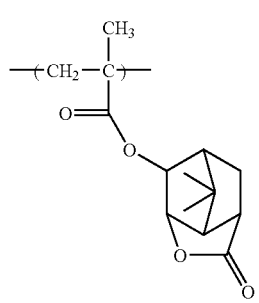 (a2-2-3)
-continued
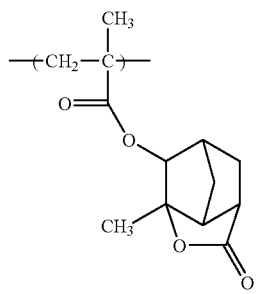 (a2-2-4)
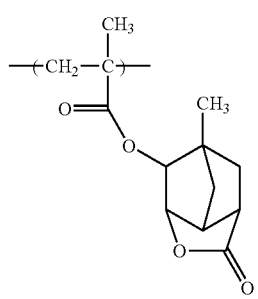 (a2-2-5)
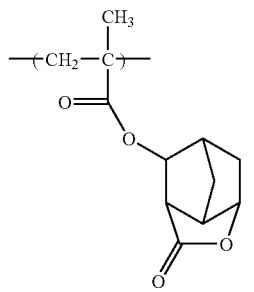 (a2-2-6)
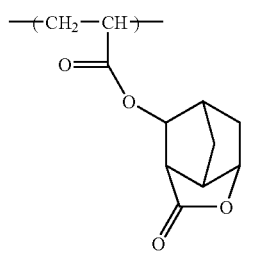 (a2-2-7)
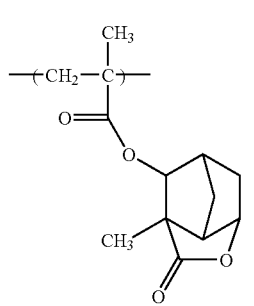 (a2-2-8)

(a2-2-9) 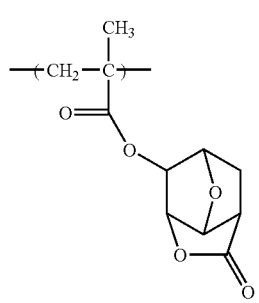
(a2-2-10) 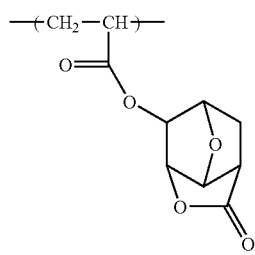
(a2-2-11) 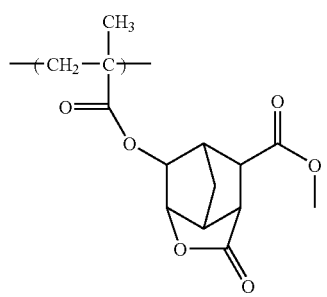
(a2-2-12) 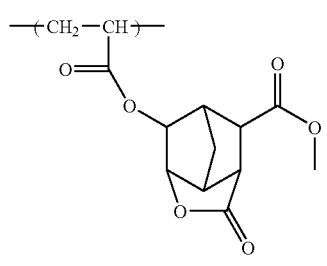
(a2-2-13) 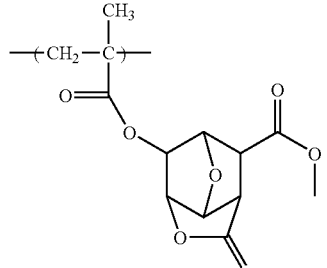
(a2-2-14) 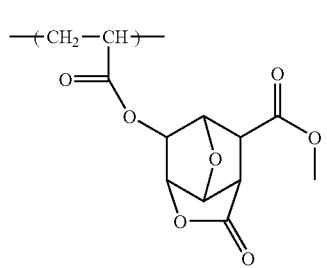
[Chemical Formula 34]
(a2-3-1) 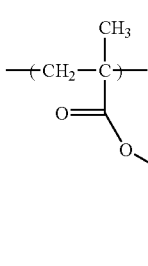
(a2-3-2) 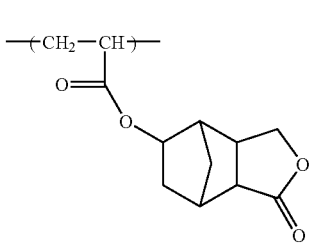
(a2-3-3) 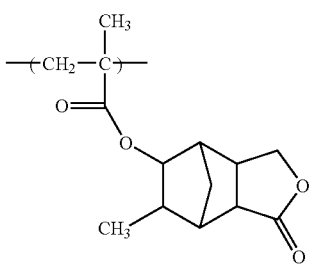
(a2-3-4) 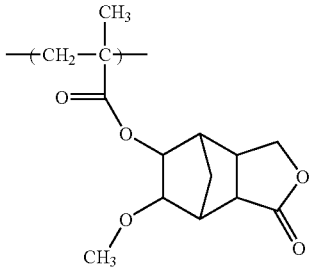
(a2-3-5) 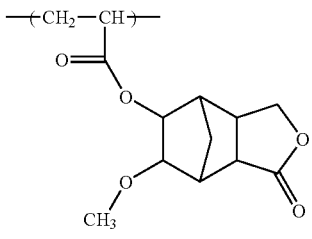
(a2-3-6) 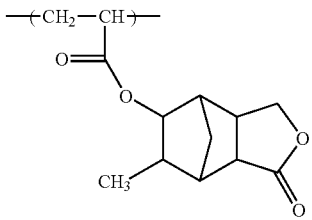

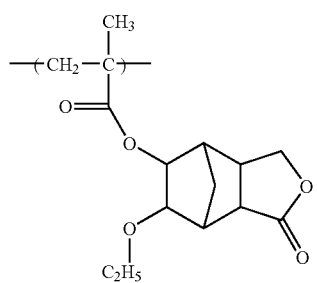
(a2-3-7)
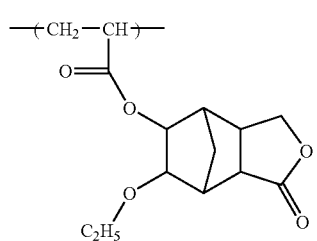
(a2-3-8)
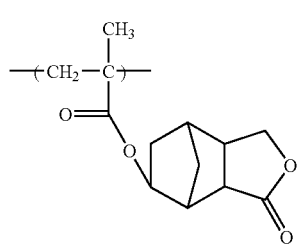
(a2-3-9)
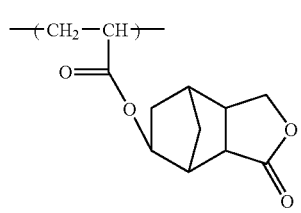
(a2-3-10)
[Chemical Formula 35]
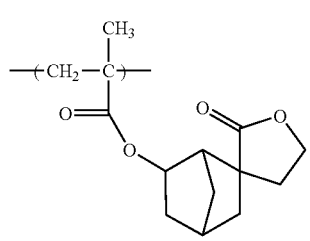
(a2-4-1)
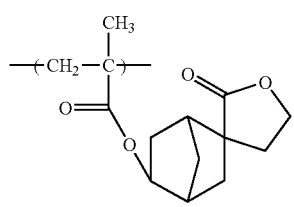
(a2-4-2)
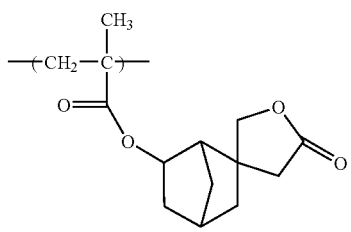
(a2-4-3)
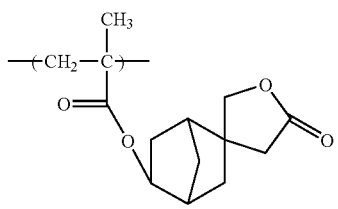
(a2-4-4)
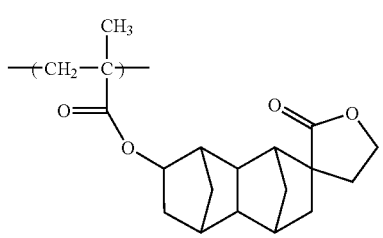
(a2-4-5)
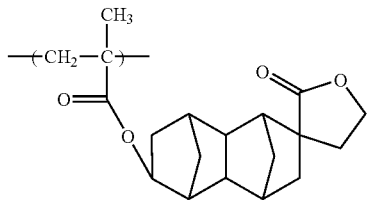
(a2-4-6)
(a2-4-7)
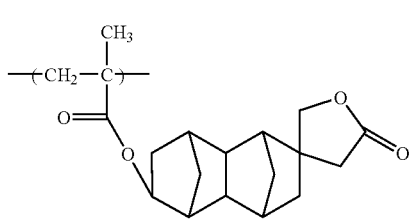
(a2-4-8)
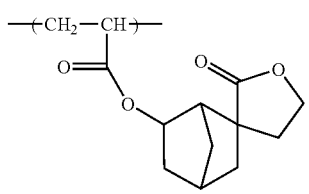
(a2-4-9)

(a2-4-10) 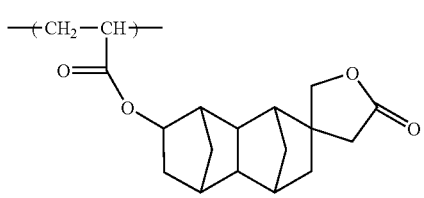

(a2-4-11) 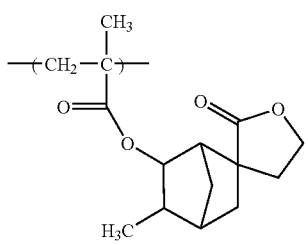

(a2-4-12) 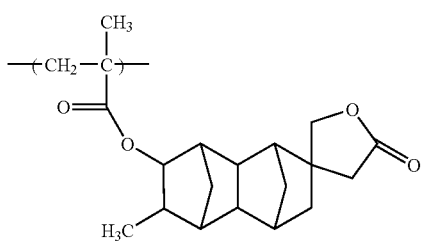

[Chemical Formula 36]

(a2-5-1) 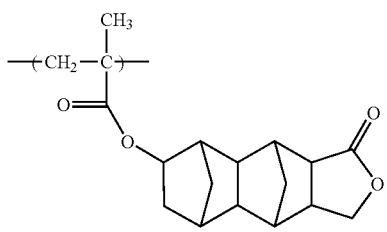

(a2-5-2) 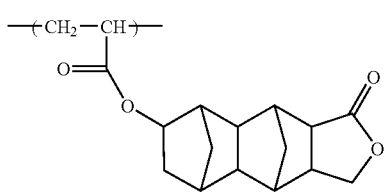

(a2-5-3) 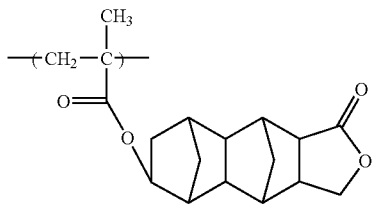

(a2-5-4) 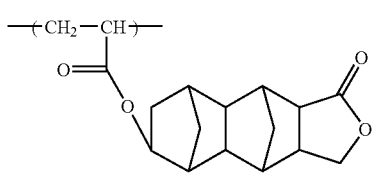

(a2-5-5) 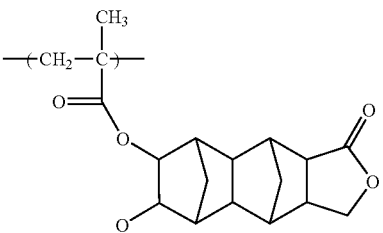

(a2-5-6) 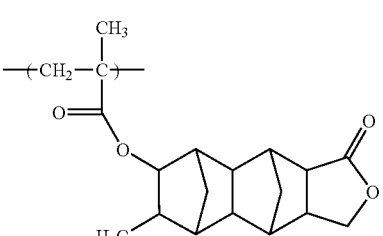

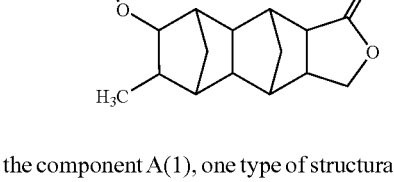

In the component A(1), one type of structural unit (a2) may be used, or two or more types may be used in combination.

As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of units represented by formulas (a2-1-1), (a2-1-2), (a2-2-1), (a2-2-2), (a2-2-9), (a2-2-10), (a2-3-1), (a2-3-2), (a2-3-9) and (a2-3-10).

In the component (A1), the amount of the structural unit (a2), based on the combined total of all the structural units that constitute the component (A1), is preferably within a range from 5 to 60 mol %, more preferably from 10 to 55 mol %, and still more preferably from 20 to 55 mol %. By making the amount of the structural unit (a2) at least as large as the lower limit of the above-mentioned range, the effect of using the structural unit (a2) can be satisfactorily achieved, whereas by ensuring that the amount is not more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane, or tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), (a3-3) and (a3-4) shown below are preferable.

[Chemical Formula 37]

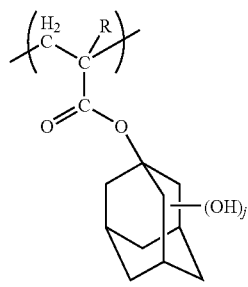
(a3-1)

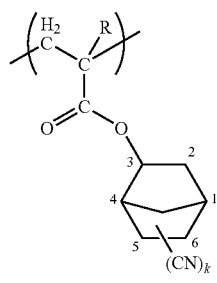
(a3-2)

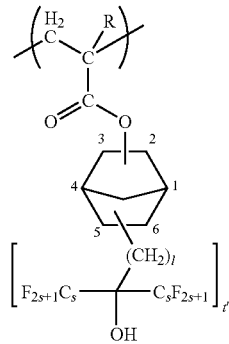
(a3-3)

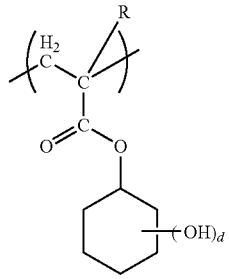
(a3-4)

wherein R is as defined above, j represents an integer of 1 to 3, k represents an integer of 1 to 3, t' represents an integer of 1 to 3, l represents an integer of 1 to 5, s represents an integer of 1 to 3, and d represents an integer of 1 to 3.

In formula (a3-1), j is preferably 1 or 2, and is more preferably 1. When j is 2, it is preferable that the hydroxyl groups are bonded to the 3rd and 5th positions of the adamantyl group. When j is 1, it is preferable that the hydroxyl group is bonded to the 3rd position of the adamantyl group.

j is preferably 1, and it is particularly desirable that the hydroxyl group is bonded to the 3rd position of the adamantyl group.

In formula (a3-2), k is preferably 1. The cyano group is preferably bonded to the 5th or 6th position of the norbornyl group.

In formula (a3-3), t' is preferably 1, l is preferably 1, and s is preferably 1. Further, in formula (a3-3), it is preferable that a 2-norbornyl group or 3-norbornyl group is bonded to the terminal of the carboxyl group of the acrylic acid. The fluorinated alkyl alcohol is preferably bonded to the 5th or 6th position of the norbornyl group.

In formula (a3-4), d is preferably 1 or 2, and is most preferably 1. Although there are no particular limitations on the bonding position of the hydroxyl group, when d is 1, the hydroxyl group is preferably bonded to the 2nd position in terms of ease of availability and cost. When d is 2 or 3, any combination of bonding positions may be employed.

In the component (A1), as the structural unit (a3), one type of structural unit may be used, or two or more types may be used in combination.

When the component (A1) contains the structural unit (a3), the amount of the structural unit (a3), based on the combined total of all the structural units that constitute the component (A1), is preferably within a range from 5 to 50 mol %, more preferably from 5 to 40 mol %, and still more preferably 5 to 25 mol %. By making the amount of the structural unit (a3) at least as large as the lower limit of the above-mentioned range, the effect of using the structural unit (a3) can be satisfactorily achieved, whereas by ensuring that the amount is not more than the upper limit of the above-mentioned range, a good balance can be achieved with the other structural units.

Structural Unit (a4)

The component (A1) may also include a structural unit (a4) which is other than the above-mentioned structural units (a1) to (a3), as long as the effects of the present invention are not impaired.

As the structural unit (a4), any other structural unit that cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit that contains a non-acid-dissociable aliphatic polycyclic group and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 38]

(a4-1)
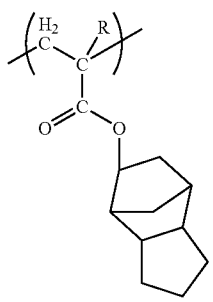

(a4-2)
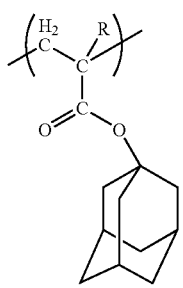

(a4-3)
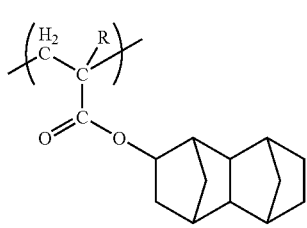

(a4-4)
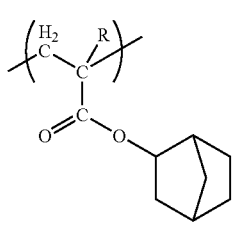

(a4-5)
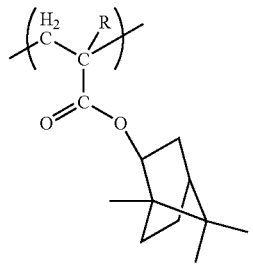

wherein R is as defined above.

When the structural unit (a4) is included in the component (A1), the amount of the structural unit (a4), based on the combined total of all the structural units that constitute the component (A1), is preferably within the range from 1 to 30 mol %, and more preferably from 10 to 20 mol %.

In the present invention, the component (A1) is preferably a polymer containing the structural unit (a1), and examples of that polymer include copolymers consisting of the structural units (a1) and (a2), copolymers consisting of the structural units (a1) and (a3), copolymers consisting of the structural units (a1), (a2) and (a3), and copolymers consisting of the structural units (a1), (a2), (a3) and (a4).

In the component (A), one type of the component (A1) may be used, or a combination of two or more types may be used.

In the present invention, as the component (A1), materials containing a combination of structural units shown below are particularly preferred.

[Chemical Formula 39]

(A1-11)
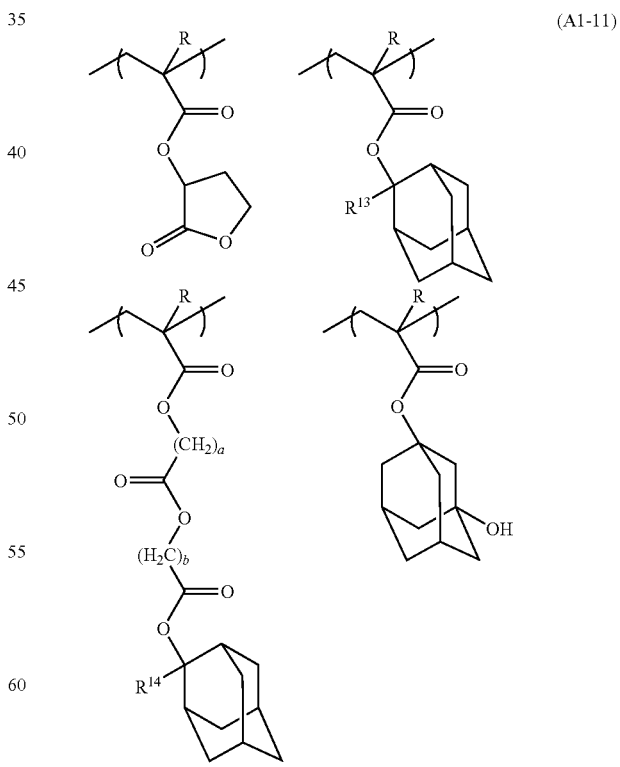

In the above general formula (A1-11), R is as defined above, and the plurality of R groups may be the same or different. $R^{13}$, $R^{14}$, a and b are each as defined above.

In the general formula (A1-11), the branched alkyl group of 3 or more carbon atoms for $R^{13}$ is most preferably an isopropyl group.

The lower alkyl group for $R^{14}$ is preferably a methyl group or ethyl group, and is most preferably a methyl group.

a represents an integer of 1 to 10, is preferably either 1 or 2, and is most preferably 1.

b represents an integer of 1 to 10, is preferably either 1 or 2, and is most preferably 1.

Further, as the component (A1), materials containing a combination of structural units shown below are also particularly desirable.

[Chemical Formula 40]

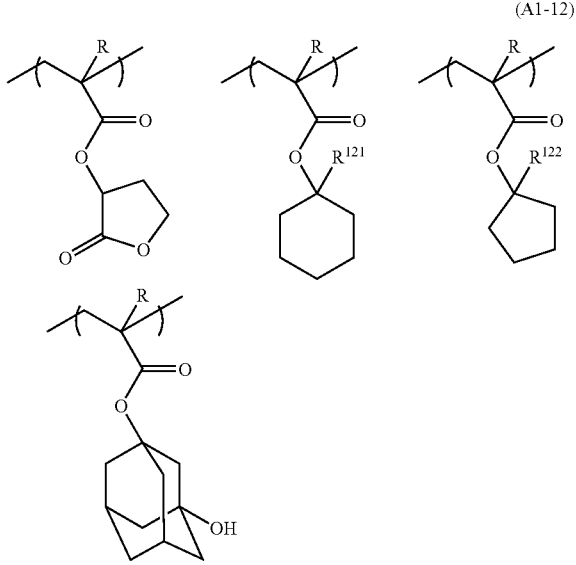

(A1-12)

In the above general formula (a1-12), R is as defined above, and the plurality of R groups may be the same or different.

$R^{121}$ represents a lower alkyl group, and is as defined above for the lower alkyl group for $R^{12}$. Examples thereof are as exemplified above, although a methyl group or ethyl group is preferred, and an ethyl group is the most preferable.

$R^{122}$ represents a lower alkyl group, and is as defined above for the lower alkyl group for $R^{12}$. Examples thereof are as exemplified above, although a methyl group or ethyl group is preferred, and a methyl group is the most preferable.

The component (A1) can be obtained, for example, by a conventional radical polymerization or the like of the monomers corresponding with each of the structural units, using a radical polymerization initiator such as azobisisobutyronitrile (AIBN) or dimethyl azobisisobutyrate.

Furthermore, in the component (A1), by using a chain transfer agent such as $HS—CH_2—CH_2—CH_2—C(CF_3)_2—OH$, a $—C(CF_3)_2—OH$ group can be introduced at the terminals of the component (A1). Such a copolymer having an introduced hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably within a range from 2,000 to 50,000, more preferably from 3,000 to 30,000, and most preferably from 5,000 to 20,000. By making the weight average molecular weight not more than the upper limit of the above-mentioned range, the component (A1) exhibits satisfactory solubility in a resist solvent when used as a resist, whereas by ensuring that the weight average molecular weight is at least as large as the lower limit of the above-mentioned range, dry etching resistance and the cross-sectional shape of the resist pattern are more favorable.

Further, the dispersity (Mw/Mn) is preferably within a range from 1.0 to 5.0, more preferably from 1.0 to 3.0, and most preferably from 1.2 to 2.5. Here, Mn is the number average molecular weight.

[Component (A2)]

As the component (A2), it is preferable to use a compound which has a molecular weight of at least 500 and less than 2,000, contains a hydrophilic group, and also contains an acid-dissociable, dissolution-inhibiting group exemplified above in connection with the component (A1). Specific examples include compounds containing a plurality of phenol skeletons in which some of the hydrogen atoms within hydroxyl groups have been substituted with the aforementioned acid-dissociable, dissolution-inhibiting groups.

Examples of the component (A2) include low molecular weight phenolic compounds in which a portion of the hydroxyl group hydrogen atoms have been substituted with an aforementioned acid-dissociable, dissolution-inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl) isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid-dissociable, dissolution-inhibiting group, and suitable examples include the groups described above.

As the component (A), one type may be used, or two or more types may be used in combination.

Of the above possibilities, the component (A) preferably includes the component (A1).

In the resist composition of the present invention, the amount of the component (A) can be appropriately adjusted depending on factors such as the thickness of the resist film to be formed.

<Component (B)>

In the present invention, the component (B) includes an acid generator (B1) (hereafter, referred to as "component (B1)") consisting of a compound represented by general formula (b1) shown below.

[Chemical Formula 41]

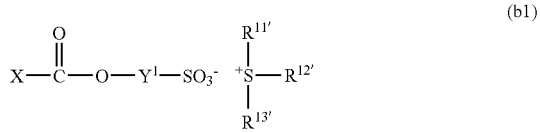

(b1)

wherein $Y^1$ represents a fluorinated alkylene group of 1 to 4 carbon atoms that may have a substituent, X represents an aliphatic cyclic group of 3 to 30 carbon atoms that may have a substituent, $R^{11'}$ to $R^{13'}$ each independently represents an aryl group or alkyl group that may have a substituent, provided that at least one of $R^{11'}$ to $R^{13'}$ is an aryl group having a substituent represented by general formula (b1-0) shown below, and two alkyl groups among $R^{11'}$ to $R^{13'}$ may be bonded to each other to form a ring with the sulfur atom in the formula.

[Chemical Formula 42]

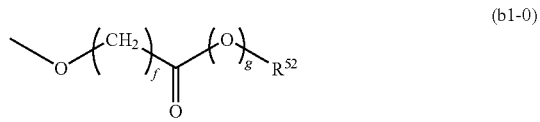

(b1-0)

wherein $R^{52}$ represents a chain-like or cyclic hydrocarbon group, f represents 0 or 1, and g represents 0 or 1.

Anion Moiety of Component (B1)

In the above formula (b1), $Y^1$ represents a fluorinated alkylene group of 1 to 4 carbon atoms that may have a substituent.

Examples of the fluorinated alkylene group for $Y^1$ include groups in which some or all of the hydrogen atoms of an alkylene group have been substituted with fluorine atoms.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, and —$C(CF_3)_2CH_2$—.

As $Y^1$, fluorinated alkylene groups in which the carbon atom bonded to the adjacent sulfur atom is fluorinated are particularly desirable. If the carbon atom bonded to the sulfur atom adjacent to $Y^1$ is fluorinated, then the acid generated from the component (B) upon irradiation exhibits a more powerful acid strength. As a result, a more favorable resist pattern shape is obtained, and the lithography properties are further improved.

Examples of this type of fluorinated alkylene group include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these groups, —$CF_2$—, —$CF_2CF_2$—, —$CF_2CF_2CF_2$—, —$CH_2CF_2$— or $CH_2CF_2CF_2$— is preferred, —$CF_2$—, —$CF_2CF_2$—, —$CF_2CF_2CF_2$— or —$CH_2CF_2$— is more preferable, and —$CH_2CF_2$— is particularly desirable.

The fluorinated alkylene group for $Y^1$ may have a substituent.

The expression that the fluorinated alkylene group "may have a substituent" means that some or all of the hydrogen atoms or fluorine atoms within the fluorinated alkylene group may be substituted with an atom other than a hydrogen atom or fluorine atom, or with a group.

Examples of the substituent with which the fluorinated alkylene group may be substituted include an alkyl group of 1 to 4 carbon atoms, an alkoxy group of 1 to 4 carbon atoms, and a hydroxyl group.

In formula (b1), X represents an aliphatic cyclic group of 3 to 30 carbon atoms that may have a substituent.

In the aliphatic cyclic group X, some of the carbon atoms that constitute the aliphatic cyclic group may be substituted with a substituent that contains a hetero atom, and some or all of the hydrogen atoms that constitute the aliphatic cyclic group may also be substituted with substituents that contain a hetero atom.

There are no particular limitations on this "hetero atom" within the group X as long as it is an atom other than a carbon atom or hydrogen atom, and examples include a halogen atom, oxygen atom, sulfur atom or nitrogen atom. Examples of the halogen atom include a fluorine atom, chlorine atom, iodine atom and bromine atom.

The substituent that contains a hetero atom may be composed solely of the hetero atom, or may be a group that includes a group or atom(s) other than the hetero atom.

Specific examples of the substituent that may substitute some of the carbon atoms include —O—, —C(=O)—O—, —C(=O)—, —O—C(=O)—O—, —C(=O)—NH—, —NH— (wherein the H may be substituted with a substituent such as an alkyl group or acyl group), —S—, —S(=O)$_2$—, and —S(=O)$_2$—O—. These substituents may be included within the cyclic structure.

Specific examples of the substituent containing a hetero atom that may substitute some or all of the hydrogen atoms include an alkoxy group, halogen atom, halogenated alkyl group, hydroxyl group, oxygen atom (=O), and cyano group.

The alkoxy group is preferably an alkoxy group of 1 to 5 carbon atoms, is more preferably a methoxy group, ethoxy group, n-propoxy group, iso-propoxy group, n-butoxy group or tert-butoxy group, and is most preferably a methoxy group or ethoxy group.

Examples of the halogen atom include a fluorine atom, chlorine atom, bromine atom or iodine atom, and a fluorine atom is preferred.

Examples of the halogenated alkyl group include groups in which some or all of the hydrogen atoms of an alkyl group of 1 to 5 carbon atoms such as a methyl group, ethyl group, propyl group, n-butyl group or tert-butyl group have been substituted with the type of halogen atom described above.

The aliphatic cyclic group may be either a monocyclic group or a polycyclic group. The number of carbon atoms within the aliphatic cyclic group is from 3 to 30, preferably from 5 to 30, more preferably from 5 to 20, still more preferably from 6 to 15, and most preferably from 6 to 12.

Specific examples include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In those cases where the aliphatic cyclic group does not include a substituent containing a hetero atom within the ring structure, the aliphatic cyclic group is preferably a polycyclic group, is more preferably a group in which one or more hydrogen atoms have been removed from a polycycloalkane, and is most preferably a group in which one or more hydrogen atoms have been removed from adamantane.

In those cases where the aliphatic cyclic group includes a substituent containing a hetero atom within the ring structure, the substituent containing the hetero atom is preferably —O—, —C(=O)—O—, —S—, —S(=O)$_2$—, or —S(=O)$_2$—O—. Specific examples of this type of aliphatic cyclic group include groups of the formulas (L1) to (L5) and (S1) to (S4) shown below.

[Chemical Formula 43]

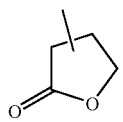
(L1)

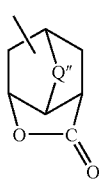
(L2)

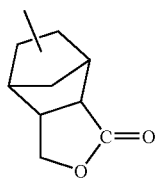
(L3)

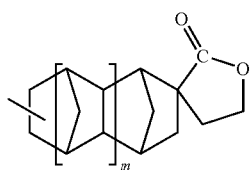
(L4)

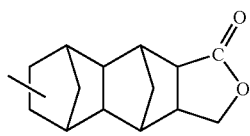
(L5)

(S1)

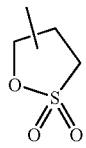
(S2)

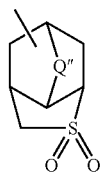
(S3)

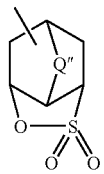
(S4)

wherein Q″ represents an alkylene group of 1 to 5 carbon atoms, —O—, —S—, —O—R$^{94}$— or —S—R$^{95}$—, wherein R$^{94}$ and R$^{95}$ each independently represents an alkylene group of 1 to 5 carbon atoms, and m represents an integer of 0 or 1.

In the above formulas, the alkylene groups for Q″, R$^{94}$ and R$^{95}$ each preferably represents a linear or branched alkylene group, wherein the number of carbon atoms within the alkylene group is typically from 1 to 5, and preferably from 1 to 3.

Specific examples of such alkylene groups include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

Within these aliphatic cyclic groups, some of the hydrogen atoms bonded to the carbon atoms that constitute the ring structure may be substituted with substituents. Examples of these substituents include an alkyl group, alkoxy group, halogen atom, halogenated alkyl group, hydroxyl group, or oxygen atom (=O).

As the alkyl group, an alkyl group of 1 to 5 carbon atoms is preferred, and a methyl group, ethyl group, propyl group, n-butyl group or tert-butyl group is particularly desirable.

Examples of the alkoxy group or halogen atom include the same alkoxy groups or halogen atoms as those exemplified above for the substituent that may substitute some or all of the hydrogen atoms.

In the present invention, as the aliphatic cyclic group X that may have a substituent, a polycyclic aliphatic cyclic group that may have a substituent is preferred. As this polycyclic aliphatic cyclic group, the aforementioned groups in which one or more hydrogen atoms have been removed from a polycycloalkane, and the groups represented by formulas (L2) to (L5) and (S3) to (S4) above are preferred.

In the component (B1), examples of preferred structures for the anion moiety include anions represented by general formula (b1-1a) shown below.

[Chemical Formula 44]

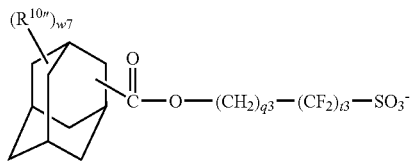

(b1-1a)

wherein, t3 represents an integer of 1 to 3, q3 represents an integer of 1 to 12, w7 represents an integer of 0 to 3, and $R^{10'''}$ is a substituent.

Examples of the substituent $R^{10'''}$ include an alkyl group, alkoxy group, halogen atom, halogenated alkyl group, hydroxyl group, oxygen atom (=O) or cyano group.

As the alkyl group, an alkyl group of 1 to 5 carbon atoms is preferred, and a methyl group, ethyl group, propyl group, n-butyl group or tert-butyl group is particularly desirable.

As the alkoxy group, an alkoxy group of 1 to 5 carbon atoms is preferred, a methoxy group, ethoxy group, n-propoxy group, iso-propoxy group, n-butoxy group or tert-butoxy group is more preferred, and a methoxy group or ethoxy group is the most desirable.

Examples of the halogen atom include a fluorine atom, chlorine atom, bromine atom or iodine atom, and a fluorine atom is preferred.

Examples of the halogenated alkyl group include groups in which some or all of the hydrogen atoms of an alkyl group of 1 to 5 carbon atoms such as a methyl group, ethyl group, propyl group, n-butyl group or tert-butyl group have been substituted with the type of halogen atom described above.

In those cases where the subscript (w7) appended to $R^{10'''}$ is an integer of 2 or more, the plurality of $R^{10'''}$ groups may be the same or different.

t3 is preferably 1 or 2, and is most preferably 1.

q3 is preferably an integer of 1 to 5, more preferably an integer of 1 to 3, and is most preferably 1.

w7 is preferably an integer of 0 to 2, and is more preferably either 0 or 1.

Cation Moiety of Component (B1)

In the above formula (b1), $R^{11'}$ to $R^{13'}$ each independently represents an aryl group that may have a substituent or an alkyl group that may have a substituent.

However, at least one of $R^{11'}$ to $R^{13'}$ is an aryl group having a substituent represented by general formula (b1-0) shown above, and two alkyl groups among $R^{11'}$ to $R^{13'}$ may be bonded to each other to form a ring with the sulfur atom in the formula.

There are no particular limitations on the aryl group for $R^{11'}$ to $R^{13'}$, and examples include aryl groups of 6 to 20 carbon atoms, wherein some or all of the hydrogen atoms within the aryl group may or may not be substituted with substituents other than the substituents represented by general formula (b1-0), such as alkyl groups, alkoxy groups, halogen atoms or hydroxyl groups. This type of aryl group is preferably an aryl group of 6 to 10 carbon atoms, as such groups can be synthesized at low cost. Specific examples thereof include a phenyl group and a naphthyl group.

The alkyl group with which hydrogen atoms of the aryl group may be substituted is preferably an alkyl group of 1 to 5 carbon atoms, is more preferably a methyl group, ethyl group, propyl group, n-butyl group or tert-butyl group, and is most preferably a methyl group.

The alkoxy group with which hydrogen atoms of the aryl group may be substituted is preferably an alkoxy group of 1 to 5 carbon atoms, and is more preferably a methoxy group, ethoxy group, n-propoxy group, iso-propoxy group, n-butoxy group or tert-butoxy group.

The halogen atom with which hydrogen atoms of the aryl group may be substituted is preferably a fluorine atom.

There are no particular limitations on the alkyl group for $R^{11'}$ to $R^{13'}$ and examples thereof include linear, branched or cyclic alkyl groups of 1 to 10 carbon atoms. In terms of achieving excellent resolution, the alkyl group preferably contains 1 to 5 carbon atoms. Specific examples thereof include a methyl group, ethyl group, n-propyl group, isopropyl group, n-butyl group, isobutyl group, n-pentyl group, cyclopentyl group, hexyl group, cyclohexyl group, nonyl group or decanyl group. Of these, a methyl group is most preferable because it provides excellent resolution and enables synthesis to be performed at a low cost.

At least one of $R^{11'}$ to $R^{13'}$ is an aryl group in which some or all of the hydrogen atoms within $R^{11'}$ to $R^{13'}$ have been substituted with a substituent represented by general formula (b1-0) shown below (hereafter frequently referred to as the "substituted aryl group").

Two or more of $R^{11'}$ to $R^{13'}$ may be these substituted aryl groups, although it is most preferable that only one of $R^{11'}$ to $R^{13'}$ represents the substituted aryl group.

[Chemical Formula 45]

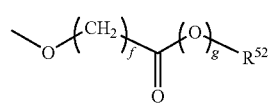

(b1-0)

wherein $R^{52}$ represents a chain-like or cyclic hydrocarbon group, f represents 0 or 1, and g represents 0 or 1.

In formula (b1-0), $R^{52}$ represents a chain-like or cyclic hydrocarbon group.

In $R^{52}$, the hydrocarbon group may be either an aromatic hydrocarbon group or an aliphatic hydrocarbon group.

Examples of the aliphatic hydrocarbon group for $R^{52}$ include linear, branched or cyclic saturated hydrocarbon groups of 1 to 15 carbon atoms, and linear or branched unsaturated hydrocarbon groups of 2 to 5 carbon atoms.

Specific examples of the linear saturated hydrocarbon groups include a methyl group, ethyl group, propyl group, butyl group, pentyl group, hexyl group, heptyl group, octyl group, nonyl group and decanyl group.

Specific examples of the branched saturated hydrocarbon groups include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group, 4-methylpentyl group and tert-butyl group.

The above linear or branched saturated hydrocarbon groups may have a substituent. Examples of the substituent include an alkoxy group, halogen atom, hydroxyl group, oxygen atom (=O), cyano group or carboxyl group.

Of the substituents for the above linear or branched saturated hydrocarbon groups, the alkoxy group is preferably an alkoxy group of 1 to 5 carbon atoms, is more preferably a methoxy group, ethoxy group, n-propoxy group, iso-propoxy group, n-butoxy group or tert-butoxy group, and is most preferably a methoxy group or ethoxy group.

Of the substituents for the above linear or branched saturated hydrocarbon groups, examples of the halogen atom include a fluorine atom, chlorine atom, bromine atom or iodine atom, and a fluorine atom is preferred.

The cyclic saturated hydrocarbon group may be a polycyclic group or a monocyclic group, and examples thereof include cyclic saturated hydrocarbon groups of 3 to 20 carbon atoms, including groups in which one hydrogen atom has been removed from a monocycloalkane or a polycycloalkane (such as a bicycloalkane, tricycloalkane or tetracycloalkane). More specific examples include groups in which one or more hydrogen atoms have been removed from a monocycloalkane such as cyclopentane, cyclohexane, cycloheptane or cyclooctane, or a polycycloalkane such as adamantane, norbornane, isobornane, tricyclodecane or tetracyclododecane.

The cyclic saturated hydrocarbon group may have a substituent. The group having a substituent may be a group in which some of the carbon atoms that constitute the ring structure in the cyclic saturated hydrocarbon group have been substituted with a hetero atom (the former case), and groups in which some or all of the hydrogen atoms bonded to the ring structure in the cyclic saturated hydrocarbon group have been substituted with a hetero atom (the latter case).

Examples of the former case include groups in which one or more hydrogen atoms have been removed from a heterocycloalkane in which some of the carbon atoms that constitute the ring(s) of a monocycloalkane or a polycycloalkane have been substituted with a hetero atom such as an oxygen atom, sulfur atom or nitrogen atom. Further, the ring structure may include an ester linkage (—C(=O)—O—). Specific examples include lactone-containing monocyclic groups such as groups in which one hydrogen atom has been removed from γ-butyrolactone, and lactone-containing polycyclic groups in which one hydrogen atom has been removed from a lactone ring-containing bicycloalkane, tricycloalkane or tetracycloalkane.

Examples of the substituent in the latter case include those groups exemplified above as substituents with which the linear or branched saturated hydrocarbon groups may be substituted, as well as alkyl groups. The alkyl group substituent is preferably a lower alkyl group of 1 to 5 carbon atoms, and is more preferably a methyl group or ethyl group. The carbon atom within the ring structure to which the alkyl group substituent is bonded is preferably bonded to the terminal of the —C(=O)—(O)g- group in the substituent represented by general formula (b1-0) shown above.

Examples of the linear unsaturated hydrocarbon group for $R^{52}$ include a vinyl group, propenyl group (allyl group) or butynyl group.

Examples of the branched unsaturated hydrocarbon group include a 1-methylpropenyl group or 2-methylpropenyl group.

The linear or branched unsaturated hydrocarbon group may have a substituent. Examples of this substituent include the same groups exemplified above as substituents for the linear or branched saturated hydrocarbon group.

The aromatic hydrocarbon group for $R^{52}$ may be a group having an aromatic hydrocarbon ring in which the aromatic ring skeleton is composed solely of carbon atoms, or a group having an aromatic heterocycle in which the aromatic ring skeleton includes a hetero atom other than a carbon atom.

Specific examples of the aromatic hydrocarbon group include aryl groups in which one hydrogen atom has been removed from an aromatic hydrocarbon ring such as a phenyl group, biphenyl group, fluorenyl group, naphthyl group, anthryl group or phenanthryl group;

heteroaryl groups in which some of the carbon atoms that constitute a ring of one of the above aryl groups have been substituted with a hetero atom such as an oxygen atom, sulfur atom or nitrogen atom; and arylalkyl groups such as a benzyl group, phenethyl group, 1-naphthylmethyl group, 2-naphthylmethyl group, 1-naphthylethyl group or 2-naphthylethyl group. The number of carbon atoms within the alkyl chain of the arylalkyl group is preferably from 1 to 4, more preferably from 1 to 2, and is most preferably 1.

The aromatic hydrocarbon group may have a substituent. For example, some of the carbon atoms that constitute the aromatic ring of the aromatic hydrocarbon group may be substituted with a hetero atom, or some of the hydrogen atoms bonded to the aromatic ring of the aromatic hydrocarbon group may be substituted with a substituent.

Examples of the former case include heteroaryl groups in which some of the carbon atoms that constitute the aromatic ring of an aforementioned aryl group have been substituted with a hetero atom such as an oxygen atom, sulfur atom or nitrogen atom, and heteroarylalkyl groups in which some of the carbon atoms that constitute the aromatic hydrocarbon ring within an aforementioned arylalkyl group have been substituted with an aforementioned hetero atom.

Examples of the substituent in the latter case include an alkyl group, alkoxy group, halogen atom, halogenated alkyl group, hydroxyl group or oxygen atom (=O).

As the alkyl group for the substituent within the aromatic hydrocarbon group, a lower alkyl group of 1 to 5 carbon atoms is preferred, and a methyl group, ethyl group, propyl group, n-butyl group or tert-butyl group is the more preferred.

As the alkoxy group for the substituent within the aromatic hydrocarbon group, an alkoxy group of 1 to 5 carbon atoms is preferred, a methoxy group, ethoxy group, n-propoxy group, iso-propoxy group, n-butoxy group or tert-butoxy group is more preferred, and a methoxy group or ethoxy group is the most desirable.

Examples of the halogen atom for the substituent within the aromatic hydrocarbon group include a fluorine atom, chlorine atom, bromine atom or iodine atom, and a fluorine atom is preferred.

Examples of the halogenated alkyl group for the substituent within the aromatic hydrocarbon group include groups in which some or all of the hydrogen atoms within an aforementioned alkyl group have been substituted with the aforementioned halogen atoms.

Of the possibilities outline above, $R^{52}$ is preferably a cyclic hydrocarbon group, is more preferably a cyclic aliphatic hydrocarbon group, is still more preferably a cyclic saturated hydrocarbon group, and is most preferably a group in which one or more hydrogen atoms have been removed from adamantane.

Further, those cases where $R^{52}$ is a chain-like hydrocarbon group are also preferred, a linear or branched saturated hydrocarbon group is more preferable, a branched saturated hydrocarbon group is still more preferable, and a tert-butyl group is the most desirable.

In the above formula (b1-0), f represents either 0 or 1.

In formula (b1-0), g represents either 0 or 1.

The $R^{11'}$ to $R^{13'}$ groups other than the substituted aryl group described above each preferably represents a phenyl group or a naphthyl group, and most preferably a phenyl group.

In formula (b1), two alkyl groups of $R^{11'}$ to $R^{13'}$ may be bonded to each other to form a ring with the sulfur atom in the formula. In such a case, the ring formed is preferably a 3- to 10-membered ring including the sulfur atom, and is more preferably a 5- to 7-membered ring.
Specific examples of preferred forms for the cation moiety of component (B1) are shown below.
[Chemical Formula 46]
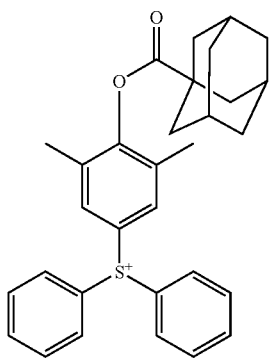
(b1-1c-1)
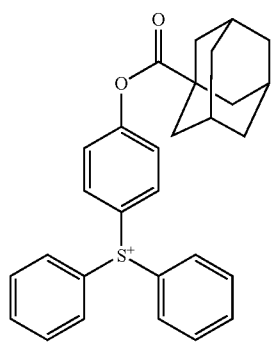
(b1-1c-2)
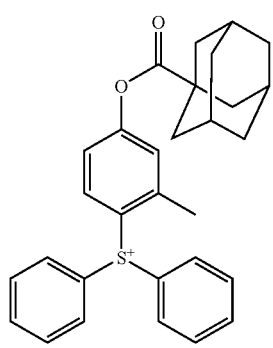
(b1-1c-3)
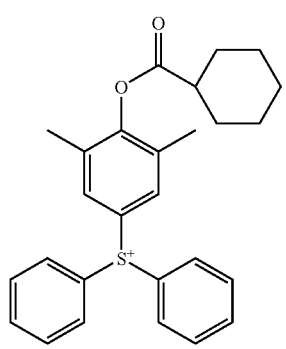
(b1-1c-4)
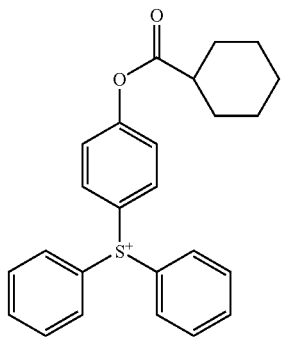
(b1-1c-5)
[Chemical Formula 47]
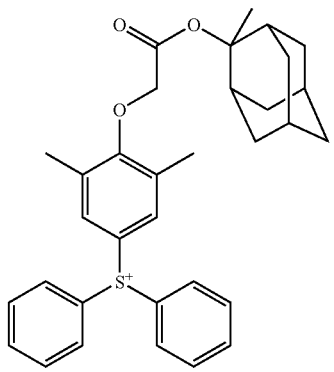
(b1-2c-1)
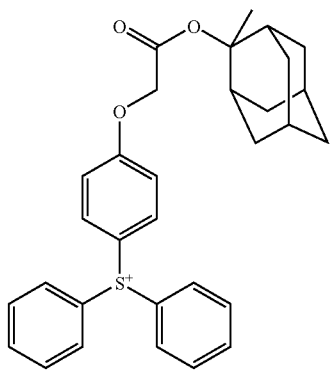
(b1-2c-2)
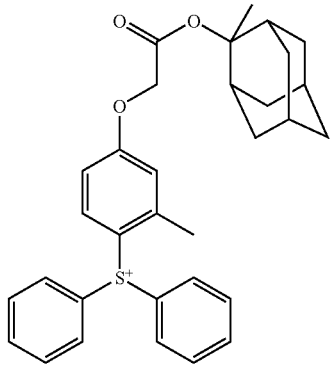
(b1-2c-3)

-continued (b1-2c-4)

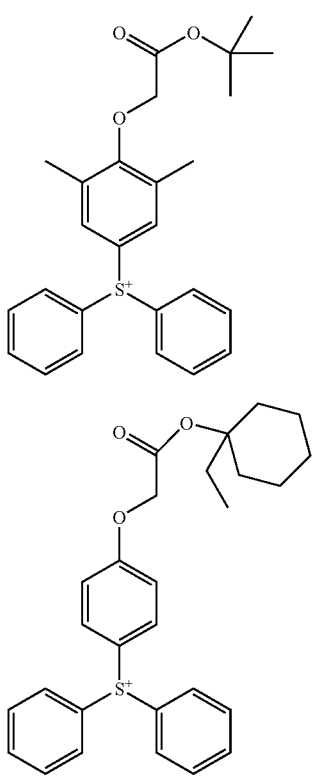

(b1-2c-5)

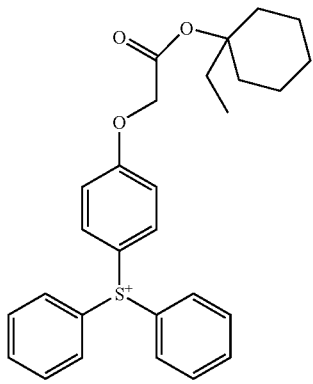

As the component (B1), one type of compound may be used, or two or more types may be used in combination.

The proportion of the component (B1) within the component (B), based on the total weight of the component (B), is preferably at least 50% by weight, more preferably 60% by weight or more, and still more preferably 75% by weight or more, and this proportion may be 100% by weight. A proportion of 100% by weight is the most preferred option.

Provided the proportion of the component (B1) is at least as large as the lower limit of the above-mentioned range, the effects of the present invention can be improved.

[Component (B2)]

In the component (B), an acid generator (B2) other than the aforementioned component (B1) (hereafter, referred to as "component (B2)") may be used in combination with the component (B1).

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes and poly(bis-sulfonyl)diazomethanes, nitrobenzylsulfonate-based acid generators, iminosulfonate-based acid generators, and disulfone-based acid generators.

As an onium salt-based acid generator, compounds represented by general formula (b-1) or (b-2) shown below can be favorably used.

[Chemical Formula 48]

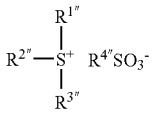 (b-1)

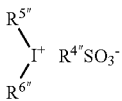 (b-2)

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom in the formula, and $R^{4\prime\prime}$ represents a an alkyl group, halogenated alkyl group, aryl group or alkenyl group that may have a substituent, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), examples of $R^{1\prime\prime}$ to $R^{3\prime\prime}$ include the same groups as those exemplified above for $R^{11\prime}$ to $R^{13\prime}$ in general formula (b1) but excluding those cases where $R^{11\prime}$ to $R^{13\prime}$ is an aryl group having a substituent represented by general formula (b1-0).

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

It is particularly desirable that each of $R^{1\prime\prime}$ to $R^{3\prime\prime}$ is a phenyl group or a naphthyl group.

$R^{4\prime\prime}$ represents an alkyl group, halogenated alkyl group, aryl group or alkenyl group that may have a substituent.

The alkyl group for $R^{4\prime\prime}$ may be a linear, branched or cyclic group.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

Examples of the halogenated alkyl group for $R^{4\prime\prime}$ include groups in which some or all of the hydrogen atoms in an aforementioned linear, branched or cyclic alkyl group have been substituted with halogen atoms. Examples of the halogen atom include a fluorine atom, chlorine atom, bromine atom or iodine atom, and a fluorine atom is preferred In the halogenated alkyl group, the ratio of the number of halogen atoms relative to the combined total of halogen atoms and hydrogen atoms within the halogenated alkyl group (namely, the halogenation ratio (%)) is preferably within a range from 10 to 100%, more preferably from 50 to 100%, and is most preferably 100%. Higher values for the halogenation ratio are preferred, as they result in stronger acid strength.

The aryl group for $R^{4\prime\prime}$ is preferably an aryl group of 6 to 20 carbon atoms.

The alkenyl group for $R^{4\prime\prime}$ is preferably an alkenyl group of 2 to 10 carbon atoms.

In $R^{4\prime\prime}$, the description that the group "may have a substituent" means that some or all of the hydrogen atoms within the linear, branched or cyclic alkyl group, halogenated alkyl group, aryl group or alkenyl group may be substituted with a substituent (an atom other than a hydrogen atom or a group).

The number of such substituents within $R^{4'''}$ may be either 1, or 2 or more.

Examples of the substituent include a halogen atom, hetero atom, alkyl group, or group represented by a formula: $X^0$-$Q^1$-, wherein $Q^1$ represents a divalent linking group containing an oxygen atom and $X^0$ represents a hydrocarbon group of 3 to 30 carbon atoms that may have a substituent.

Examples of the halogen atom and alkyl group include the same atoms and groups exemplified above in relation to the halogen atom and alkyl group within the halogenated alkyl group for $R^{4'''}$.

Examples of the hetero atom include an oxygen atom, nitrogen atom or sulfur atom.

In the group represented by $X^0$-$Q^1$-, $Q^1$ represents a divalent linking group containing an oxygen atom. $Q^1$ may include atoms other than the oxygen atom. Examples of these atoms other than the oxygen atom include a carbon atom, hydrogen atom, oxygen atom, sulfur atom and nitrogen atom.

Examples of the divalent linking group containing an oxygen atom include non-hydrocarbon oxygen atom-containing linkage groups such as an oxygen atom (an ether linkage, —O—), an ester linkage (—C(=O)—O—), an amide linkage (—C(=O)—NH—), a carbonyl group (—C(=O)—) and a carbonate linkage (—O—C(=O)—O—); and combinations of an aforementioned non-hydrocarbon oxygen atom-containing linkage group and an alkylene group.

Examples of such combinations include groups represented by —$R^{91}$—O—, —$R^{92}$—O—C(=O)— and —C(=O)—O—$R^{93}$—O—C(=O)— (wherein $R^{91}$ to $R^{93}$ each independently represents an alkylene group).

The alkylene groups for $R^{91}$ to $R^{93}$ each preferably represents a linear or branched alkylene group, wherein the number of carbon atoms within the alkylene group is typically from 1 to 12, more preferably from 1 to 5, and most preferably from 1 to 3.

Specific examples of such alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As $Q^1$, a divalent linkage group containing an ester linkage or ether linkage is preferred, and of such linkage groups, groups represented by —$R^{91}$—O—, —$R^{92}$—O—C(=O)— and —C(=O)—O—$R^{93}$—O—C(=O)— are preferred.

In the group represented by $X^0$-$Q^1$-, the hydrocarbon group represented by $X^0$ may be either an aromatic hydrocarbon group or an aliphatic hydrocarbon group.

The aromatic hydrocarbon group is a hydrocarbon group that contains an aromatic ring. The number of carbon atoms within the aromatic hydrocarbon group is preferably within a range from 3 to 30 carbon atoms, more preferably from 5 to 30 carbon atoms, still more preferably from 5 to 20 carbon atoms, still more preferably from 6 to 15 carbon atoms, and most preferably from 6 to 12 carbon atoms. This number of carbon atoms does not include any carbon atoms within any substituents.

Specific examples of the aromatic hydrocarbon group include aryl groups in which one hydrogen atom has been removed from an aromatic hydrocarbon ring such as a phenyl group, biphenyl group, fluorenyl group, naphthyl group, anthryl group or phenanthryl group, and arylalkyl groups such as a benzyl group, phenethyl group, 1-naphthylmethyl group, 2-naphthylmethyl group, 1-naphthylethyl group or 2-naphthylethyl group. The number of carbon atoms within the alkyl chain of the arylalkyl group is preferably from 1 to 4, more preferably from 1 to 2, and is most preferably 1.

The aromatic hydrocarbon group may have a substituent. For example, some of the carbon atoms that constitute the aromatic ring of the aromatic hydrocarbon group may be substituted with a hetero atom, or some of the hydrogen atoms bonded to the aromatic ring of the aromatic hydrocarbon group may be substituted with a substituent.

Examples of the former case include heteroaryl groups in which some of the carbon atoms that constitute the aromatic ring of an aforementioned aryl group have been substituted with a hetero atom such as an oxygen atom, sulfur atom or nitrogen atom, and heteroarylalkyl groups in which some of the carbon atoms that constitute the aromatic hydrocarbon ring within an aforementioned arylalkyl group have been substituted with an aforementioned hetero atom.

Examples of the substituent within the aromatic hydrocarbon group in the latter case include an alkyl group, alkoxy group, halogen atom, halogenated alkyl group, hydroxyl group or oxygen atom (=O).

As the alkyl group for the substituent within the aromatic hydrocarbon group, an alkyl group of 1 to 5 carbon atoms is preferred, and a methyl group, ethyl group, propyl group, n-butyl group or tert-butyl group is the more preferred.

As the alkoxy group for the substituent within the aromatic hydrocarbon group, an alkoxy group of 1 to 5 carbon atoms is preferred, and a methoxy group, ethoxy group, n-propoxy group, iso-propoxy group, n-butoxy group or tert-butoxy group is more preferred, and a methoxy group or ethoxy group is the most desirable.

Examples of the halogen atom for the substituent within the aromatic hydrocarbon group include a fluorine atom, chlorine atom, bromine atom or iodine atom, and a fluorine atom is preferred.

Examples of the halogenated alkyl group for the substituent within the aromatic hydrocarbon group include groups in which some or all of the hydrogen atoms within an aforementioned alkyl group have been substituted with the aforementioned halogen atoms.

The aliphatic hydrocarbon group for $X^0$ may be either a saturated aliphatic hydrocarbon group or an unsaturated aliphatic hydrocarbon group. Further, the aliphatic hydrocarbon group may be a linear, branched or cyclic group.

In the aliphatic hydrocarbon group for $X^0$, some of the carbon atoms that constitute the aliphatic hydrocarbon group may be substituted with a substituent that contains a hetero atom, and some or all of the hydrogen atoms that constitute the aliphatic hydrocarbon group may also be substituted with substituents that contain a hetero atom.

There are no particular limitations on this "hetero atom" within the group $X^0$ as long as it is an atom other than a carbon atom or hydrogen atom, and examples include a halogen atom, oxygen atom, sulfur atom or nitrogen atom.

Examples of the halogen atom include a fluorine atom, chlorine atom, iodine atom and bromine atom.

The substituent that contains a hetero atom may be composed solely of the hetero atom, or may be a group that includes a group or atom(s) other than the hetero atom.

Specific examples of the substituent that may substitute some of the carbon atoms include —O—, —C(=O)—O—, —C(=O)—, —O—C(=O)—O—, —C(=O)—NH—, —NH— (wherein the H may be substituted with a substituent such as an alkyl group or acyl group), —S—, —S(=O)$_2$—, and —S(=O)$_2$—O—. These substituents may be included within the cyclic structure in those cases where the aliphatic hydrocarbon group is a cyclic group.

Specific examples of the substituent that may substitute some or all of the hydrogen atoms include an alkoxy group, halogen atom, halogenated alkyl group, hydroxyl group, oxygen atom (=O), and cyano group.

The alkoxy group is preferably an alkoxy group of 1 to 5 carbon atoms, is more preferably a methoxy group, ethoxy group, n-propoxy group, iso-propoxy group, n-butoxy group or tert-butoxy group, and is most preferably a methoxy group or ethoxy group.

Examples of the halogen atom include a fluorine atom, chlorine atom, bromine atom or iodine atom, and a fluorine atom is preferred.

Examples of the halogenated alkyl group include groups in which some or all of the hydrogen atoms of an alkyl group of 1 to 5 carbon atoms such as a methyl group, ethyl group, propyl group, n-butyl group or tert-butyl group have been substituted with the type of halogen atom described above.

As the aliphatic hydrocarbon group, a linear or branched saturated hydrocarbon group, a linear or branched monovalent unsaturated hydrocarbon group, or a cyclic aliphatic hydrocarbon group (an aliphatic cyclic group) is preferred.

The linear saturated hydrocarbon group (alkyl group) preferably contains 1 to 20 carbon atoms, more preferably 1 to 15 carbon atoms, and most preferably 1 to 10 carbon atoms. Specific examples include a methyl group, ethyl group, propyl group, butyl group, pentyl group, hexyl group, heptyl group, octyl group, nonyl group, decanyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group, or docosyl group.

The branched saturated hydrocarbon group (alkyl group) preferably contains 3 to 20 carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group, or 4-methylpentyl group.

The unsaturated hydrocarbon group preferably contains 2 to 10 carbon atoms, more preferably 2 to 5 carbon atoms, still more preferably 2 to 4 carbon atoms, and most preferably 3 carbon atoms. Examples of the linear monovalent unsaturated hydrocarbon group include a vinyl group, propenyl group (allyl group) or butynyl group. Examples of the branched monovalent unsaturated hydrocarbon group include a 1-methylpropenyl group or 2-methylpropenyl group.

As the unsaturated hydrocarbon group, of the above, a propenyl group is particularly preferred.

Examples of the aliphatic cyclic group for $X^0$ include the same groups as those exemplified above for the aliphatic cyclic group for X in general formula (b1).

In the present invention, $X^0$ is preferably a cyclic group that may have a substituent. This cyclic group may be either an aromatic hydrocarbon group that may have a substituent, or an aliphatic cyclic group that may have a substituent, although is preferably an aliphatic cyclic group that may have a substituent.

As the aromatic hydrocarbon group, a naphthyl group that may have a substituent or a phenyl group that may have a substituent is preferred.

As the aliphatic cyclic group that may have a substituent, a polycyclic aliphatic cyclic group that may have a substituent is preferred. As this polycyclic aliphatic cyclic group, groups in which one or more hydrogen atoms have been removed from an above-mentioned polycycloalkane, and the groups (L2) to (L5) and (S3) to (S4) described above are preferred.

In the present invention, R4" preferably contains $X^0$-$Q^1$- as a substituent. In such cases, R4" is preferably a group represented by $X^0$-$Q^1$-$Y^0$—, wherein $Q^1$ and $X^0$ are as defined above, and $Y^0$ represents an alkylene group of 1 to 4 carbon atoms that may have a substituent or a fluorinated alkylene group of 1 to 4 carbon atoms that may have a substituent.

In the group represented by $X^0$-$Q^1$-$Y^0$—, examples of the alkylene group for $Y^0$ include those groups among the alkylene groups exemplified above for $Q^1$ that contain from 1 to 4 carbon atoms.

Furthermore, examples of the fluorinated alkylene group for $Y^0$ include the same fluorinated alkylene groups as those exemplified above for $Y^1$ in general formula (b1).

In formula (b-2), $R^{5\prime\prime\prime}$ and $R^{6\prime\prime\prime}$ each independently represents an aryl group or alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent aryl groups.

As the aryl group for $R^{5\prime\prime\prime}$ and $R^{6\prime\prime\prime}$, the same groups as the aryl groups for $R^{1\prime\prime\prime}$ to $R^{3\prime\prime\prime}$ can be exemplified.

As the alkyl group for $R^{5\prime\prime\prime}$ and $R^{6\prime\prime\prime}$, the same groups as the alkyl groups for $R^{1\prime\prime\prime}$ to $R^{3\prime\prime\prime}$ can be exemplified.

It is particularly desirable that both of $R^{5\prime\prime\prime}$ and $R^{6\prime\prime\prime}$ represent phenyl groups.

Examples of $R^{4\prime\prime\prime}$ in formula (b-2) include the same groups as those mentioned above for $R^{4\prime\prime\prime}$ in formula (b-1).

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl) sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl) sulfonium trifluoromethanesulfonate, heptafluoropropanesulfonate or nonafluorobutanesulfonate; di(1-naphthyl) phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl) tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts has been replaced by methanesulfonate, n-propanesulfonate, n-butanesulfonate, or n-octanesulfonate.

Furthermore, it is also possible to use salts in which the anion moiety of the above onium salts has been replaced with an anion moiety represented by one of formulas (b2-1) to (b2-7) shown below.

[Chemical Formula 49]

(b2-1)

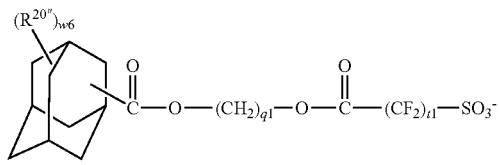

(b2-2)

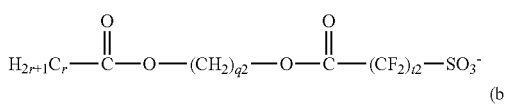

(b2-3)

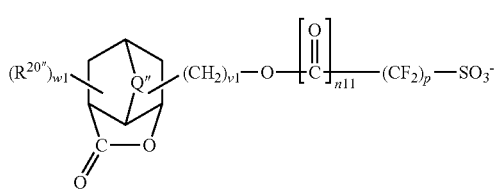

(b2-4)

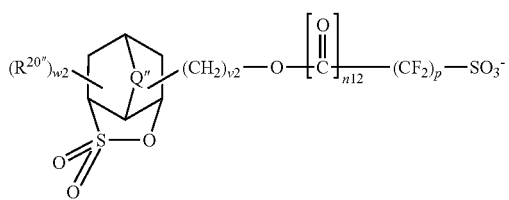

(b2-5)

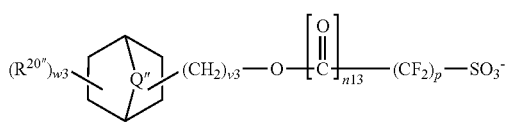

(b2-6)

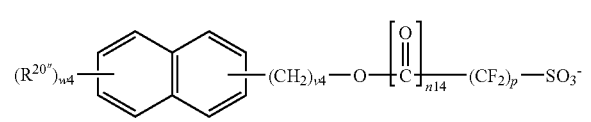

-continued (b2-7)

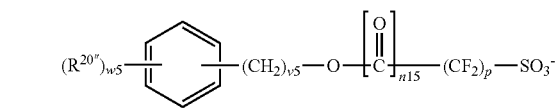

wherein p represents an integer of 1 to 3, q1 and q2 each independently represents an integer of 1 to 5, t1 and t2 each independently represents an integer of 1 to 3, r represents an integer of 1 to 20, $R^{20''}$ represents a substituent, n11 to n15 each independently represents 0 or 1, v1 to v5 each independently represents an integer of 0 to 3, w1 to w6 each independently represents an integer of 0 to 3, and Q" is as defined above.

Examples of the substituent for $R^{20''}$ include the same groups as those exemplified above as the substituent for $X^0$ which may be either an aliphatic hydrocarbon group or an aromatic hydrocarbon group.

In those cases where the subscript (w1 to w6) appended to $R^{20''}$ is 2 or more, the plurality of $R^{20''}$ groups within the compound may be either the same or different.

Further, onium salt-based acid generators in which the anion moiety in general formula (b-1) or (b-2) is replaced with an anion moiety represented by general formula (b-3) or (b-4) shown below (and the cation moiety is the same as (b-1) or (b-2)) may also be used.

[Chemical Formula 50]

(b-3)

(b-4)

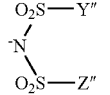

wherein X" represents an alkylene group of 2 to 6 carbon atoms in which at least one hydrogen atom has been substituted with a fluorine atom, and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

Within the above-mentioned ranges for the number of carbon atoms, the smaller the number of carbon atoms of the alkylene group for X" or the number of carbon atoms of the alkyl group for Y" and Z", the more the solubility in a resist solvent can be improved.

Further, in the alkylene group for X" or the alkyl group for Y" and Z", it is preferable that the number of hydrogen atoms substituted with fluorine atoms is as large as possible, because the acid strength increases and the transparency to high energy radiation of 200 nm or less or electron beam is improved.

The amount of fluorine atoms within the alkylene group or alkyl group, namely the fluorination ratio, is preferably within a range from 70 to 100%, more preferably from 90 to 100%, and it is particularly desirable that the alkylene group or alkyl group is a perfluoroalkylene group or perfluoroalkyl group in which all the hydrogen atoms have been substituted with fluorine atoms.

Furthermore, a sulfonium salt having a cation moiety represented by general formula (b-5) or (b-6) shown below may also be used as an onium salt-based acid generator.

[Chemical Formula 51]

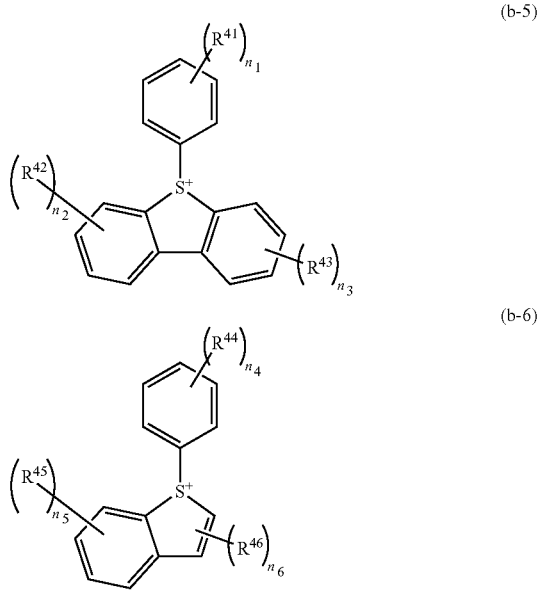

wherein $R^{41}$ to $R^{46}$ each independently represents an alkyl group, acetyl group, alkoxy group, carboxyl group, hydroxyl group or hydroxyalkyl group, $n_1$ to $n_5$ each independently represents an integer of 0 to 3, and $n_6$ represents an integer of 0 to 2.

The alkyl group for $R^{41}$ to $R^{46}$ is preferably an alkyl group of 1 to 5 carbon atoms, and of these, a linear or branched alkyl group is preferred. A methyl group, ethyl group, propyl group, isopropyl group, n-butyl group or tert-butyl group is particularly desirable.

The alkoxy group is preferably an alkoxy group of 1 to 5 carbon atoms, and of these, a linear or branched alkoxy group is preferred, and a methoxy group or ethoxy group is particularly desirable.

The hydroxyalkyl group is preferably a group in which one or more of the hydrogen atoms within an above-mentioned alkyl group have been substituted with a hydroxyl group, and specific examples include a hydroxymethyl group, hydroxyethyl group and hydroxypropyl group.

When the subscripts $n_1$ to $n_6$ appended to $R^{41}$ to $R^{46}$ represent an integer of 2 or more, the plurality of $R^{41}$ to $R^{46}$ groups may be the same or different.

$n_1$ is preferably from 0 to 2, more preferably 0 or 1, and still more preferably 0.

It is preferable that $n_2$ and $n_3$ each independently represents 0 or 1, and more preferably 0.

$n_4$ is preferably from 0 to 2, and more preferably 0 or 1.

$n_5$ is preferably 0 or 1, and more preferably 0.

$n_6$ is preferably 0 or 1, and more preferably 1.

There are no particular limitations on the anion moiety of the sulfonium salt having a cation represented by general formula (b-5) or (b-6) as the cation moiety, and the same anion moieties as those used within previously proposed onium salt-based acid generators may be used.

Examples of such anion moieties include fluorinated alkylsulfonate ions such as the anion moieties ($R^{4"}SO_3^-$) for the onium salt-based acid generators represented by general formula (b-1) or (b-2) shown above, and anion moieties represented by general formula (b-3) or (b-4) shown above. Among these, fluorinated alkylsulfonate ions are preferable, fluorinated alkylsulfonic acid ions of 1 to 4 carbon atoms are more preferable, and linear perfluoroalkylsulfonic acid ions of 1 to 4 carbon atoms are particularly desirable. Specific examples include a trifluoromethylsulfonic acid ion, heptafluoro-n-propylsulfonic acid ion and nonafluoro-n-butylsulfonic acid ion.

In the present description, an oxime sulfonate-based acid generator is a compound having at least one group represented by general formula (B-1) shown below, and has a feature of generating acid upon irradiation. Such oxime sulfonate-based acid generators are widely used for chemically amplified resist compositions, and any of these compounds may be appropriately selected for use.

[Chemical Formula 52]

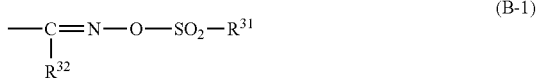

wherein $R^{31}$ and $R^{32}$ each independently represents an organic group.

The organic group for $R^{31}$ and $R^{32}$ refers to a group containing a carbon atom, and may include atoms other than carbon atoms (such as a hydrogen atom, an oxygen atom, a nitrogen atom, a sulfur atom, a halogen atom (such as a fluorine atom and a chlorine atom) and the like).

As the organic group for $R^{31}$, a linear, branched or cyclic alkyl group or aryl group is preferable. The alkyl group or the aryl group may have a substituent. The substituent is not particularly limited, and examples thereof include a fluorine atom and a linear, branched or cyclic alkyl group having 1 to 6 carbon atoms. The expression "may have a substituent" means that some or all of the hydrogen atoms of the alkyl group or the aryl group may be substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched or cyclic alkyl group, an aryl group, or a cyano group is preferable. Examples of the alkyl group and the aryl group for $R^{32}$ are the same as those for the alkyl group and the aryl group for $R^{31}$.

As $R^{32}$, a cyano group, an alkyl group of 1 to 8 carbon atoms having no substituent, or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 53]

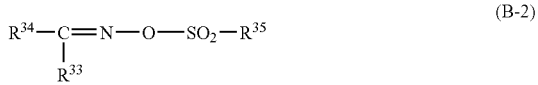

(B-2)

wherein $R^{33}$ represents a cyano group, an alkyl group having no substituent or a halogenated alkyl group, $R^{34}$ represents an aryl group, and $R^{35}$ represents an alkyl group having no substituent or a halogenated alkyl group.

[Chemical Formula 54]

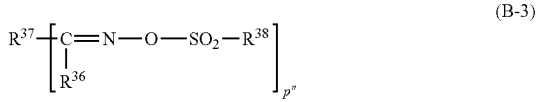

(B-3)

wherein $R^{36}$ represents a cyano group, an alkyl group having no substituent or a halogenated alkyl group, $R^{37}$ represents a divalent or trivalent aromatic hydrocarbon group, $R^{38}$ represents an alkyl group having no substituent or a halogenated alkyl group, and p" represents 2 or 3.

In general formula (B-2), the alkyl group having no substituent or the halogenated alkyl group for $R^{33}$ preferably contains 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms of the alkyl group fluorinated, more preferably 70% or more fluorinated, and most preferably 90% or more fluorinated.

Examples of the aryl group for $R^{34}$ include groups in which one hydrogen atom has been removed from an aromatic hydrocarbon ring, such as a phenyl group, biphenyl group, fluorenyl group, naphthyl group, anthryl group or phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group or halogenated alkyl group as the substituent preferably contains 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably contains 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms of the alkyl group fluorinated, more preferably 70% or more fluorinated, and still more preferably 90% or more fluorinated. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which an additional one or two hydrogen atoms have been removed from the aryl group for $R^{34}$.

As the alkyl group having no substituent or the halogenated alkyl group for $R^{38}$, the same groups as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 04/074242 pamphlet (Examples 1 to 40 described on pages 65 to 85) may be preferably used.

Furthermore, as preferred examples, the following compounds can be exemplified.

[Chemical Formula 55]

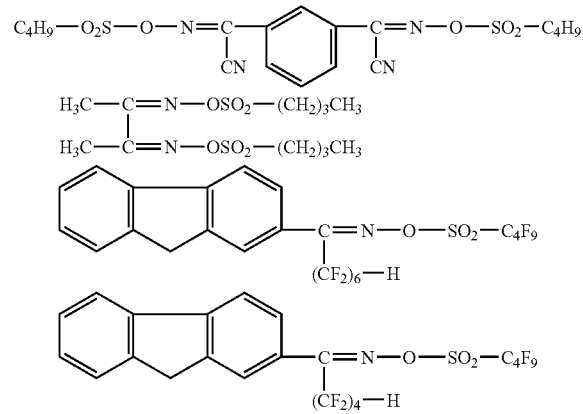

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be favorably used.

Furthermore, examples of poly(bis-sulfonyl)diazomethanes include those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B2), one type of acid generator may be used, or two or more types may be used in combination.

The total amount of the component (B) within the resist composition of the present invention is preferably within a range from 0.5 to 50 parts by weight, and preferably from 1 to 30 parts by weight, relative to 100 parts by weight of the component (A). When the amount of the component (B) is within the above-mentioned range, formation of a resist pattern can be performed satisfactorily. Further, by virtue of the above-mentioned range, a uniform solution can be obtained and the storage stability becomes satisfactory.

<Optional Components>
[Component (D)]

In the resist composition of the present invention, in order to improve the resist pattern shape and the post exposure stability of the latent image formed by the pattern-wise exposure of the resist layer, a nitrogen-containing organic compound (D) (hereafter referred to as "component (D)") may be added as an optional component.

A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, wherein the aliphatic groups preferably contain from 1 to 20 carbon atoms.

Examples of these aliphatic amines include amines in which at least one hydrogen atom of ammonia ($NH_3$) has been substituted with an alkyl group or hydroxyalkyl group of no more than 20 carbon atoms (namely, alkylamines or alkyl alcohol amines), and cyclic amines.

Specific examples of the alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, lauryldiethanolamine and stearyldiethanolamine. Among these, trialkylamines and alkyl alcohol amines, each containing alkyl groups of 5 to 10 carbon atoms are preferred, and tri-n-pentylamine, diethanolamine and stearyldiethanolamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Examples of aromatic amines include aniline, pyridine, 4-dimethylaminopyridine, pyrrole, indole, pyrazole, imidazole, and derivatives thereof, as well as diphenylamine, triphenylamine and tribenzylamine.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-

(1-ethoxyethoxy)ethyl}amine, tris{2-(1-ethoxypropoxy)ethyl}amine, and tris[2-{2-(2-hydroxyethoxy)ethoxy}ethyl]amine.

These compounds may be used either alone, or in combinations of two or more compounds.

The component (D) is typically used in an amount within a range from 0.01 to 5.0 parts by weight, relative to 100 parts by weight of the component (A).

[Component (E)]

Furthermore, in the resist composition of the present invention, in order to prevent any deterioration in sensitivity, and further improve the resist pattern shape and the post exposure stability of the latent image formed by the pattern-wise exposure of the resist layer, at least one compound (E) (hereafter referred to as "component (E)") selected from the group consisting of organic carboxylic acids, and phosphorus oxo acids and derivatives thereof may be added.

Examples of the organic carboxylic acids include acetic acid, malonic acid, citric acid, malic acid, succinic acid, benzoic acid and salicylic acid.

Examples of the phosphorus oxo acids include phosphoric acid, phosphonic acid and phosphinic acid and among these, phosphonic acid is particularly desirable.

Examples of the phosphorus oxo acid derivatives include esters in which a hydrogen atom within an above-mentioned oxo acid is substituted with a hydrocarbon group, and the like. Examples of the hydrocarbon group include an alkyl group of 1 to 5 carbon atoms or an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters and the like such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenyl phosphinate.

As the component (E), one type of compound may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives may also be added to the resist composition of the present invention. Examples of such miscible additives include additive resins for improving the performance of the resist film, surfactants for improving the coating properties, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, frequently referred to as "component (S)").

The component (S) may be any organic solvent that can dissolve the respective components to give a uniform solution, and any one or more types of organic solvent can be appropriately selected from those that have been conventionally known as solvents for chemically amplified resists.

Examples of the organic solvent include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol and dipropylene glycol; polyhydric alcohol derivatives including compounds having an ester bond, such as ethylene glycol monoacetate, diethylene glycol monoacetate, propylene glycol monoacetate and dipropylene glycol monoacetate, and compounds having an ether bond, such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene.

These organic solvents may be used individually, or as a mixed solvent containing two or more different solvents.

Of these solvents, propylene glycol monomethyl ether acetate (PGMEA), propylene glycol monomethyl ether (PGME), and EL are preferred.

Further, a mixed solvent obtained by mixing PGMEA with a polar solvent is also preferred. The mixing ratio (weight ratio) of the mixed solvent can be determined appropriately with due consideration of the compatibility of the PGMEA with the polar solvent, but is preferably within a range from 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferred. In such a case, the mixing ratio, reported as a weight ratio between the former and latter solvents, is preferably within a range from 70:30 to 95:5.

The amount used of the component (S) is not particularly limited, and is adjusted appropriately to a concentration that enables application of the coating solution to a substrate in accordance with the desired thickness of the coating film. In general, the organic solvent is used in an amount that yields a solid content concentration for the resist composition that is within a range from 2 to 20% by weight, and preferably from 5 to 15% by weight.

The resist composition of the present invention described above represents a novel composition that has been unknown until now.

According to the resist composition of the present invention, a resist pattern of favorable shape can be formed. For example, in the case of formation of a resist pattern having a hole pattern, the circularity of the holes and the uniformity (CDU) of the hole diameter (CD) can be improved, enabling a resist pattern of favorable shape to formed with a narrow pitch. The reasons that these effects are obtained are not entirely clear, but are thought to include the following.

The resist composition of the present invention includes the acid generator (B1) consisting of a compound represented by the above general formula (b1).

This component (B1) has an anion moiety that includes a substituent containing both an ester linkage (—C(═O)—O—) and an aliphatic cyclic group, and compared with conventional acid generator anion moieties such as a nonafluorobutanesulfonate ion, this anion moiety of the present invention exhibits a higher degree of polarity and has a structure that is more sterically bulky. As a result, diffusion within the resist film of the acid generated from the component (B1) upon exposure (namely, the anion moiety) is inhibited both chemically and physically, and because the diffusion length is shorter than that observed for conventional acid generators, diffusion of the acid generated within the exposed portions into the unexposed portions is favorably suppressed.

Furthermore, the component (B1) also has an aryl group having a substituent represented by general formula (b1-0) as the cation moiety. It is thought that because the substituent represented by general formula (b1-0) exhibits a high degree of compatibility with the component (A), the component (B1) can be distributed more uniformly within the resist film than conventional acid generators. Further, the component (B1) exhibits excellent solubility in the organic solvent (S) (the resist solvent).

Accordingly, it is thought that using this type of component (B1) yields the types of effects described above.

Furthermore, according to the resist composition of the present invention, a resist pattern having favorable lithography properties such as exposure margin (EL margin) and line width roughness (LWR) can be formed.

The larger the EL margin, the less the degree of variation in the pattern size that accompanies changes in the exposure dose, and the greater the process margin.

LWR refers to irregularity in the line width of a line pattern when a resist pattern is formed, and as the size of the pattern is reduced, improvements in the LWR value become increasingly important.

<<Method of Forming Resist Pattern>>

The method of forming a resist pattern according to the second aspect of the present invention includes: using the resist composition of the first aspect of the present invention described above to form a resist film on a substrate, conducting exposure of the resist film, and alkali-developing the resist film to form a resist pattern.

The method of forming a resist pattern according to the present invention can be conducted, for example, in the manner described below.

Firstly, the resist composition is applied to a substrate using a spinner or the like, and a prebake (post applied bake (PAB)) is conducted under temperature conditions of 80 to 150° C. for 40 to 120 seconds, and preferably 60 to 90 seconds, to form a resist film. The resist film is then selectively exposed to an ArF excimer laser beam through a desired mask pattern using an ArF exposure apparatus or the like, followed by post exposure baking (PEB) under temperature conditions of 80 to 150° C. for 40 to 120 seconds, and preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, a bake treatment (post bake) may be conducted following the alkali developing treatment. In this manner, a resist pattern that is faithful to the mask pattern can be obtained.

There are no particular limitations on the substrate, and a conventionally known substrate can be used. Examples of the substrate include substrates for electronic components, and such substrates having wiring patterns formed thereon. Specific examples of the material of the substrate include metals such as silicon wafer, copper, chromium, iron and aluminum, as well as glass. Suitable materials for the wiring pattern include copper, aluminum, nickel, and gold.

Further, any one of the above-exemplified substrates with an inorganic and/or organic film provided on the surface thereof may also be used as the substrate. Examples of the inorganic film include inorganic antireflection films (inorganic BARC), whereas examples of the organic film include organic antireflection films (organic BARC).

There are no particular limitations on the wavelength used for exposure, and radiation such as an ArF excimer laser, KrF excimer laser, $F_2$ excimer laser, extreme ultraviolet rays (EUV), vacuum ultraviolet rays (VUV), electron beam (EB), X-rays, and soft X-rays may be used.

The resist composition of the present invention is effective for use with a KrF excimer laser, ArF excimer laser, EB and EUV, and is particularly effective for use with an ArF excimer laser.

The exposure of the resist film may be either a general exposure (dry exposure) conducted in air or an inert gas such as nitrogen, or an immersion exposure (immersion lithography).

In immersion lithography, exposure is conducted in a state where the region between the lens and the resist film formed on a wafer (which is conventionally filled with air or an inert gas such as nitrogen) is filled with a solvent (an immersion medium) that has a larger refractive index than the refractive index of air.

More specifically, in immersion lithography, the region between the resist film formed in the above-described manner and the lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index that is larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C., and preferably from 80 to 160° C. A fluorine-based inert liquid having a boiling point within the above-mentioned range is advantageous in that the removal of the immersion medium after the exposure can be conducted by a simple method.

As the fluorine-based inert liquid, a perfluoroalkyl compound in which all of the hydrogen atoms of the alkyl group are substituted with fluorine atoms is particularly desirable. Examples of such perfluoroalkyl compounds include perfluoroalkyl ether compounds and perfluoroalkylamine compounds.

Specifically, one example of a suitable perfluoroalkyl ether compound is perfluoro(2-butyl-tetrahydrofuran) (boiling point 102° C.), and an example of a suitable perfluoroalkylamine compound is perfluorotributylamine (boiling point 174° C.).

In a method of forming a resist pattern that includes an immersion exposure step, the resist composition according to the first aspect of the present invention can be used favorably as the immersion exposure resist composition, and enables favorable lithography properties to be obtained. Further, in a method of forming a resist pattern that includes the formation of a 3-layer resist laminate, the resist composition of the present invention can be used favorably as the positive resist composition for forming the top layer resist film, and enables favorable lithography properties to be obtained.

Moreover, the resist composition of the present invention can also be applied to double exposure methods and double patterning methods.

<<Compound>>

The compound according to the third aspect of the present invention is a compound represented by general formula (b1) shown above.

The description of this compound of the present invention is the same as the description provided above in connection with the acid generator (B1) included in the component (B) of the resist composition according to the first aspect of the present invention.

(Method of Producing Compound)

The compound according to the third aspect of the present invention can be produced, for example, in the manner described below.

First, a compound represented by general formula (b1-15-01) shown below and a compound represented by general formula (b1-15-02) shown below are added to a solution of an organic acid $H^+B^-$ (wherein $B^-$ represents an organic acid anion moiety such as a methanesulfonate ion), and following reaction, pure water or an organic solvent (such as dichloromethane or tetrahydrofuran) is added to the reaction mixture. The organic layer is then extracted, and a compound represented by general formula (b1-15-03) shown below is obtained from the organic layer.

[Chemical Formula 56]

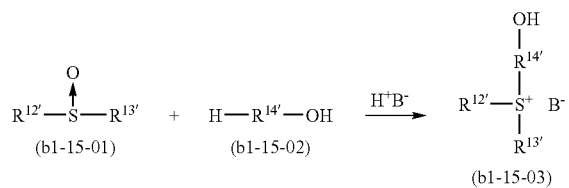

Subsequently, the compound represented by general formula (b1-15-03) is added to an organic solvent (such as dichloromethane or tetrahydrofuran) and cooled, a compound represented by general formula (b1-0-1) shown below is added to the cooled solution and reacted, and following phase separation and washing with water, a compound represented by general formula (b1-15-04) shown below is obtained from the organic layer.

The compound represented by general formula (b1-15-04) is then dissolved in a mixed solvent containing an organic solvent (such as dichloromethane or tetrahydrofuran) and water, an alkali metal (L) salt (wherein $L^+$ represents an alkali metal cation such as a lithium ion, sodium ion or potassium ion) of the desired anion ($X-C(=O)-O-Y^1-SO_3^-$) is added to the mixed solvent solution and reacted, and following phase separation and washing with water, a compound (b1) is obtained from the organic layer.

[Chemical Formula 57]

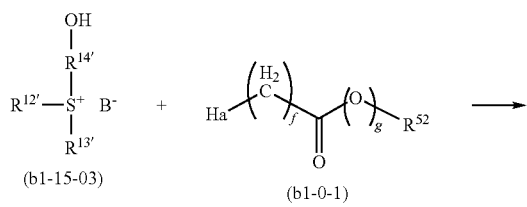

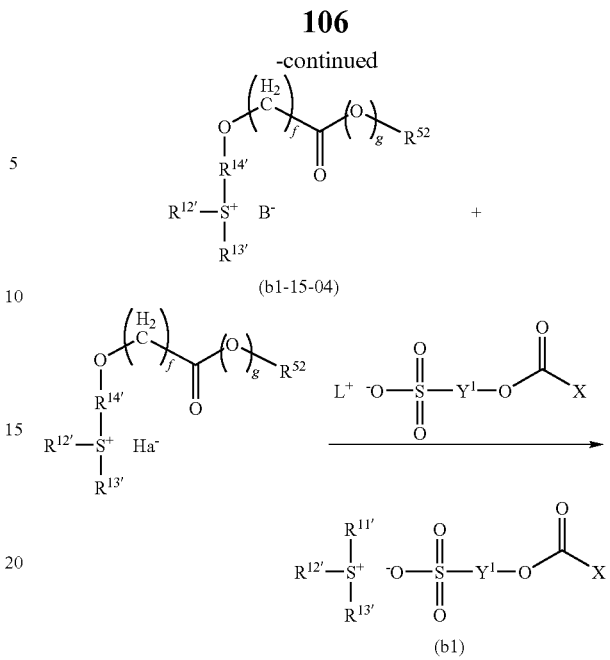

wherein $R^{12'}$ and $R^{13'}$ are as defined above for $R^{12'}$ and $R^{13'}$ in general formula (b1), $R^{14'}$ represents an arylene group obtained by removing one hydrogen atom from the aryl group $R^{11'}$ defined above in general formula (b1), $B^-$ represents the anion moiety of an organic acid, $L^+$ represents an alkali metal cation, $R^{52}$, f and g are as defined above for $R^{52}$, f and g in general formula (b1-0), Ha represents a halogen atom, and $Ha^-$ represents a halide ion.

The compound represented by general formula (b1-15-04) is a mixture of a compound containing the organic acid anion moiety ($B^-$) and a compound containing the halide ion ($Ha^-$) as the anion moiety, but by reacting the mixture with the alkali metal salt ($L^+.X-C(=O)-O-Y^1-SO_3^-$), both of the anion moieties are substituted with the $X-C(=O)-O-Y^1-SO_3^-$ ion.

<<Acid Generator>>

The acid generator according to the fourth aspect of the present invention consists of a compound represented by general formula (b1).

This acid generator is useful as the acid generator for a chemically amplified resist composition, such as the acid generator component (B) of the above-mentioned resist composition according to the first aspect of the present invention.

EXAMPLES

A more detailed description of the present invention is presented below using a series of examples, although the scope of the present invention is in no way limited by these examples.

Synthesis Example 1

Synthesis of 2-(2-(2-methyl-2-adamantyloxy)-2-oxoethoxy)-2-oxoethanol

A 2 liter 3-neck flask fitted with a thermometer, a cooling tube and a stirrer was charged with 37.6 g (494 mmol) of glycolic acid, 700 ml of DMF, 86.5 g (626 mmol) of potassium carbonate and 28.3 g (170 mmol) of potassium iodide, and the resulting mixture was stirred for 30 minutes at room temperature. Subsequently, 300 ml of a dimethylformamide solution containing 100 g (412 mmol) of 2-methyl-2-adamantyl chloroacetate was added gradually to the reaction mixture. The temperature was then raised to 40° C., and the reaction mixture was stirred at that temperature for 4 hours. Following completion of the reaction, 2,000 ml of diethyl ether was added, the solution was filtered, and the filtrate was washed 3 times with 500 ml samples of distilled water. Crystallization was then performed using a mixed solution of toluene (300 ml) and heptane (200 ml), yielding 78 g (yield: 67%, GC purity: 99%) of the targeted colorless solid.

The results of instrumental analysis of the obtained compound are listed below.

$^1$H-NMR: 1.59 (d, 2H, J=12.5 Hz), 1.64 (s, 3H), 1.71 to 1.99 (m, 10H), 2.29 (m, 2H), 2.63 (t, 1H, J=5.2 Hz), 4.29 (d, 2H, J=5.2 Hz), 4.67 (s, 2H).

$^{13}$C-NMR: 22.35, 26.56, 27.26, 32.97, 34.54, 36.29, 38.05, 60.54, 61.50, 89.87, 165.97, 172.81.

GC-MS: 282 (M+, 0.02%), 165 (0.09%), 149 (40%), 148 (100%), 133 (22%), 117 (2.57%), 89 (0.40%).

The above results confirmed that the obtained compound was 2-(2-(2-methyl-2-adamantyloxy)-2-oxoethoxy)-2-oxoethanol.

Synthesis Example 2

Synthesis of 2-(2-(2-methyl-2-adamantyloxy)-2-oxoethoxy)-2-oxoethyl methacrylate (Compound 3)

A 2 liter 3-neck flask fitted with a thermometer, a cooling tube and a stirrer was charged with 165 g (584 mmol) of 2-(2-(2-methyl-2-adamantyloxy)-2-oxoethoxy)-2-oxoethanol, 2,000 ml of THF, 105 ml (754 mmol) of triethylamine and 0.165 g (1,000 ppm) of p-methoxyphenol, and the mixture was stirred to form a solution. Following dissolution, the solution was cooled in an ice bath and 62.7 ml (648 mmol) of methacryloyl chloride was added gradually to the solution. The reaction mixture was then returned to room temperature, and stirred for 3 hours. Following completion of the reaction, 1,000 ml of diethyl ether was added, and the filtrate was washed 5 times with 200 ml samples of distilled water. The washed extract was then concentrated, yielding 198 g (yield: 97%, GC purity: 99%) of the targeted colorless liquid.

The results of instrumental analysis of the obtained compound 3 are listed below.

$^1$H-NMR: 1.58 (d, J=12.5 Hz, 2H), 1.63 (s, 3H), 1.71 to 1.89 (m, 8H), 1.98 (s, 3H), 2.00 (m, 2H), 2.30 (m, 2H), 4.62 (s, 2H), 4.80 (s, 2H), 5.66 (m, 1H), 6.23 (m, 1H).

$^{13}$C-NMR: 18.04, 22.15, 26.42, 27.14, 32.82, 34.38, 36.11, 37.92, 60.44, 61.28, 89.42, 126.79, 135.18, 165.61, 166.30, 167.20.

GC-MS: 350 (M+, 1.4%), 206 (0.13%), 149 (47%), 148 (100%), 133 (20%), 69 (37%).

Production Example 1

Synthesis of Polymer Compound (1)

A 500 ml beaker was charged with 3.42 g (20.11 mmol) of [compound 1] shown below, 11.99 g (45.71 mmol) of [compound 2] shown below, 5.22 g (15.54 mmol) of [compound 3] obtained from the above synthesis example 2 and shown below, and 1.73 g (7.31 mmol) of [compound 4] shown below, and these compounds were then dissolved in 105.48 g of methyl ethyl ketone. To the resulting solution was added and dissolved 2.2 mmol of dimethyl azobisisobutyrate (V-601) as a polymerization initiator. This reaction solution was then added dropwise over 6 hours and under an atmosphere of nitrogen to 43.95 g of methyl ethyl ketone heated to 75° C. in a separable flask. Following completion of the dropwise addition, the reaction solution was stirred under heat for one hour and then cooled to room temperature. The thus obtained polymerization reaction solution was concentrated under reduced pressure, and then added dropwise to a large volume of a mixed solvent of methanol and water, thereby precipitating the reaction product (copolymer). The precipitated reaction product was filtered, washed and dried, yielding 20 g of the target polymer compound (1).

The weight average molecular weight (Mw) of this polymer compound (1), measured by GPC and referenced against standard polystyrenes, was 7,800, and the dispersity (Mw/Mn) was 1.59.

Furthermore, measurement of the carbon-13 nuclear magnetic resonance spectrum at 600 MHz (600 MHz $^{13}$C-NMR) revealed a copolymer composition (the proportions (molar ratios) for each of the structural units shown in the structural formula below) in which 1/m/n/o=30/50/10/10.

[Chemical Formula 58]

[Compound 1]

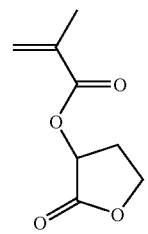

[Compound 2]

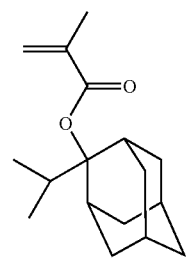

[Compound 3]

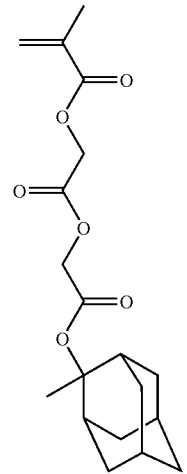

[Compound 4]

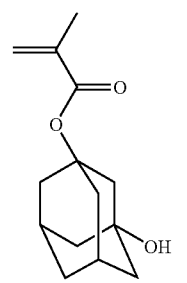

-continued

[Chemical Formula 59]

Polymer compound (1)

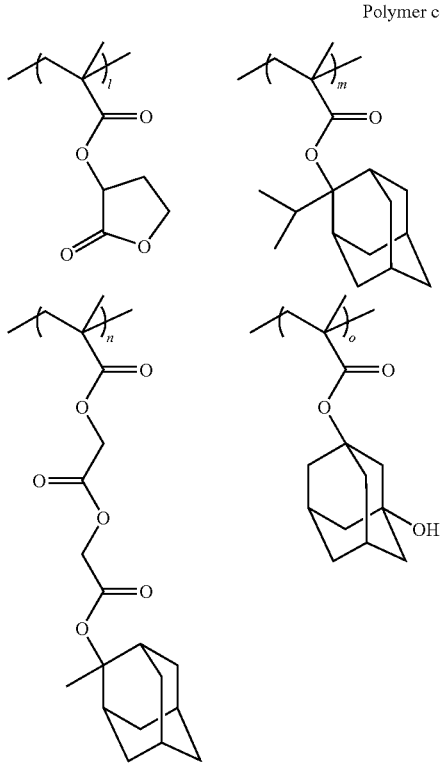

Synthesis Example 3

Synthesis of Compound (IX)

35.6 g of a compound (VII) (TDPS-Br) was dissolved in 360 g of pure water, 360 g of dichloromethane and 38.0 g of a compound (VIII) were added to the solution, and the resulting mixture was stirred for 14 hours at room temperature. Subsequently, the dichloromethane layer was separated, washed with dilute hydrochloric acid, and then washed with water. The dichloromethane layer was then solidified by concentration, yielding the target compound (IX) (58 g) as a white solid.

[Chemical Formula 60]

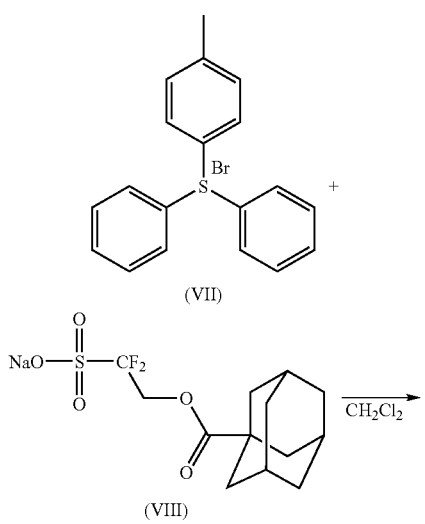

-continued

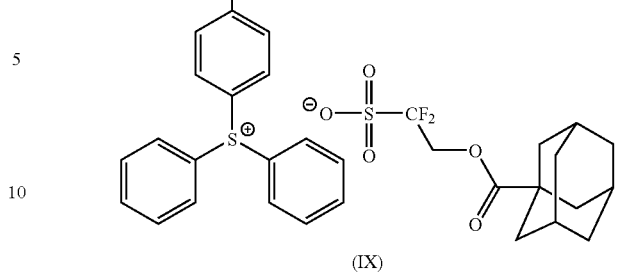

(IX)

This compound (IX) was analyzed by NMR.

$^1$H-NMR (DMSO-d6, 400 MHz): δ (ppm)=1.64 (m, 6H, Ad), 1.82 (m, 6H, Ad), 1.94 (m, 3H, Ad), 3.35 (s, 3H, CH$_3$), 4.55 (t, 2H, CF$_2$CH$_2$), 7.56 (d, 2H, Ar), 7.72 to 7.84 (m, 12H, Ar).

$^{19}$F-NMR (DMSO-d6, 376 MHz): δ (ppm)=−111.2.

The above analysis results confirmed that the compound (IX) had the structure shown above in the chemical formula (IX).

Synthesis Example 4

Synthesis of Compound (IV)

To methanesulfonic acid (60.75 g) controlled at a temperature of not more than 20° C. were gradually added phosphorus oxide (8.53 g), 2,6-dimethylphenol (8.81 g) and diphenylsulfoxide (12.2 g). Following maturing for 30 minutes with the temperature maintained within a range from 15 to 20° C., the temperature was raised to 40° C. and the reaction mixture was matured at that temperature for 2 hours. Subsequently, the reaction liquid was added dropwise to pure water (109.35 g) that had been cooled to 15° C. or lower. Following completion of this dropwise addition, dichloromethane (54.68 g) was added, and following thorough stirring, the dichloromethane layer was collected. A separate vessel was charged with hexane (386.86 g) at 20 to 25° C., and the dichloromethane layer was added dropwise to the hexane. Following completion of the dropwise addition and subsequent maturing for 30 minutes at 20 to 25° C., the mixture was filtered to obtain the compound (IV) (yield: 70.9%).

[Chemical Formula 61]

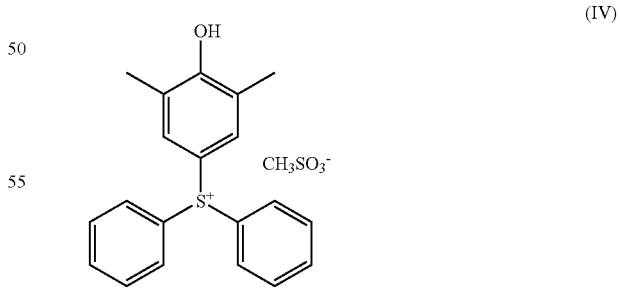

Synthesis Example 5

Synthesis of Compound (V)

A 3-neck flask was charged with 8.05 g of the compound (IV) and 56.4 g of dichloromethane, and the mixture was stirred. To the resulting mixture was added dropwise a mixed solution of triethylamine (2.63 g) and dichloromethane (8.05 g), and the temperature was cooled to 10° C. Subsequently, a mixed solution of 1-adamantanecarbonyl chloride (4.77 g) and dichloromethane (16.10 g) was added dropwise to the flask, and the resulting mixture was then stirred for 3 hours at room temperature. The organic phase was washed with a 1% by weight aqueous solution of hydrochloric acid and then with pure water, and the washed dichloromethane phase was then concentrated and dried to obtain 11.0 g of the target compound (V).

The counter anion of the obtained compound (V) was a mixture of methanesulfonate ions and chloride ions. Analysis of the compositional ratio between the ions by ion chromatography revealed a result of $CH_3SO_3/Cl=64.4/35.6$ (wt %).

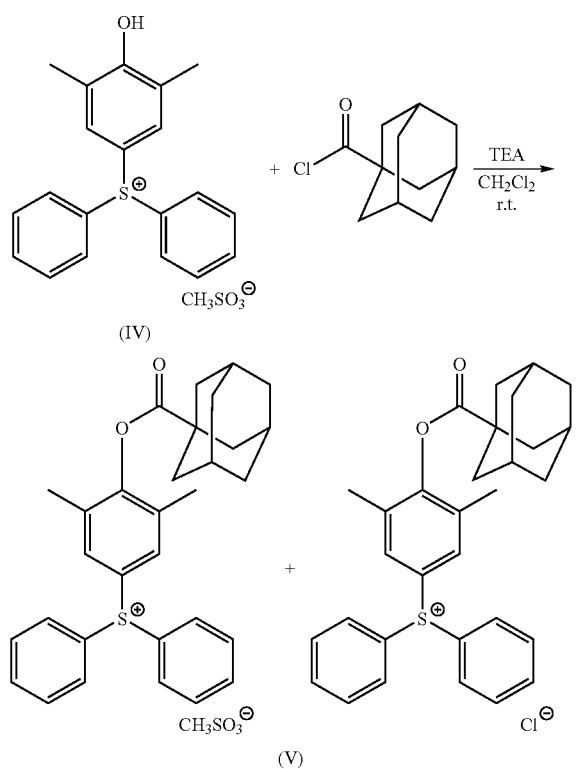

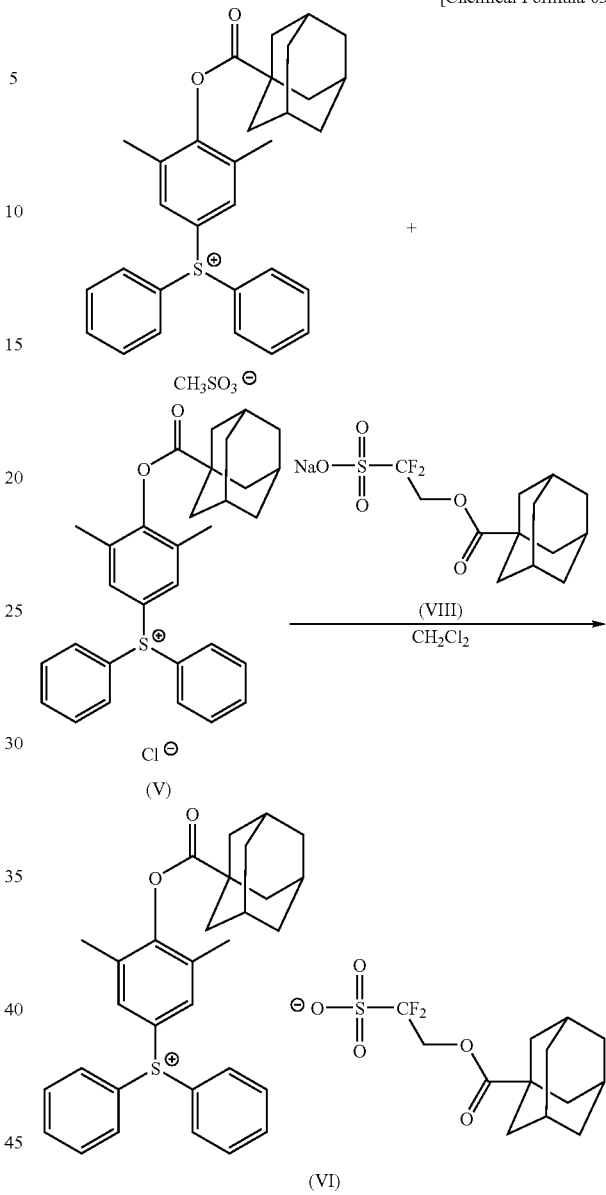

Synthesis Example 6

Synthesis of Compound (VI)

21.0 g of the compound (V) was dissolved in 129.0 g of pure water, dichloromethane (160.1 g) and the compound (VIII) (16.8 g) were added to the solution, and the resulting mixture was stirred for one hour at room temperature. Subsequently, the dichloromethane layer was separated, washed with dilute hydrochloric acid, and then washed with water. The dichloromethane layer was then concentrated and solidified to obtain the target compound (VI) (29.3 g) as a white solid.

This compound (VI) was analyzed by NMR.
$^1$H-NMR (DMSO, 400 MHz): δ (ppm)=7.75 to 7.86 (m, 10H, Ar), 7.68 (s, 2H, Ar), 4.55 (t, 2H, $CF_2CH_2$), 2.13 (s, 6H, $CH_3$), 1.62 to 2.03 (m, 30H, Adamantane).
$^{19}$F-NMR (DMSO, 376 MHz): δ (ppm)=−111.4.

The above analysis results confirmed that the compound (VI) had the structure shown above in the chemical formula (VI).

Synthesis Example 7

Synthesis of Compound (II)

5.87 g of the compound (I), 41.85 g of dichloromethane and 20.93 g of pure water were placed in a beaker, 4.16 g of the above-mentioned compound (VIII) was added, and the resulting mixture was stirred for one hour at room temperature. Subsequently, the reaction liquid was separated, and the organic layer was washed with dilute hydrochloric acid and then with water. The thus obtained organic layer was added dropwise to 249.0 g of n-hexane, yielding 6.70 g of the target compound (II) as a white powder.

The counter anion of the compound (I) was a mixture of bromide (Br) ions and chloride (Cl) ions. Analysis of the compositional ratio between the ions by ion chromatography revealed a result of Br/Cl=84/16 (wt %).

[Chemical Formula 64]

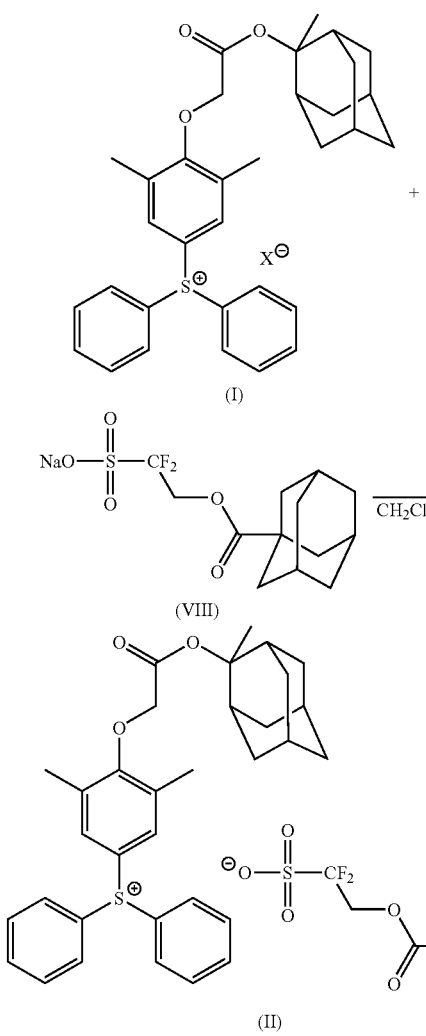

This compound (II) was analyzed by NMR.
$^1$H-NMR (DMSO-d6, 400 MHz): δ (ppm)=1.07 to 1.97 (m, 30H, Ad+CH$_3$), 2.21 (s, 2H, Ad), 2.31 (s, 6H, Ar—CH$_3$), 4.54 (s, 2H, OCH$_2$), 4.59 (s, 2H, CF$_2$CH$_2$), 7.61 (s, 2H, Ar), 7.72 to 7.83 (m, 10H, Ar).
$^{19}$F-NMR (DMSO-d6, 376 MHz): δ (ppm)=−111.3.

The above analysis results confirmed that the compound (II) had the structure shown above in the chemical formula (II).

Synthesis Example 8

Synthesis of Compound (5-1)

Under an atmosphere of nitrogen, a 3-neck flask was charged with the compound (IV) (154.06 g) and acetonitrile (1142.23 g), and the mixture was stirred to form a uniform solution. Potassium carbonate (249.04 g) was added to the solution, the mixture was stirred for 10 minutes at room temperature, a solution containing the compound (6) (65.13 g) dissolved in acetonitrile (195.38 g) was added dropwise to the flask, and the resulting mixture was reacted under reflux for 24 hours. Following completion of the reaction, the potassium carbonate was removed by filtration, the organic layer was washed with water, and the acetonitrile was removed by evaporation under reduced pressure. The resulting oily substance was dissolved in dichloromethane (2175.95 g), the organic layer was washed 4 times with water, and the solvent was then removed by evaporation under reduced pressure, yielding a total of 150.00 g of compounds (5-1) and (5-2).

The counter anions of the obtained mixture of compounds (5-1) and (5-2) were a mixture of chloride ions and methanesulfonate ions. Analysis of the compositional ratio between the ions by ion chromatography revealed a result of Cl/CH$_3$SO$_3$=60.0/40.0 (wt %).

[Chemical Formula 65]

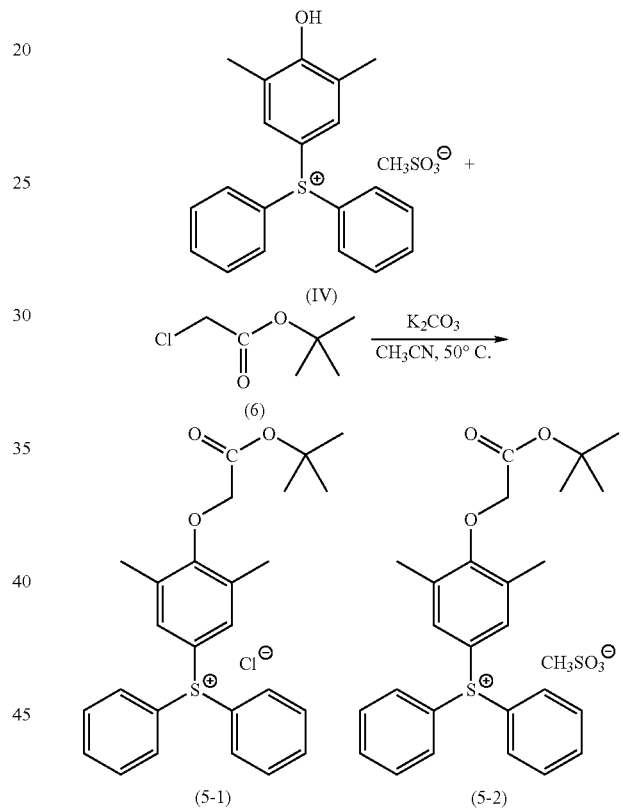

These compounds (5-1) and (5-2) were analyzed by NMR.
$^1$H-NMR (DMSO-d6, 400 MHz): δ (ppm)=7.75 to 7.86 (m, 10H, Aryl), 7.63 (s, 2H, Aryl), 4.55 (s, 2H, —CO—CH$_2$—O—), 2.30 (s, 7.2H, Aryl—CH$_3$, CH$_3$SO$_3$—), 1.43 (s, 9H, t-butyl).

The above analysis results confirmed that the compounds had the structures shown above in the chemical formulas (5-1) and (5-2).

Synthesis Example 9

Synthesis of Compound (7)

The compound (5-1) (2 g) was added to a mixture of dichloromethane (20 g) and water (20 g), and the resulting mixture was stirred. Subsequently, the compound (VIII) (1.63 g) was added, and the resulting mixture was stirred for one hour. Following separation of the reaction liquid, the organic layer was washed 4 times with water (20 g). The washed organic solvent layer was then concentrated and solidified to obtain 2 g of the compound (7).

[Chemical Formula 66]

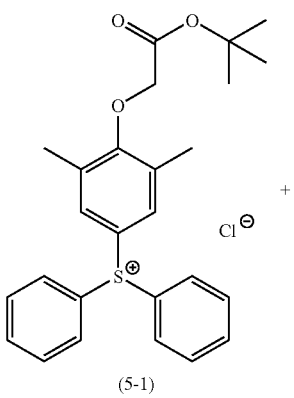

(5-1)

-continued

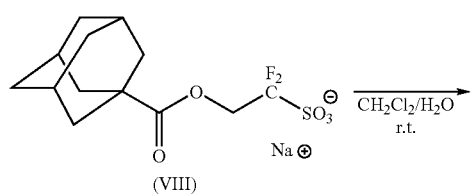

(VIII)

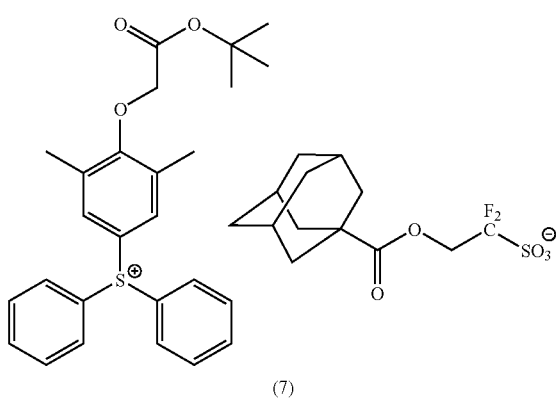

(7)

This compound (7) was analyzed by NMR.

$^1$H-NMR (DMSO-d6, 400 MHz): δ (ppm)=7.79 (m, 10H, Ar), 7.62 (s, 2H, Ar), 4.54 (s, 2H, —CO—CH$_2$—O—), 4.19 (s, 2H, CH$_2$), 2.30 (s, 6H, Ar—CH$_3$), 1.55 to 1.87 (m, 15H, adamantane), 1.43 (s, 9H, t-butyl).

$^{19}$F-NMR (DMSO-d6, 376 MHz): δ (ppm)=−77.7.

The above analysis results confirmed that the compound (7) had the structure shown above in the chemical formula (7).

<Resist Composition Preparation (1)>

Reference Example 1, Examples 1 and 2, Comparative Example 1

The components shown in Table 1 were mixed together and dissolved to obtain positive resist compositions.

TABLE 1

| | Composition [parts by weight] | | | | | Target size (nm) | | |
| --- | --- | --- | --- | --- | --- | --- | --- | --- |
| | Component (A) | Component (B) | Component (D) | Component (S) | PAB/PEB (° C.) | (hole diameter/ pitch) | Sensitivity (mJ/cm$^2$) | Shape |
| Reference example 1 | (A)-1 [100] | (B)-1 [10.0] | (D)-1 [1.0] | (S)-1 [2400] | 90/85 | 85/135 | 30.9 | Δ |
| Example 1 | (A)-1 [100] | (B)-2 [14.0] | (D)-1 [1.0] | (S)-1 [2400] | 90/85 | 85/135 | 32.7 | ◯ |
| Example 2 | (A)-1 [100] | (B)-3 [14.0] | (D)-1 [1.0] | (S)-1 [2400] | 90/85 | 85/135 | 34.0 | ◯ |
| Comparative example 1 | (A)-1 [100] | (B)-4 [9.5] | (D)-1 [1.0] | (S)-1 [2400] | 90/85 | 85/135 | 26.3 | X |

In Table 1, the values in brackets [ ] indicate the amount (in terms of parts by weight) of the component added. Further, the reference characters indicate the following.

(A)-1: the aforementioned polymer compound (1)
(B)-1: the aforementioned compound (IX)
(B)-2: the aforementioned compound (VI)
(B)-3: the aforementioned compound (II)
(B)-4: (4-methylphenyl)diphenylsulfonium nonafluoro-n-butanesulfonate
(D)-1: stearyldiethanolamine
(S)-1: a mixed solvent of PGMEA/PGME=6/4 (weight ratio)

<Evaluation of Lithography Properties (1)>

Using the obtained resist compositions, resist patterns were formed using the procedure outlined below, and the lithography properties were evaluated.

[Resolution•Sensitivity]

An organic anti-reflection film composition (product name: ARC29, manufactured by Brewer Science Ltd.) was applied onto an 12-inch silicon wafer using a spinner, and the composition was then baked and dried on a hotplate at 205° C. for 60 seconds, thereby forming an organic anti-reflection film having a film thickness of 85 nm. Then, each of the resist compositions obtained above in reference example 1, examples 1 to 2 and comparative example 1 was applied onto such an anti-reflection film using a spinner, and was then prebaked (PAB) on a hotplate at 90° C. for 60 seconds and dried, thereby forming a resist film having a film thickness of 120 nm.

Subsequently, using an ArF exposure apparatus (product name: NSR-S308F, manufactured by Nikon Corporation, NA (numerical aperture)=0.92, ⅔ annular illumination), the resist film was selectively irradiated with an ArF excimer laser (193 nm) through a mask pattern (6% halftone) designed for targeting a contact hole pattern with the target size (hole diameter (nm)/pitch (nm)) shown in Table 1.

Next, a PEB treatment was conducted at 85° C. for 60 seconds, followed by alkali developing for 30 seconds at 23° C. in a 2.38% by weight aqueous solution of TMAH (product name: NMD-W, manufactured by Tokyo Ohka Kogyo Co., Ltd.). Then, the resist film was rinsed for 25 seconds with pure water, and then shaken dry.

As a result, a contact hole pattern having a hole diameter of 85 nm and a pitch of 135 nm was formed on the resist film formed from the resist composition of each example.

Further, the optimum exposure dose Eop (mJ/cm$^2$), namely the sensitivity, is also shown in Table 1.

[Evaluation of Circularity]

Each of the contact hole patterns formed in the manner outlined above was inspected from directly above using a scanning electron microscope (SEM), and the circularity of the hole pattern was evaluated against the criteria listed below. The results of the evaluation are shown in Table 1.

O: the entire hole pattern had a favorable shape, with a high degree or circularity.

Δ: portions of the hole pattern exhibited distortions, and the circularity was inferior.

x: the entire hole pattern was covered with distortions, some portions of the pattern were defective, and some adjacent hole patterns were joined.

[Evaluation of CD Uniformity (CDU)]

For a contact hole (C/H) pattern formed at the above Eop value, the diameters (CD) of 25 holes were measured in each C/H pattern, and the value of 3 times the standard deviation (σ) calculated from the measurement results (namely, 3σ) was determined and used as an evaluation of the CD uniformity (CDU).

The smaller the value of 3σ determined in this manner, the higher the degree of CD uniformity (CDU) for each hole formed within the resist film.

The results of this evaluation revealed a value of 10.17 for reference example 1, a value of 9.17 for example 1, a value of 9.50 for example 2, and a value of 12.60 for comparative example 1.

The results confirmed that by using a resist composition according to the present invention, a contact hole pattern having a hole diameter of 85 nm and a pitch of 135 nm, which represents a very fine pattern of less than 100 nm that also has a narrow pitch, was able to be formed with a high degree of circularity and a favorable resist pattern shape.

Accordingly, it was confirmed that a resist composition containing a compound of the present invention as an acid generator, and a method of forming a resist pattern that employs such a resist composition are capable of forming a resist pattern of superior shape.

<Resist Composition Preparation (2)>

Examples 3 and 4, Comparative Example 2

The components shown in Table 2 were mixed together and dissolved to obtain positive resist compositions.

TABLE 2

|  | Component (A) | Component (B) | Component (D) | Component (E) | Component (S) | |
|---|---|---|---|---|---|---|
| Comparative example 2 | (A)-2 [100] | (B)-4 [4.8] | (D)-2 [0.75] | (E)-1 [0.75] | (S)-1 [2400] | (S)-2 [10] |
| Example 3 | (A)-2 [100] | (B)-3 [6.19] | (D)-2 [0.75] | (E)-1 [0.75] | (S)-1 [2400] | (S)-2 [10] |
| Example 4 | (A)-2 [100] | (B)-5 [6.96] | (D)-2 [0.75] | (E)-1 [0.75] | (S)-1 [2400] | (S)-2 [10] |

In Table 2, the values in brackets [ ] indicate the amount (in terms of parts by weight) of the component added. Further, the reference characters indicate the following.

(A)-2: a copolymer represented by chemical formula (a1-12-1) shown below, with Mw=7,000 and Mw/Mn=1.5.

In the chemical formula (A1-12-1), the subscripts a11, a12, a2 and a3 indicate the proportion (molar ratio) of each of the structural units that constitute the copolymer, and a2/a11/a12/a3=40/25/25/10.

This copolymer is obtained by a conventional radical polymerization of α-methacryloyloxy-γ-butyrolactone, 1-ethyl-1-cyclohexyl methacrylate, 1-methyl-1-cyclopentyl methacrylate, and 3-hydroxy-1-adamantyl methacrylate.

[Chemical Formula 67]

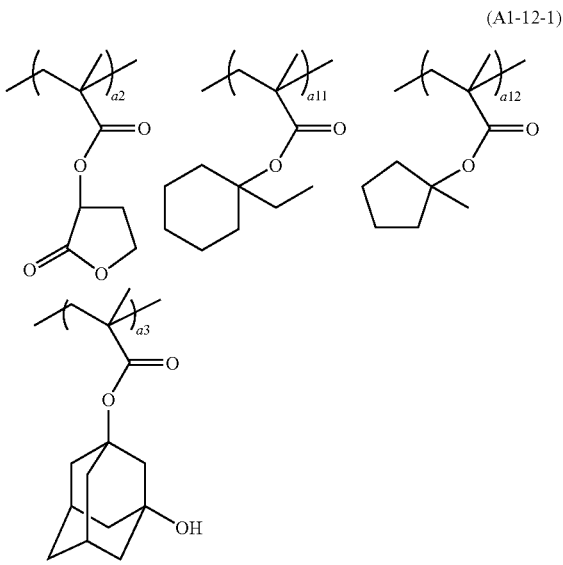

(A1-12-1)

(B)-3: the aforementioned compound (II)
(B)-4: (4-methylphenyl)diphenylsulfonium nonafluoro-n-butanesulfonate
(B)-5: the aforementioned compound (7)
(D)-2: tri-n-pentylamine
(E)-1: salicylic acid
(S)-1: a mixed solvent of PGMEA/PGME=6/4 (weight ratio)
(S)-2: γ-butyrolactone <Evaluation of Lithography Properties (2)>

Using the obtained resist compositions, resist patterns were formed using the procedure outlined below, and the lithography properties were evaluated.

[Resolution•sensitivity]

An organic anti-reflection film composition (product name: ARC29, manufactured by Brewer Science Ltd.) was applied onto an 8-inch silicon wafer using a spinner, and the composition was then baked and dried on a hotplate at 205° C. for 60 seconds, thereby forming an organic anti-reflection film having a film thickness of 77 nm. Then, each of the resist compositions prepared above was applied onto such an anti-reflection film using a spinner, and was then prebaked (PAB) on a hotplate at 90° C. for 60 seconds and dried, thereby forming a resist film having a film thickness of 150 nm.

Subsequently, using an ArF exposure apparatus (product name: NSR-S302B, manufactured by Nikon Corporation, NA (numerical aperture)=0.60, ⅔ annular illumination), the resist film was selectively irradiated with an ArF excimer laser (193 nm) through a 6% halftone mask pattern.

Next, a PEB treatment was conducted at 90° C. for 60 seconds, followed by alkali developing for 30 seconds at 23° C. in a 2.38% by weight aqueous solution of TMAH (product name: NMD-3, manufactured by Tokyo Ohka Kogyo Co., Ltd.). Then, the resist film was rinsed for 30 seconds with pure water, shaken dry, and then subjected to a post bake treatment at 100° C. for 60 seconds.

As a result, a line and space pattern (hereafter abbreviated as "LS pattern") having a line width of 130 nm and a pitch of 260 nm was formed on each resist film.

Further, the sensitivity for formation of this 130 nm LS pattern was recorded as the optimum exposure dose Eop (mJ/cm$^2$). The sensitivity (Eop) for each positive resist composition is shown in Table 3.

[Evaluation of EL Margin]

The range of exposure doses for which the LS pattern was able to be formed with a line width that was within ±5% of the target dimension (line width: 130 nm) (namely, a line width within a range from 123.5 nm to 136.5 nm) was determined, and the EL margin (units: %) was then calculated using the following equation. The results are shown in Table 3.

$$EL\ margin\ (\%) = (|E1-E2|/Eop) \times 100$$

E1 represents the exposure dose (mJ/cm$^2$) that results in the formation of the LS pattern with a line width of 123.5 nm, whereas E2 represents the exposure dose (mJ/cm$^2$) that results in the formation of the LS pattern with a line width of 136.5 nm.

[Evaluation of LWR (Line Width Roughness)]

In the LS pattern of line width 130 nm and pitch 260 nm formed at the Eop value described above, the line width was measured at 5 locations along the lengthwise direction of the line using a measuring SEM (scanning electron microscope, accelerating voltage: 800 V, product name: S-9220, manufactured by Hitachi, Ltd.). From these results, the value of 3 times the standard deviation (s) (namely, 3 s) was calculated as a indicator of the LWR. The results are shown in Table 3. The smaller this 3 s value is, the lower the level of roughness within the line width, indicating the formation of a LS pattern of more uniform width.

TABLE 3

|  | PAB/PEB (° C.) | Target size (nm) Line width/pitch | Sensitivity (mJ/cm$^2$) | EL margin (%) | LWR (nm) |
|---|---|---|---|---|---|
| Comparative example 2 | 90/90 | 130/260 | 17.5 | 5.82 | 10.32 |
| Example 3 | 90/90 | 130/260 | 36.6 | 7.76 | 7.82 |
| Example 4 | 90/90 | 130/260 | 36.8 | 7.19 | 7.80 |

The above results confirmed that compared with the resist composition of comparative example 2, the resist compositions of examples 3 and 4 according to the present invention exhibited a larger EL margin, and a smaller LWR value, indicating superior lithography properties.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition, comprising a base component (A) that exhibits changed solubility in an alkali developing solution under action of acid, and an acid generator component (B) that generates acid upon exposure,
said acid generator component (B) comprising an acid generator (B1) represented by general formula (b1) shown below:

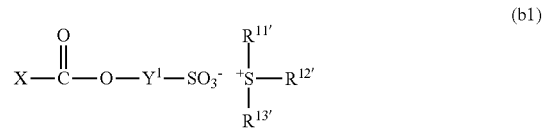

(b1)

wherein Y$^1$ represents a fluorinated alkylene group of 1 to 4 carbon atoms that may have a substituent, X represents an aliphatic cyclic group of 3 to 30 carbon atoms that may have a substituent, R$^{11'}$ to R$^{13'}$ each independently represents an aryl group or alkyl group that may have a substituent, provided that at least one of R$^{11'}$ to R$^{13'}$ is an aryl group having a substituent represented by general formula (b1-0) shown below, and two alkyl groups among R$^{11'}$ to R$^{13'}$ may be bonded to each other to form a ring with a sulfur atom in formula (b1),

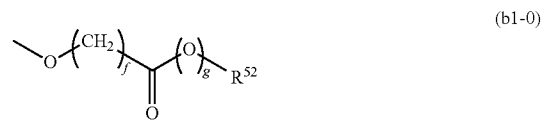

(b1-0)

wherein R$^{52}$ represents a cyclic saturated hydrocarbon group which is a polycyclic or monocyclic group of 3 to 20 carbon atoms and may have a substituent, f represents 0 or 1, and g represents 0 or 1.

2. The resist composition according to claim 1, wherein said base component (A) is a base component that exhibits increased solubility in an alkali developing solution under action of acid.

3. The resist composition according to claim 2, wherein said base component (A) comprises a resin component (A1) that exhibits increased solubility in an alkali developing solution under action of acid, and said resin component (A1) has a structural unit (a1) derived from an acrylate ester containing an acid-dissociable, dissolution-inhibiting group.

4. The resist composition according to claim 3, wherein said resin component (A1) further has a structural unit (a2) derived from an acrylate ester containing a lactone-containing cyclic group.

5. The resist composition according to claim 4, wherein said resin component (A1) further has a structural unit (a3) derived from an acrylate ester containing a polar group-containing aliphatic hydrocarbon group.

6. The resist composition according to claim 3, wherein said resin component (A1) further has a structural unit (a3) derived from an acrylate ester containing a polar group-containing aliphatic hydrocarbon group.

7. The resist composition according to claim 1, further comprising a nitrogen-containing organic compound (D).

8. A method of forming a resist pattern, comprising: using a resist composition according to claim 1 to form a resist film on a substrate, conducting exposure of said resist film, and alkali-developing said resist film to form a resist pattern.

9. A resist composition according to claim 1, wherein the cation moiety of the component (B1) is any one represented by the following formula:

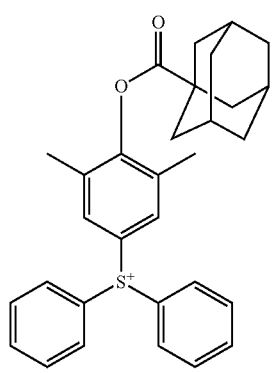
(b1-1c-1)

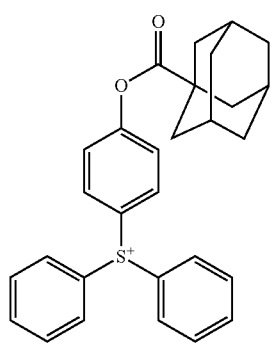
(b1-1c-2)

-continued

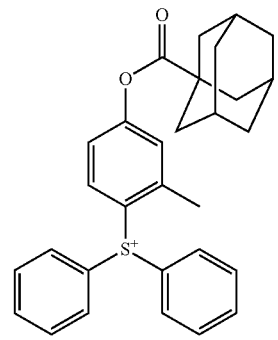
(b1-1c-3)

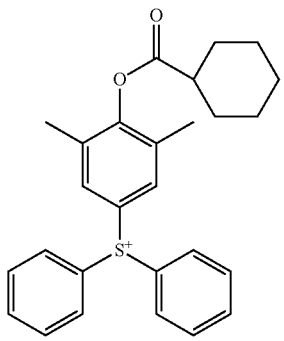
(b1-1c-4)

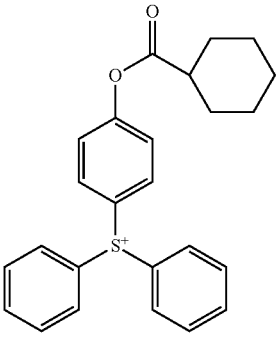
(b1-1c-5)

10. A resist composition according to claim 1, wherein the cation moiety of the component (B1) is any one represented by the following formula:

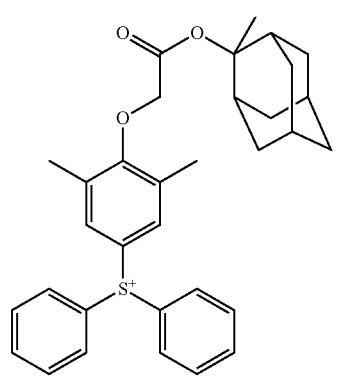
(b1-2c-1)

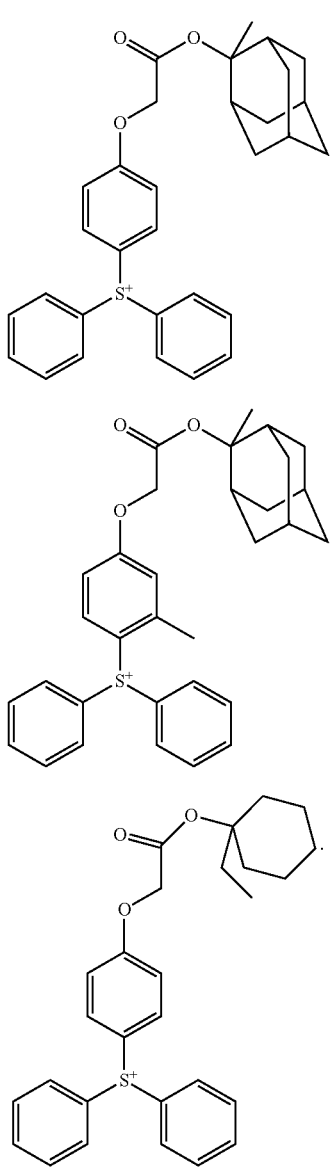

11. A compound represented by general formula (b1) shown below:

(b1)

$$X-\overset{O}{\underset{\|}{C}}-O-Y^1-SO_3^- \quad \overset{R^{11'}}{\underset{R^{13'}}{\overset{|}{{}^+S}-R^{12'}}}$$

wherein $Y^1$ represents a fluorinated alkylene group of 1 to 4 carbon atoms that may have a substituent, X represents an aliphatic cyclic group of 3 to 30 carbon atoms that may have a substituent, $R^{11'}$ to $R^{13'}$ each independently represents an aryl group or alkyl group that may have a substituent, provided that at least one of $R^{11'}$ to $R^{13'}$ is an aryl group having a substituent represented by general formula (b1-0) shown below, and two alkyl groups among $R^{11'}$ to $R^{13'}$ may be bonded to each other to form a ring with a sulfur atom in formula (b1),

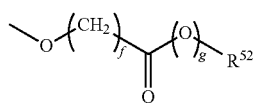

(b1-0)

wherein $R^{52}$ represents a cyclic saturated hydrocarbon group which is a polycyclic or monocyclic group of 3 to 20 carbon atoms and may have a substituent, f represents 0 or 1, and g represents 0 or 1.

12. An acid generator consisting of a compound of claim 11.

13. A compound according to claim 11, wherein the cation moiety of the compound is any one represented by the following formula:

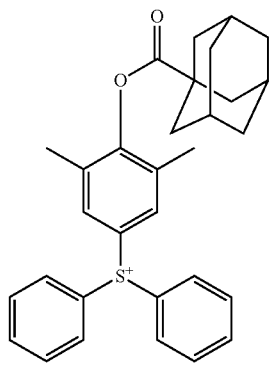

(b1-1c-1)

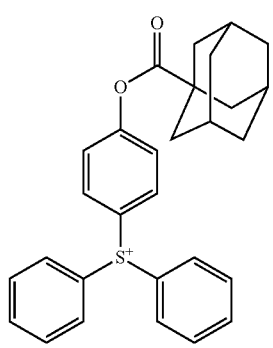

(b1-1c-2)

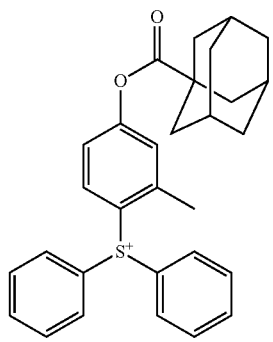

(b1-1c-3)

-continued
(b1-1c-4)
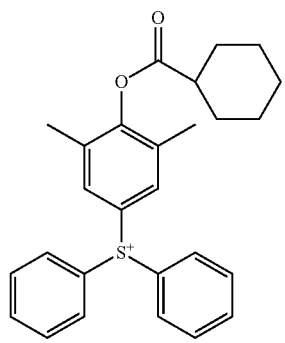
(b1-1c-5)
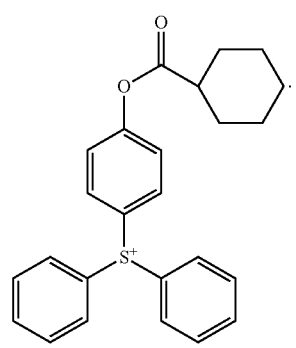
14. A compound according to claim 11, wherein the cation moiety of the compound is any one represented by the following formula:
(b1-2c-1)
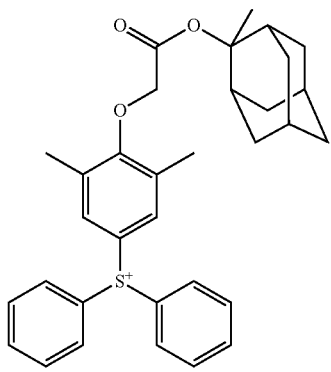
-continued
(b1-2c-2)
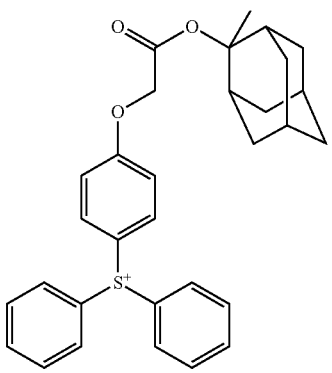
(b1-2c-3)
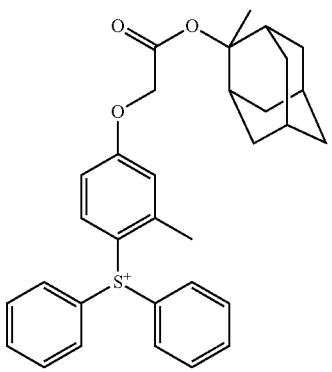
(b1-2c-5)
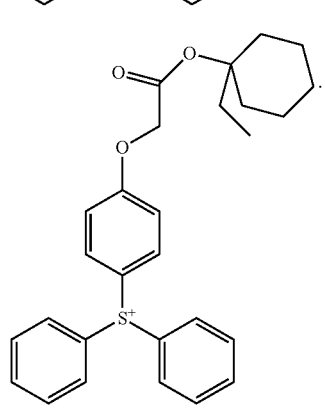
* * * * *

UNITED STATES PATENT AND TRADEMARK OFFICE
CERTIFICATE OF CORRECTION

PATENT NO.        : 8,247,160 B2
APPLICATION NO.   : 12/501981
DATED             : August 21, 2012
INVENTOR(S)       : Yoshiyuki Utsumi et al.

Page 1 of 1

It is certified that error appears in the above-identified patent and that said Letters Patent is hereby corrected as shown below:

At Column 5, Line 56, Change "(A)")" to --(A')")--.

At Column 5, Line 59, Change "(A)" to --(A')--.

At Column 6, Line 9, Change "(Al)" to --(A1)--.

At Column 63, Line 21 (Approx.), Change "(A2-1-6)" to --(a2-1-6)--.

At Column 88, Line 50, Change "preferred" to --preferred.--.

At Column 92, Line 4, Change "on" to --one--.

At Column 104, Line 30, Change "at it" to --as it--.

At Column 118, Lines 22-23, Change "(a1-12-1)" to --(A1-12-1)--.

At Column 119, Line 63, Change "3 s)" to --3s)--.

At Column 119, Line 65, Change "3 s" to --3s--.

At Column 120, Line 52 (Approx.), In Claim 1, change "$R^{13'}$may" to --$R^{13'}$ may--.

At Column 123, Line 65, In Claim 11, change "$R^{13'}$may" to --$R^{13'}$ may--.

Signed and Sealed this
Fifth Day of February, 2013

Teresa Stanek Rea
*Acting Director of the United States Patent and Trademark Office*